US008871778B2

(12) United States Patent
Choi et al.

(10) Patent No.: US 8,871,778 B2
(45) Date of Patent: Oct. 28, 2014

(54) SUBSTITUTED PYRIMIDINE COMPOUNDS AND THEIR USE AS SYK INHIBITORS

(71) Applicants: Genosco, Santa Fe Springs, CA (US); Oscotec, Inc., Choongnam (KR)

(72) Inventors: Jang-Sik Choi, Cheonan (KR); Hae-Jun Hwang, Chuncheon (KR); Eunho Lee, Gyeonggi-do (KR); Jaekyoo Lee, North Andover, MA (US); Ho-Juhn Song, Andover, MA (US); Se Won Kim, Gyeonggi-do (KR); Jung-Ho Kim, Gyeonggi-do (KR); Jong Sung Koh, Buchun (KR); Tae-im Lee, Gyeonggi-do (KR); Yung-geun Choi, Gyeonggi-do (KR); Ik-hwan Han, Namyangju (KR); Jaesang Lee, Belmont, MA (US); In Yong Lee, Belmont, MA (US); Dong Sik Jung, Chungcheongnam-do (KR)

(73) Assignees: Genosco, Santa Fe Springs, CA (US); Oscotec, Inc., Cheonan (KR)

( * ) Notice: Subject to any disclaimer, the term of this patent is extended or adjusted under 35 U.S.C. 154(b) by 0 days.

(21) Appl. No.: 13/745,734

(22) Filed: Jan. 18, 2013

(65) Prior Publication Data
US 2013/0274242 A1    Oct. 17, 2013

Related U.S. Application Data

(60) Provisional application No. 61/588,793, filed on Jan. 20, 2012.

(51) Int. Cl.
| | |
|---|---|
| A61K 31/505 | (2006.01) |
| C07D 405/14 | (2006.01) |
| C07D 401/14 | (2006.01) |
| A61K 31/5377 | (2006.01) |
| A61K 31/506 | (2006.01) |
| C07D 403/04 | (2006.01) |
| C07D 413/14 | (2006.01) |
| C07D 417/14 | (2006.01) |
| C07D 403/14 | (2006.01) |

(52) U.S. Cl.
CPC .......... *A61K 31/5377* (2013.01); *C07D 405/14* (2013.01); *C07D 401/14* (2013.01); *A61K 31/506* (2013.01); *C07D 403/04* (2013.01); *C07D 413/14* (2013.01); *C07D 417/14* (2013.01); *C07D 403/14* (2013.01)
USPC .......................................... 514/275; 544/324

(58) Field of Classification Search
CPC ............................ C07D 239/48; A61K 31/506
USPC .......................................... 544/324; 514/275
See application file for complete search history.

(56) References Cited

U.S. PATENT DOCUMENTS

| | | | | |
|---|---|---|---|---|
| 6,093,723 | A * | 7/2000 | Miao et al. | 514/292 |
| 8,629,132 | B2 * | 1/2014 | Lee et al. | 514/210.21 |
| 2011/0281841 | A1 * | 11/2011 | Lee et al. | 514/210.21 |

FOREIGN PATENT DOCUMENTS

| | | |
|---|---|---|
| WO | WO-2010-038081 | 4/2010 |
| WO | WO-2011-060295 | 5/2011 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
R. Singh et al., 42 Annual Reports in Medicinal Chemistry, 379-391, 380 (2007).*
Weinblatt et al., 363 The New England Journal of Medicine 1303-1312 (2010).*
N. Yamamoto et al., 306 The Journal of Pharmacology and Experimental Therapeutics, 1174-1181 (2003).*
E.S. Masuda et al., 21 Pulmonary Pharmacology & Therapeutics, 461-467 (2008).*
G-M Deng et al., 62 Arthritis & Rheumatism, 2086-2092 (2010).*
J.W. Friedberg et al., 115 Bood, 2578-2585 (2010).*
O.N. Pamuk et al., 12 Arthritis Research & Therapy, 1-11 (2010).*
F.M. Uckun et al., 107 PNAS, 2902-2907 (2010).*
M.E. Weinblatt et al., 363 New England Journal of Medicine, 1303-1312 (2010).*
International Search and Written Opinion mailed May 31, 2013, in corresponding PCT Application No. PCT/US2013/022135.

* cited by examiner

*Primary Examiner* — James O. Wilson
*Assistant Examiner* — Alexander R Pagano
(74) *Attorney, Agent, or Firm* — Edwards Wildman Palmer LLP; Kongsik Kim; Mark D. Russett

(57) ABSTRACT

Compounds of Formula (I) and methods for inhibiting kinases, including spleen tyrosine kinases, are disclosed. Also disclosed are methods for treating a kinase-mediated disease or condition by administering to a subject a therapeutically effective amount of the compound of Formula (I).

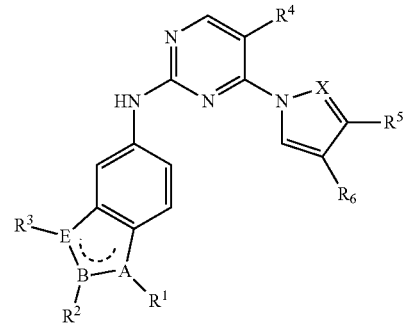

Formula I

20 Claims, No Drawings

SUBSTITUTED PYRIMIDINE COMPOUNDS AND THEIR USE AS SYK INHIBITORS

CROSS-REFERENCE TO RELATED APPLICATION

This application claims the benefit of and priority to U.S. Provisional Patent Application No. 61/588,793, filed Jan. 20, 2012, the contents of which are hereby incorporated by reference in their entirety.

BACKGROUND OF THE INVENTION

SYK (Spleen Tyrosine Kinase) is an intracellular tyrosine kinase that is involved in coupling activated immunoreceptors to signal downstream events that mediate diverse cellular responses, including proliferation, differentiation and phagocytosis.

The receptors in which SYK performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1 R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Ruzza et al., Expert Opin. Ther. Patents, 2009, 19 (10), 1361-1376; Ulanova et al., Expert Opin. Ther., Target., 2005, 9 (5), 901-921; Wang et al., J. Immunol., 2006, 177, 6859-6870; Slack et al., European J. Immunol., 2007, 37, 1600-1612).

Dysregulation and/or misregulation of different signal transduction pathways of SYK in different cell types have been implicated in numerous diseases and disorders e.g., allergic rhinitis, asthma, autoimmune diseases, rheumatoid arthritis (RA), osteopenia, osteoporosis, COPD and various leukemia and lymphomas. The inhibition of SYK activity by the present invention may offer a therapeutic option for treatment of many diseases associated with SYK activity.

Rheumatoid arthritis (RA) is an auto-immune disease characterized by inflammation of articular joints leading to debilitating destruction of bone and cartilage.

Studies using cells from SYK knocked-out mice displayed characteristic phenotypes by blocking in B cell development (M. Turner et al., Nature, 1995, 378, 298-302; Cheng et al., Nature, 1995, 378, 303-306). These studies and elsewhere demonstrate that SYK is required for the differentiation and activation of B cells. Therefore, inhibition of SYK activity in RA patients is likely to block B cell function and hence to reduce rheumatoid factor production. In addition to the role of SYK in B cell function, the requirement for SYK activity in Fc receptor (FcR) signaling is relevant to treatment of RA. FcR activation by immune complexes in RA has been suggested to contribute to the release of multiple pro-inflammatory mediators.

It was demonstrated that targeting B cell function by antibody rituximab, a B cell depleting antibody is an appropriate therapeutic strategy to treat auto-immune diseases such as RA (Edwards et al., New Eng. J. Med., 2004, 350 (25), 2572-2581). Furthermore, genetic deficiency of SYK in the hematopoietic compartment completely blocked the development of all macroscopic and microscopic signs of arthritis in autoantibody-induced arthritis mice model. In addition, it was demonstrated that the $SYK^{-/-}$ mutation prevented the appearance of periarticular bone erosions. Finally, $SYK^{-/-}$ bone marrow chimeras were completely protected from arthritis-induced loss of articular function (Jakus et al., Arthritis Rheum., 2010, 62 (7), 1899-1910).

SYK inhibitors may also be useful in cancer therapy, specifically heme malignancies, particularly Non-Hodgkin's Lymphomas including follicular (FL), mantle cell, Burkitt and diffuse large B cell (DLBCL) lymphomas. SYK is found to be dysregulated by overexpression and/or constitutively activation in a variety of primary B-lymphoma tumors and in B-lymphoma cell lines. Through the PI3K/AKT pathway, the PLD pathway and AKT independent signalling, SYK is known to activate mTOR (mammalian target of rapamycin) which in turn increases B-cell survival and proliferation. Inhibition of SYK in vitro results in decreased mTOR activation and a reduction of clonicity in FL cells. (Lesux L. et al., Blood, 2006, 108(13), 4156-4162 and Guruajan M. et al., J. Immun., 2007, 178, 111-121).

SYK inhibitors may also be useful in the treatment of asthma and rhinitis. Allergic rhinitis and asthma are diseases associated with hypersensitivity reactions and inflammatory events involving a multitude of cell types including mast cells, eosinophils, T cells and dendritic cells. SYK is positioned in transducing the downstream cellular signals associated with cross-linking FcεR1 and FcγR1 receptors. Following exposure to allergen, high affinity immunoglobulin receptors for IgE (FcεR1) and IgG (FcγR1) become cross-linked and activate downstream processes in mast cells and other cell types leading to release of pro-inflammatory mediators and airway spasmogens. In the mast cell, for example, IgE receptor cross-linking by allergen leads to release of mediators including histamine from preformed granules, as well as the synthesis and release of newly synthesized lipid mediators including prostaglandins and leukotrienes, which lead inflammatory events.

SYK inhibitors may also be useful in the treatment of urticaria triggered by allergic reactions but many cases have an unclear etiology. Acute and chronic urticaria are common skin diseases. There are many pathological similarities in chronic urticaria patients with allergen-induced mast and basophil cell degranulation reactions via IgE activation. Around 40% of chronic spontaneous urticaria patients contain serum IgG auto-antibodies targeting IgE or the FcεR and these are thought to drive the histamine and other mediator release via mast and basophil degranulation. SYK inhibitors would inhibit the signaling response post IgE medicated FcεR activation and inhibit the mediator release known to be involved in chronic pruritis in multiple diseases.

An inhibitor of the SYK kinase activity could also be used therapeutically in treating chronic obstructive pulmonary disease (COPD) caused by microbes and allegens. COPD is characterised by a successive deterioration in lung function and chronic inflammation of the airways, which is initiated and produced by noxious substances of all kinds and contributes to the maintenance of the course of the disease. At a cellular level, in COPD there is in particular a multiplication of T lymphocytes, neutrophils, granulocytes and macrophages. An increase in the number of CD8-positive lymphocytes is known to be directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections. An inhibitor of the SYK kinase activity could also be used therapeutically in acute lung deteriorations caused by Rhinoviruses.

WO03/057695A1 (Boehringer Ingelheim Pharmaceuticals, Inc.) describes novel 1,6-naphthyridines that have SYK inhibitory activity. Three more recent patent applications, WO2010/015518A2, WO2010/015520A1 and WO2011/092128A1 (Boehringer Ingelheim International GmbH) disclose compounds having SYK inhibitory activity.

WO04/035604A2 (Millennium Pharmaceuticals, Inc.) discloses the structural co-ordinates of the human SYK protein.

WO 2011/134971 A1 (Glaxo Group Ltd.) discloses 7-(1H-pyrazol-4-yl)-1,6-naphthyridine compounds as SYK inhibitors.

WO 2011/144585 A1 (F. Hoffmann-La Roche AG) discloses the pyrrolo[2,3-B]pyrazine-7-carboxamide derivatives and their use as JAK and SYK inhibitors.

There remains, however, a need to identify further compounds which are inhibitors of spleen tyrosine kinase (SYK).

SUMMARY OF THE INVENTION

The present invention relates to novel chemical compounds that display inhibition activity against the protein kinase SYK (Spleen Tyrosine Kinase), the preparation and formulation thereof and their use for therapy.

The present invention provides pyrimidine derivatives represented by Formula (I) and their use for the treatment of conditions such as respiratory complaints, allergic diseases, osteopenia, osteoporosis, gastrointestinal diseases, autoimmune diseases, inflammatory diseases and diseases of the peripheral or central nervous system, asthma, allergic rhinitis, rheumatoid arthritis, allergic dermatitis and COPD, and various leukemia and lymphomas, or other conditions treatable by inhibiting SYK activity.

The present invention provides a compound of Formula (I), as well as pharmacologically acceptable salts, diastereomers, enantiomers, racemates, hydrates or solvates thereof,

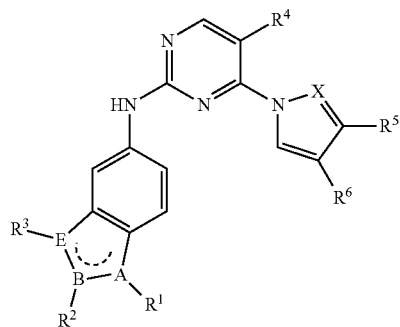

Formula (I)

Wherein:
A, B, E, $R^1$, $R^2$, $R^3$, $R^4$, $R^5$, $R^6$, and X are described herein.
X is CH or N;
--- is a single or a double bond;
A is C, CH, N, O or S;
B is C, CH or N;
E is C, CH, N, O or S;
When A is O or S, $R^1$ is absent;
When B is N and --- represents a double bond between B and E, $R^2$ is absent;
When E is O or S, $R^3$ is absent;
When A is C, or CH, then
$R^1$ is selected from H, halo, $C_1$-$C_6$alkyl, $C_3$-$C_7$cycloalkyl, $C_5$-$C_8$heterocycloalkyl, aryl, arylalkyl, heteroaryl, C(O)$NR^7R^7$, C(O)$R^7$, S(O)$_n$$R^7$, S(O)$_n$$NR^7R^7$, C(O)$NR^8R^9$, or S(O)$_n$$NR^8R^9$, wherein each n is 1 or 2 and the $C_1$-$C_6$ alkyl, $C_3$-$C_7$cycloalkyl, $C_5$-$C_8$heterocycloalkyl, aryl, arylalkyl, or heteroaryl is optionally substituted with one or more halo, amino, hydroxy, $OR^7$, $NHR^7$, $NR^7R^7$, $NR^8R^9$, or $C_3$-$C_7$cycloalkyl;
When A is N, then
$R^1$ is selected from H, $C_1$-$C_6$alkyl, $C_3$-$C_7$cycloalkyl, $C_5$-$C_8$heterocycloalkyl, aryl, arylalkyl, heteroaryl, C(O)$NR^7R^7$, C(O)$R^7$, S(O)$_n$$R^7$, S(O)$_n$$NR^7R^7$, C(O)$NR^8R^9$, or S(O)$_n$$NR^8R^9$, wherein each n is 1 or 2 and the $C_1$-$C_6$ alkyl, $C_3$-$C_7$cycloalkyl, $C_5$-$C_8$heterocycloalkyl, aryl, arylalkyl, or heteroaryl is optionally substituted with one or more halo, amino, hydroxy, $OR^7$, $NHR^7$, $NR^7R^7$, $NR^8R^9$, or $C_3$-$C_7$cycloalkyl;
$R^8$ and $R^9$, taken together with the nitrogen atom to which they are bonded form, independently for each occurrence:
  i) a 3-8 membered saturated or partially saturated monocyclic group having no heteroatom other than the nitrogen atom to which $R^8$ and $R^9$ are bonded, wherein said 3-8 membered saturated or partially saturated monocyclic group is optionally and independently substituted at one or more carbon atoms with halo, amino, hydroxy, $R^7$, $OR^7$, $SR^7$, $NHR^7$, $NR^7R^7$ or $NR^8R^9$; or
  ii) a 5-8 membered saturated or partially saturated monocyclic group having 1 or 2 heteroatoms selected from nitrogen, oxygen, sulfur, sulfone or sulfoxide, wherein said 5-8 membered saturated or partially saturated monocyclic group having 1 or 2 heteroatoms is optionally substituted with $R^7$;
When B is C or CH, then,
$R^2$ is selected from H, halo, $CF_3$, $C_1$-$C_4$alkyl or aryl, wherein the $C_1$-$C_4$alkyl or aryl is optionally substituted with one or more halo, amino, hydroxy, alkoxy, or haloalkyl;
When B is N, then,
$R^2$ is H or $C_1$-$C_4$alkyl, wherein the $C_1$-$C_4$alkyl is optionally substituted with one or more halo, hydroxy, or alkoxy;
When E is C, or CH, then
$R^3$ is selected from H, halo, $C_1$-$C_6$alkyl, $C_3$-$C_7$cycloalkyl, $C_6$-$C_{10}$aryl, heteroaryl, C(O)$NR^7R^7$, C(O)$R^7$, $NR^7R^7$, S(O)$_n$$R^7$, S(O)$_n$$NR^7R^7$, $(CH_2)_n$$NR^7R^7$, $NR^8R^9$, $(CH_2)_n$$NR^8R^9$, C(O)$NR^8R^9$, or S(O)$_n$$NR^8R^9$, wherein each n is 1 or 2 and the $C_1$-$C_6$ alkyl, $C_3$-$C_7$cycloalkyl, $C_5$-$C_8$heterocycloalkyl, $C_6$-$C_{10}$aryl, or heteroaryl is optionally substituted with one or more halo, amino, hydroxy, haloalkyl, $NR^7R^7$, $NR^8R^9$, or $OR^7$;
When E is N, then
$R^3$ is selected from H, $C_1$-$C_6$alkyl, $C_3$-$C_7$cycloalkyl, $C_6$-$C_{10}$aryl, heteroaryl, C(O)$NR^7R^7$, C(O)$R^7$, $CH_2CH_2NR^7R^7$, S(O)$_n$$R^7$, S(O)$_n$$NR^7R^7$, $CH_2CH_2NR^8R^9$, C(O)$NR^8R^9$, or S(O)$_n$$NR^8R^9$, wherein each n is 1 or 2 and the $C_1$-$C_6$ alkyl, $C_3$-$C_7$cycloalkyl, $C_6$-$C_{10}$ aryl, or heteroaryl is optionally substituted with one or more halo, amino, hydroxy, alkoxy, $C_1$-$C_6$alkyl, haloalkyl, $NR^7R^7$, $NR^8R^9$, or $OR^7$;
$R^4$ is selected from H, halo, $C_1$-$C_6$alkyl, $C_3$-$C_7$cycloalkyl, wherein the $C_1$-$C_6$alkyl, or $C_3$-$C_7$cycloalkyl is optionally substituted with one or more halo, amino, hydroxy, alkoxy, or haloalkyl;
$R^5$ is selected from H, halo, $C_1$-$C_6$alkyl, $CF_3$, CN, $C_3$-$C_7$cycloalkyl, aryl or $C_5$-$C_8$ heteroaryl, wherein $C_3$-$C_7$cycloalkyl, aryl or $C_5$-$C_8$heteroaryl is optionally and independently substituted with one or more halo, amino, hydroxy, alkoxy, or haloalkyl;
$R^6$ is selected from $CH_2OH$, $(CH_2)_n$$NH_2$, $(CH_2)_n$$OR^7$, $(CH_2)_n$$NHR^7$, $(CH_2)_n$$NR^7R^7$, $(CH_2)_n$$NR^7R^{10}$, C(O)$NHR^7$, C(O)$NR^7R^7$, C(O)$NR^7R^{10}$, $(CH_2)_n$C(O)$OR^7$, C(O)$R^7$, $(CH_2)_n$$NHS(O)_n$$R^7$, $(CH_2)_n$$NR^7S(O)nR^7$, $(CH_2)_n$$NR^{11}R^{12}$, C(O)$NR^{11}R^{12}$, or $(CH_2)_n$CN, wherein each n is independently 1 or 2;
$R^7$ is independently selected from $C_1$-$C_6$ alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl, wherein the $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl is optionally and independently substituted with one or more aryl, cycloalkyl, heteroaryl, heterocyclyl, alkyl, halo, amino, hydroxy, or $R^{13}$;

Each $R^{10}$ is independently selected from $C(O)R^7$, $C(O)OR^7$, $C(O)NR^7R^7$ or $S(O)_nR^7$, wherein n is 1 or 2;

Each $R^{13}$ is independently selected from $SR^7$, $OR^7$, $NR^7R^7$, $C(O)NR^7R^7$, $S(O)_nNR^7R^7$, $S(O)_nR^7$, $NR^8R^9$, or $C(O)R^8R^9$, wherein each n is independently 1 or 2;

$R^{11}$ and $R^{12}$, taken together with the nitrogen atom to which they are bonded form, independently for each occurrence:

i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbon atoms with $R^{14}$, wherein $R^{14}$ is CN, $(CH_2)_nOH$, $(CH_2)_nOR^7$, COOH, $COOR^7$, halo, amino, hydroxy, $R^7$, $OR^7$, $SR^7$, $NHR^7$, $NR^7R^7$, $NR^8R^9$, NHC(O)$NHR^7$, NHC(O)$NR^7R^7$, $OC(O)R^7$, NHC(O)$NR^8R^9$, $NHS(O)_nR^7$, $NHS(O)_nNHR^7$, wherein n is independently 1 or 2; or ii) a 5-8 membered saturated or partially saturated monocyclic group having 1 or 2 heteroatoms selected from nitrogen, oxygen, sulfur, sulfone or sulfoxide, wherein said 5-8 membered saturated or partially saturated monocyclic group having 1 or 2 heteroatoms is optionally substituted with $R^7$;

or a pharmaceutically acceptable salt thereof.

In one aspect, the present invention provides pharmaceutical compositions comprising a compound of Formula (I) and a pharmaceutically acceptable carrier. In certain embodiments, such pharmaceutical compositions are formulated for intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration. In other embodiments, such pharmaceutical composition are formulated as tablets, pills, capsules, a liquid, an inhalant, a nasal spray solution, a suppository, a solution, a gel, an emulsion, an ointment, eye drops or ear drops.

In one aspect, the present invention provides methods for treating a cell-proliferative disease or condition, such as cancer, comprising administering to a subject in need of such treatment a therapeutically effective amount of the compound of Formula (I) or pharmaceutically acceptable salts, pharmaceutical compositions or medicaments thereof, wherein the cell proliferative disease or condition include, for example, B-cell and/or T cell-lymphoma. In one aspect, the present invention provides methods of inhibiting growth of cancer cells with a compound of Formula (I) or a pharmaceutically acceptable salt thereof.

In another aspect, the present invention provides a medicament for treating a SYK-mediated disease, disorder or condition in a patient comprising a therapeutically effective amount of the compound of Formula (I).

In another aspect, the present invention provides methods for inhibiting protein kinases, comprising administering to a subject in need thereof, a therapeutically effective amount of the compound of Formula (I) or a pharmaceutically acceptable salt or pharmaceutical composition thereof. The protein kinase includes, but is not limited to, SYK kinase.

In another aspect, the present invention provides methods for inhibiting protein kinases, comprising contacting a cell with a compound of Formula (I). In certain embodiment, the compound of Formula (I) effectively inhibits activity of one or more kinases and associated mutants selected from SYK, MLK1, or PLK3. In certain embodiments, protein kinase-mediated diseases or conditions are inflammatory diseases or conditions, respiratory diseases or autoimmune diseases or conditions, such as asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, breast cancer, HIV associated diseases or lupus.

In another aspect, the present invention provides methods of treating a kinase-mediated disease or condition by administering to a subject a therapeutically effective amount of the compound of Formula (I) or a pharmaceutically acceptable salt, in combination with a second therapeutic agent.

In another aspect, the invention relates to the use of the compounds of the invention for the preparation of a medicament for the treatment of a kinase-mediated disease or condition.

The present invention also relates to compositions comprising these compounds, methods of making these compounds, methods of inhibiting enzyme activity, particularly SYK kinase activity, through use of these compounds, and method of treating disease or disease symptoms in a mammal, particularly where inhibition of the kinase activity, can affect disease outcome.

Other aspects and embodiments of the invention will be apparent from the following description.

DETAILED DESCRIPTION OF THE INVENTION

The present invention provides a group of substituted pyrimidine derivatives and pharmaceutically acceptable salts thereof that are useful for inhibiting SYK kinase activity and for treating diseases and disorders that are mediated by SYK kinase such as inflammatory diseases including rheumatoid arthritis, autoimmune diseases including rhinitis, cancer including leukemia, lymphoma, and osteoporosis. The present invention also provides methods of preparing pyrimidine derivatives. The present invention also provides pharmaceutical formulations comprising at least one of the compounds of the present invention together with a pharmaceutically acceptable carrier, diluent or excipient thereof. The invention also provides useful intermediates generated during syntheses of the pyrimidine derivative compounds.

The present invention provides a compound of Formula (I), or individual stereoisomer, mixture of isomers, or pharmaceutically acceptable salt thereof,

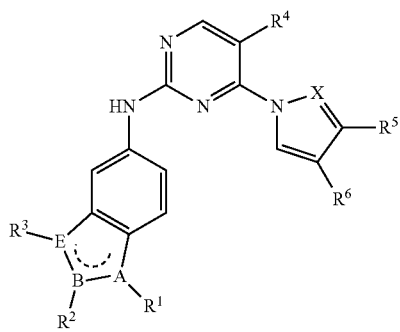

Formula (I)

X is CH or N;
⸺ is a single or a double bond;
A is C, CH, N, O or S;
B is C, CH or N;
E is C, CH, N, O or S;

When A is O or S, $R^1$ is absent;

When B is N and ═══ represents a double bond between B and E, $R^2$ is absent;

When E is O or S, $R^3$ is absent;

When A is C, or CH, then $R^1$ is selected from H, halo, $C_1$-$C_6$alkyl, $C_3$-$C_7$cycloalkyl, $C_5$-$C_8$heterocycloalkyl, aryl, arylalkyl, heteroaryl, C(O)NR$^7$R$^7$, C(O)R$^7$, S(O)$_n$R$^7$, S(O)$_n$NR$^7$R$^7$, C(O)NR$^8$R$^9$, or S(O)$_n$NR$^8$R$^9$, wherein each n is independently 1 or 2. More specifically, $R^1$ can be Cl, Br, methyl, ethyl, isopropyl, cyclopropyl, acetyl, methanesulfonyl, or arenesulfonyl. The $C_1$-$C_6$alkyl, $C_3$-$C_7$cycloalkyl, $C_5$-$C_8$heterocycloalkyl, aryl, arylalkyl, or heteroaryl is optionally substituted with one or more halo, amino, hydroxy, OR$^7$, NHR$^7$, NR$^7$R$^7$, NR$^8$R$^9$, or $C_3$-$C_7$cycloalkyl;

When A is N, then $R^1$ is selected from H, $C_1$-$C_6$alkyl, $C_3$-$C_7$cycloalkyl, $C_5$-$C_8$heterocycloalkyl, aryl, arylalkyl, heteroaryl, C(O)NR$^7$R$^7$, C(O)R$^7$, S(O)$_n$R$^7$, S(O)$_n$NR$^7$R$^7$, C(O)NR$^8$R$^9$, or S(O)$_n$NR$^8$R$^9$, wherein each n is 1 or 2. More specifically, $R^1$ can be Cl, Br, methyl, ethyl, isopropyl, cyclopropyl, acetyl, methanesulfonyl, or arenesulfonyl. The $C_1$-$C_6$ alkyl, $C_3$-$C_7$cycloalkyl, $C_5$-$C_8$heterocycloalkyl, aryl, arylalkyl, or heteroaryl is optionally substituted with one or more halo, amino, hydroxy, OR$^7$, NHR$^7$, NR$^7$R$^7$, NR$^8$R$^9$, or $C_3$-$C_7$ cycloalkyl;

$R^8$ and $R^9$, taken together with the nitrogen atom to which they are bonded form, independently for each occurrence:
  i) a 3-8 membered saturated or partially saturated monocyclic group having no heteroatom other than the nitrogen atom to which $R^8$ and $R^9$ are bonded, wherein said 3-8 membered saturated or partially saturated monocyclic group is optionally and independently substituted at one or more carbon atoms with halo, amino, hydroxy, R$^7$, OR$^7$, SR$^7$, NHR$^7$, NR$^7$R$^7$, or NR$^8$R$^9$. More specifically, NR$^8$R$^9$ can be azetidinyl, pyrrolidinyl, or piperidinyl optionally and independently substituted with halo, amino, hydroxy, R$^7$, OR$^7$, SR$^7$, NHR$^7$, NR$^7$R$^7$, or NR$^8$R$^9$; or
  ii) a 5-8 membered saturated or partially saturated monocyclic group having 1 or 2 heteroatoms selected from nitrogen, oxygen, sulfur, sulfone or sulfoxide, wherein said 5-8 membered saturated or partially saturated monocyclic group having 1 or 2 heteroatoms is optionally substituted with R$^7$. More specifically, NR$^8$R$^9$ can be morpholinyl, thiomorpholinyl, piperazinyl, or homopiperazinyl optionally and independently substituted with R$^7$;

When B is C or CH, then, $R^2$ is selected from H, halo, CF$_3$, $C_1$-$C_4$alkyl or aryl, wherein the $C_1$-$C_4$alkyl or aryl is optionally substituted with one or more halo, amino, hydroxy, alkoxy, or haloalkyl;

When B is N, then, $R^2$ is H or $C_1$-$C_4$alkyl, wherein the $C_1$-$C_4$alkyl is optionally substituted with one or more halo, hydroxy, or alkoxy;

When E is C, or CH, then $R^3$ is selected from H, halo, $C_1$-$C_6$alkyl, $C_3$-$C_7$cycloalkyl, $C_6$-$C_{10}$aryl, heteroaryl, C(O)NR$^7$R$^7$, C(O)R$^7$, NR$^7$R$^7$, S(O)$_n$R$^7$, S(O)$_n$NR$^7$R$^7$, (CH$_2$)$_n$NR$^7$R$^7$, NR$^8$R$^9$, (CH$_2$)$_n$NR$^8$R$^9$, C(O)NR$^8$R$^9$, or S(O)$_n$NR$^8$R$^9$, wherein each n is 1 or 2, and the $C_1$-$C_6$alkyl, $C_3$-$C_7$cycloalkyl, $C_5$-$C_8$heterocycloalkyl, $C_6$-$C_{10}$aryl, or heteroaryl is optionally substituted with one or more halo, amino, hydroxy, haloalkyl, NR$^7$R$^7$, NR$^8$R$^9$, or OR$^7$. More specifically, $R^3$ can be Cl, Br, methyl, ethyl, isopropyl, cyclopropyl, acetyl, methanesulfonyl, or arenesulfonyl;

When E is N, then $R^3$ is selected from H, $C_1$-$C_6$alkyl, $C_3$-$C_7$cycloalkyl, $C_6$-$C_{10}$aryl, heteroaryl, C(O)NR$^7$R$^7$, C(O)R$^7$, NR$^7$R$^7$, S(O)$_n$R$^7$, S(O)$_n$NR$^7$R$^7$, CH$_2$CH$_2$NR$^7$R$^7$, NR$^8$R$^9$, CH$_2$CH$_2$NR$^8$R$^9$, C(O)NR$^8$R$^9$, or S(O)$_n$NR$^8$R$^9$, wherein each n is 1 or 2, and the $C_1$-$C_6$ alkyl, $C_3$-$C_7$cycloalkyl, $C_5$-$C_8$heterocycloalkyl, $C_6$-$C_{10}$aryl, or heteroaryl is optionally substituted with one or more halo, amino, hydroxy, alkoxy, $C_1$-$C_6$alkyl, haloalkyl, NR$^7$R$^7$, NR$^8$R$^9$, or OR$^7$. More specifically, $R^3$ can be methyl, ethyl, isopropyl, cyclopropyl, acetyl, methanesulfonyl, or arenesulfonyl;

$R^4$ is selected from H, halo, CF$_3$, $C_1$-$C_6$alkyl, $C_3$-$C_7$cycloalkyl, wherein the $C_1$-$C_6$alkyl, or $C_3$-$C_7$cycloalkyl is optionally substituted with one or more one or more halo, amino, hydroxy, alkoxy, or haloalkyl. More specifically, $R^4$ can be F, Cl, Br, I, CH$_3$, CF$_3$, CH$_2$CH$_3$, isopropyl, or cyclopropyl;

$R^5$ is selected from H, halo, $C_1$-$C_6$alkyl, CF$_3$, CN, $C_3$-$C_7$cycloroalkyl, aryl or $C_5$-$C_8$heteroaryl, wherein $C_3$-$C_7$cycloroalkyl, aryl or $C_5$-$C_8$heteroaryl is optionally and independently substituted with one or more halo, amino, hydroxy, alkoxy, or haloalkyl;

$R^6$ is selected from CH$_2$OH, (CH$_2$)$_n$NH$_2$, (CH$_2$)$_n$OR$^7$, (CH$_2$)$_n$NHR$^7$, (CH$_2$)$_n$NR$^7$R$^7$, (CH$_2$)$_n$NR$^7$R$^{10}$, C(O)NHR$^7$, C(O)NR$^7$R$^7$, C(O)NR$^7$R$^{10}$, (CH$_2$)$_n$C(O)OR$^7$, C(O)R$^7$, (CH$_2$)$_n$NHS(O)$_n$R$^7$, (CH$_2$)$_n$NR$^7$S(O)$_n$R$^7$, (CH$_2$)$_n$NR$^{11}$R$^{12}$, C(O)NR$^{11}$R$^{12}$, or (CH$_2$)$_n$CN, wherein each n is independently 1 or 2;

$R^7$ is independently selected from $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl, wherein the $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl is optionally and independently substituted with one or more aryl, cycloalkyl, heteroaryl, heterocyclyl, alkyl, halo, amino, hydroxy, or R$^{13}$;

Each $R^{10}$ is independently selected from C(O)R$^7$, C(O)OR$^7$, C(O)NR$^7$R$^7$, or S(O)$_n$R$^7$, wherein n is 1 or 2;

Each $R^{13}$ is independently selected from SR$^7$, OR$^7$, NR$^7$R$^7$, C(O)NR$^7$R$^7$, S(O)$_n$NR$^7$R$^7$, S(O)$_n$R$^7$, NR$^8$R$^9$, or C(O)R$^8$R$^9$, wherein each n is independently 1 or 2;

$R^{11}$ and $R^{12}$, taken together with the nitrogen atom to which they are bonded form, independently for each occurrence:
  i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbon atoms with $R^{14}$, wherein $R^{14}$ is COOH, COOR$^7$, CN, (CH$_2$)$_n$OH, (CH$_2$)$_n$OR$^7$, halo, amino, hydroxy, R$^7$, OR$^7$, SR$^7$, NHR$^7$, NR$^7$R$^7$, NR$^8$R$^9$, NHC(O)$_n$NHR$^7$, NHC(O)NR$^7$R$^7$, OC(O)R$^7$, NHC(O)NR$^8$R$^9$, NHS(O)$_n$R$^7$, NHS(O)$_n$NHR$^7$, wherein n is 1 or 2; or
  ii) a 5-8 membered saturated or partially saturated monocyclic group having 1-2 heteroatoms selected from nitrogen, oxygen, sulfur, sulfone, or sulfoxide, wherein said 5-8 membered saturated or partially saturated monocyclic group having 1-2 heteroatoms is optionally substituted with R$^7$;

or a pharmaceutically acceptable salt thereof.

In one embodiment, $R^1$ is selected from $C_1$-$C_6$alkyl, $C_3$-$C_7$cycloalkyl, $C_5$-$C_8$heterocycloalkyl, aryl, arylalkyl, or heteroaryl. Wherein, the $C_1$-$C_6$alkyl, $C_3$-$C_7$cycloalkyl, $C_5$-$C_8$heterocycloalkyl, aryl, arylalkyl, or heteroaryl is optionally and independently substituted at one or more carbon atoms with halo, amino, hydroxy, $OR^7$, $NHR^7$, $NR^7R^7$, $NR^8R^9$, or $C_3$-$C_7$cycloalkyl.

In one embodiment, $R^1$ is $C(O)NR^7R^7$, $C(O)R^7$, $S(O)_nR^7$, or $S(O)_nNR^7R^7$, wherein each n is 1 or 2. $R^7$ is independently selected from $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl. The $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl is optionally and independently substituted with one or more aryl, cycloalkyl, heteroaryl, heterocyclyl, alkyl, halo, amino, hydroxy, or $R^{11}$.

In one embodiment, $R^1$ is $C(O)NR^8R^9$, or $S(O)_nNR^8R^9$, wherein each n is 1 or 2. $R^8$ and $R^9$, taken together with the nitrogen atom to which they are bonded form: (i) a 3-8 membered saturated or partially saturated monocyclic group having no heteroatom other than the nitrogen atom to which $R^8$ and $R^9$ are bonded, wherein said 3-8 membered saturated or partially saturated monocyclic group is optionally and independently substituted at one or more carbon atoms with halo, amino, hydroxy, $R^7$, $OR^7$, $SR^7$, $NHR^7$, $NR^7R^7$, $NR^8R^9$; (ii) a 5-8 membered saturated or partially saturated monocyclic group having 1 or 2 heteroatoms selected from nitrogen, oxygen, sulfur, sulfone or sulfoxide, wherein said 5-8 membered saturated or partially saturated monocyclic group having 1 or 2 heteroatoms is optionally substituted with $R^7$.

In certain aspects, $R^2$ is selected from H, halo, $CF_3$, $C_1$-$C_4$alkyl or aryl, wherein the $C_1$-$C_4$alkyl or aryl is optionally substituted with one or more halo, amino, hydroxy, alkoxy, or haloalkyl. In certain aspects, $R^3$ is selected from H, halo, $C_1$-$C_6$alkyl, $C_3$-$C_7$cycloalkyl, $C_6$-$C_{10}$aryl, heteroaryl, $C(O)NR^7R^7$, $C(O)R^7$, $NR^7R^7$, $S(O)_nR^7$, $S(O)_nNR^7R^7$, $(CH_2)_nNR^7R^7$, $NR^8R^9$, $(CH_2)_nNR^8R^9$, $C(O)NR^8R^9$, or $S(O)_nNR^8R^9$, wherein each n is 1 or 2. The $C_1$-$C_6$alkyl, $C_3$-$C_7$cycloalkyl, $C_5$-$C_8$heterocycloalkyl, $C_6$-$C_{10}$aryl, or heteroaryl is optionally substituted with one or more halo, amino, hydroxy, $C_1$-$C_6$alkyl, haloalkyl, $NR^7R^7$, $NR^8R^9$, or $OR^7$.

In one embodiment, $R^3$ is halo, e.g., F, Cl, Br, or I.

In one embodiment, $R^3$ is $C_1$-$C_6$alkyl, $C_3$-$C_7$cycloalkyl, $C_6$-$C_{10}$aryl, or heteroaryl. The $C_6$-$C_{10}$aryl is phenyl or naphthyl optionally and independently substituted with one or more halo, amino, hydroxy, $C_1$-$C_6$alkyl, haloalkyl, $NR^7R^7$, $NR^8R^9$, or $OR^7$. The heteroaryl group of $R^3$ can be heteroaryl containing one or more heteroatoms independently selected from nitrogen, oxygen, sulfur, sulfoxide, or sulfone. The heteroaryl group of $R^3$ can be a 5-6 membered monocyclic aryl group having 1-3 heteroatoms independently selected from nitrogen, oxygen, or sulfur, or an 8-10 membered bicyclic aryl group having 1-5 heteroatoms independently selected from nitrogen, oxygen, sulfur, sulfoxide, or sulfone.

In one embodiment, the heteroaryl of $R^3$ is a 5-6 membered monocyclic aryl group such as oxazolyl, thiazolyl, pyridyl, or pyrimidinyl, each optionally and independently substituted with 1 or 2 groups selected from methyl, ethyl, isopropyl, cyclopropyl, or phenyl.

In one embodiment, $R^3$ is $C(O)R^7$ or $C(O)NR^7R^7$. In certain embodiments, $R^7$ is independently selected from $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl. The $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl is optionally and independently substituted with one or more aryl, cycloalkyl, heteroaryl, heterocyclyl, alkyl, halo, amino, hydroxy, or $R^{13}$. $R^7$ is $C_1$-$C_6$alkyl, $C_3$-$C_7$cycloalkyl, or haloalkyl. The haloalkyl of $R^7$ can be $CF_3$, $CHF_2$, $CH_2F$, or $CH_2CF_3$.

In one embodiment, $R^3$ is $NR^8R^9$, $(CH_2)_nNR^8R^9$, or $S(O)_nNR^8R^9$, wherein each n is 1 or 2, $R^8$ and $R^9$, taken together with the nitrogen atom to which they are bonded form: (i) a 3-8 membered saturated or partially saturated monocyclic group having no heteroatom other than the nitrogen atom to which $R^8$ and $R^9$ are bonded, wherein said 3-8 membered saturated or partially saturated monocyclic group is optionally and independently substituted at one or more carbon atoms with halo, amino, hydroxy, $R^7$, $OR^7$, $SR^7$, $NHR^7$, $NR^7R^7$, $NR^8R^9$; (ii) a 5-8 membered saturated or partially saturated monocyclic group having 1 or 2 heteroatoms selected from nitrogen, oxygen, sulfur, sulfone or sulfoxide, wherein said 5-8 membered saturated or partially saturated monocyclic group having 1 or 2 heteroatoms is optionally substituted with $R^7$. Preferably, the 3-8 membered ring selected from azetidinyl, pyrrolidinyl, or piperidinyl optionally and independently substituted with hydroxy, amino, or $R^7$.

In one embodiment, $R^3$ is $S(O)_nR^7$ or $S(O)_nNR^7R^7$, wherein each n is 1 or 2. In certain embodiments, $R^7$ can be independently selected from methyl, ethyl, cyclopropyl, phenyl, or phenyl substituted with $C_1$-$C_6$alkyl, $CF_3$, or halo.

In certain aspects, $R^4$ is selected from H, F, Cl, Br, $C_1$-$C_6$alkyl, or $C_3$-$C_7$cycloalkyl, wherein the $C_1$-$C_6$alkyl, or $C_3$-$C_7$cycloalkyl is optionally substituted with one or more halo, amino, hydroxy, alkoxy, or haloalkyl.

In certain aspects, $R^5$ is selected from H, halo, $C_1$-$C_6$alkyl, $CF_3$, CN, $C_3$-$C_7$cycloalkyl, aryl or $C_5$-$C_8$heteroaryl, wherein $C_3$-$C_7$cycloroalkyl, aryl or $C_5$-$C_8$heteroaryl is optionally and independently substituted with one or more halo, amino, hydroxy, alkoxy, or haloalkyl.

In one embodiment, $R^6$ is $CH_2OH$, $(CH_2)_nNH_2$, $(CH_2)_nOR^7$, $(CH_2)_nNHR^7$, $(CH_2)_nNR^7R^7$, $(CH_2)_nNR^7R^{10}$, $C(O)NHR^7$, $C(O)NR^7R^7$, $C(O)NR^7R^{10}$, $(CH_2)_nC(O)OR^7$, $C(O)R^7$, $(CH_2)_nNHS(O)_nR^7$, $(CH_2)_nNR^7S(O)_nR^7$, $(CH_2)_nNR^{11}R^{12}$, $C(O)NR^{11}R^{12}$, wherein each n is independently 1 or 2. $R^7$ is independently selected from $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl. The $C_2$-$C_6$alkyl, $C_3$-$C_6$alkenyl, $C_3$-$C_6$alkynyl, $C_3$-$C_7$cycloalkyl, aryl, aryl($C_1C_4$)alkyl, haloalkyl, heteroaryl, or heterocyclyl is optionally and independently substituted with one or more aryl, cycloalkyl, heteroaryl, heterocyclyl, alkyl, halo, amino, hydroxy, or $R^{13}$. For example, $R^7$ is $C_1$-$C_6$alkyl, $C_3$-$C_7$cycloalkyl, or haloalkyl. The haloalkyl of $R^7$ can be $CF_3$, $CHF_2$, $CH_2F$, or $CH_2CF_3$. $R^{10}$ is independently selected from $C(O)R^7$, $C(O)OR^7$, $C(O)NR^7R^7$, or $S(O)_nR^7$, wherein n is 1 or 2.

In one embodiment, $R^6$ is $(CH_2)_nNR^{11}R^{12}$ or $C(O)NR^{11}R^{12}$, wherein each n is independently 1 or 2. $R^{11}$ and $R^{12}$, taken together with the nitrogen atom to which they are bonded form: (i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbon atoms with $R^{14}$, wherein $R^{14}$ is COOH, $COOR^7$, CN, $(CH_2)OH$, $(CH_2)_nOR^7$, halo, amino, hydroxy, $R^7$, $OR^7$, $SR^7$, $NHR^7$, $NR^7R^7$, $NR^8R^9$, $NHC(O)NHR^7$, $NHC(O)NR^7R^7$, $OC(O)R^7$, $NHC(O)NR^8R^9$, $NHS(O)_nR^7$, or $NHS(O)_nNHR^7$, wherein n is 1 or 2; (ii) a 5-8 membered saturated or partially saturated monocyclic group having 1 or 2 heteroatoms selected from nitrogen, oxygen, sulfur, sulfone, or sulfoxide, wherein said 5-8 membered saturated or partially saturated monocyclic group having 1 or 2 heteroatoms is optionally substituted with $R^7$. The 3-8 membered saturated or partially saturated monocyclic ring having no heteroatom other than the bound nitrogen can be a 4-6 membered saturated ring optionally and independently substituted with one or more hydroxy, amino, halo, COOH, $COOR^7$, $R^7$, $OR^7$, $SR^7$, $NHR^7$, $NR^7R^7$, $NR^8R^9$, $NHC(O)NHR^7$, $NHC(O)NR^7R^7$, $OC(O)R^7$, $NHC(O)NR^8R^9$, $NHS(O)_nR^7$, $NHS(O)_n$NHR at one or more substitutable carbon atoms. Preferably, the 3-8 membered ring is selected from azetidinyl, pyrrolidinyl or piperidinyl optionally and independently substituted with one or more hydroxy, amino, halo, COOH, COOR$^7$, CN, (CH$_2$)$_n$OH, (CH$_2$)$_n$OR$^7$, R$^7$, OR$^7$, SR$^7$, NHR$^7$, NR$^7$R$^7$, NR$^8$R$^9$, NHC(O)NHR$^7$, NHC(O)NR$^7$R$^7$, OC(O)R$^7$, NHC(O)NR$^8$R$^9$, NHS(O)$_n$R$^7$, NHS(O)$_n$NHR at one or more substitutable carbon atoms;

or a pharmaceutically acceptable salt thereof;

The term "alkyl," used alone or as part of a larger moiety such as "arylalkyl" or "cycloalkyl" refers to a straight or branched hydrocarbon radical having from 1 to 15 carbon atoms or from 1-8 carbon atoms (unless stated otherwise) and includes, for example, methyl, ethyl, n-propyl, iso-propyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, and oxygen.

The term "heterocycloalkyl" means a non-aromatic monocyclic or polycyclic ring comprising carbon and hydrogen atoms and at least one heteroatom, preferably, 1 to 4 heteroatoms selected from nitrogen, sulfur, oxygen, sulfone, or sulfoxide. A heterocycloalkyl group can have one or more carbon-carbon double bonds or carbon-heteroatom double bonds in the ring group as long as the ring group is not rendered aromatic by their presence.

Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkoxy" refers to the alkyl groups above bound through oxygen, examples of which include methoxy, ethoxy, iso-propoxy, tert-butoxy, and the like. In addition, alkoxy also refers to polyethers such as —O—(CH$_2$)$_2$—O—CH$_3$, and the like. An alkoxy can be unsubstituted or substituted with one or more suitable substituents.

As used herein, the term "aryl" refers to unsubstituted or substituted aromatic monocyclic or polycyclic groups and includes, for example, phenyl and naphthyl. The term "aryl" also includes a phenyl ring fused to a non-aromatic carbocyclic or heterocyclic ring. The term "aryl" may be interchangeably used with "aryl ring," aromatic group," and "aromatic ring." Heteroaryl groups have 4 to 14 atoms, 1 to 9 of which are independently selected from the group consisting of oxygen, sulfur and nitrogen. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "haloalkyl" refers to any alkyl radical having one or more hydrogen atoms replaced by a halogen atom. Examples of haloalkyl include —CF3, —CFH$_2$, —CF$_2$H, and the like.

As used herein, the term "hydroxyl" or "hydroxy" refers to —OH.

As used herein, the term "amino" refers to —NH$_2$.

As used herein, the term "hydroxyalkyl" refers to any hydroxyl derivative of alkyl radical. The term "hydroxyalkyl" includes any alkyl radical having one or more hydrogen atoms replaced by a hydroxy group.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, haloalkyl, aryl, hydroxy, alkoxy, hydroxyalkyl, amino, and the like.

In certain aspects, the invention also provides (i) a method of preparing a compound of formula (c) by reacting a compound of formula (a) with a compound of formula (b) in the presence of the first base in the first organic solvent (see Scheme 1); (ii) a method of preparing a compound of formula (e) by reacting the compound of formula (c) with aniline derivatives (d) in the presence of the second base, ligand, palladium catalyst in the second organic solvent (see Scheme 1); (iii) a method of preparing a compound of Formula (I) by reductive amination of the compound of formula (e) and an amine derivatives (R$_6$) by using a reducing agent in the third solvent (see Scheme 1). The invention also provides a method of preparing a compound of Formula (I) according to Scheme 1 (Method 1).

Scheme 1 (Method 1)

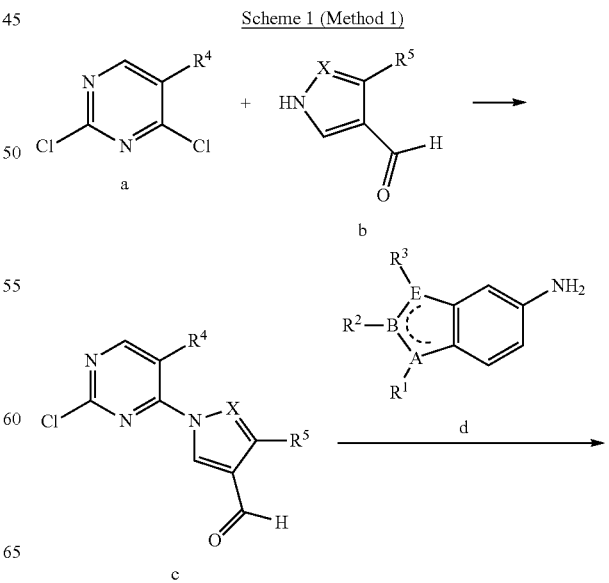

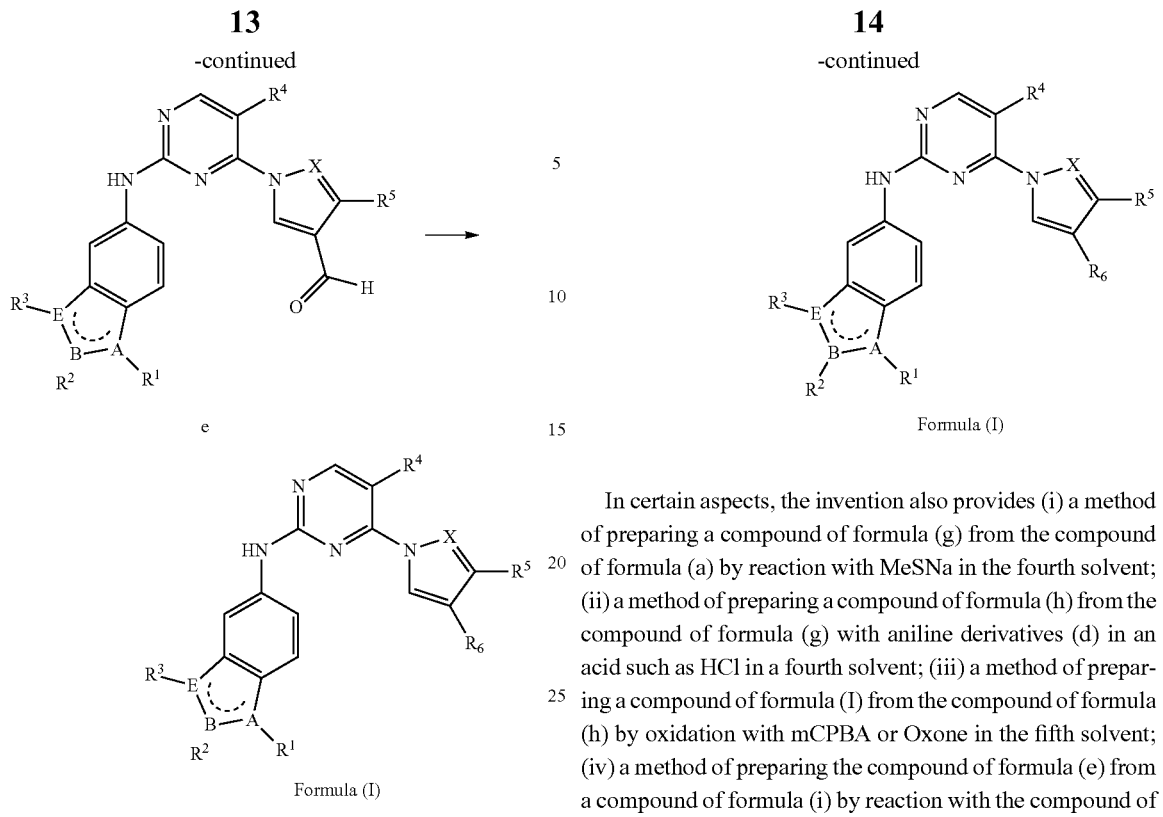

In certain aspects, the invention also provides (i) a method of preparing a compound of formula (f) by reductive amination of the compound of formula (c) and an amine derivative (R$_6$) in the presence of a reducing agent in the third solvent (see Scheme 2); (ii) a method of preparing the compound of Formula (I) by reaction of the compound of formula (f) with aniline derivatives (d) in the presence of the second base in the second solvent, a ligand, a palladium catalyst in the second organic solvent (see Scheme 2). The invention also provides a method of preparing a compound of Formula (I) according to Scheme 2 (Method 2).

In certain aspects, the invention also provides (i) a method of preparing a compound of formula (g) from the compound of formula (a) by reaction with MeSNa in the fourth solvent; (ii) a method of preparing a compound of formula (h) from the compound of formula (g) with aniline derivatives (d) in an acid such as HCl in a fourth solvent; (iii) a method of preparing a compound of formula (I) from the compound of formula (h) by oxidation with mCPBA or Oxone in the fifth solvent; (iv) a method of preparing the compound of formula (e) from a compound of formula (i) by reaction with the compound of formula (b) in the presence of a third base in the first solvent; and (v) a method of preparing a compound of Formula (I) by reductive amination of the compound of formula (e) with an amine derivative (R$^6$) in the presence of reducing agent in the third solvent, Scheme 3. The invention also provides a method of preparing a compound of Formula (I) according to Scheme 3 (Method 3).

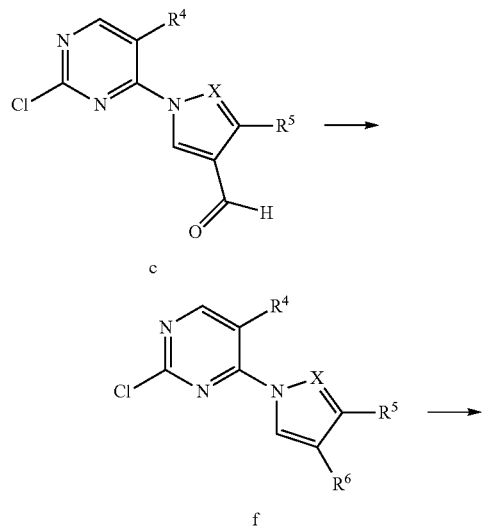

Scheme 2 (Method 2)

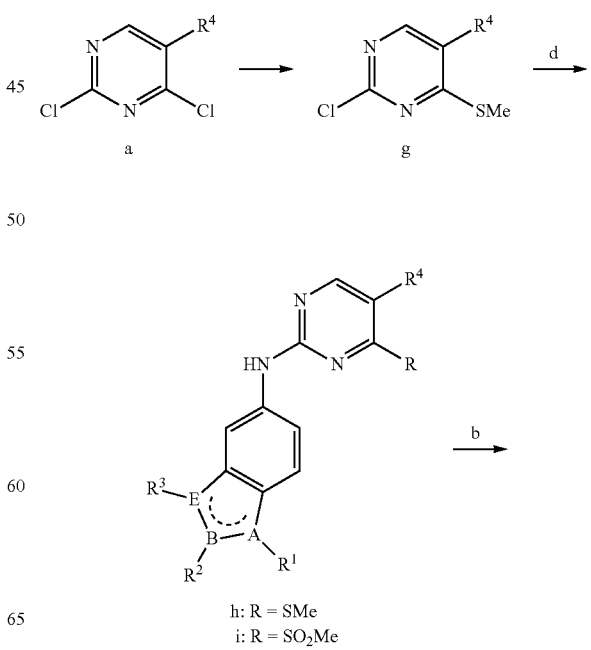

Scheme 3 (Method 3)

-continued

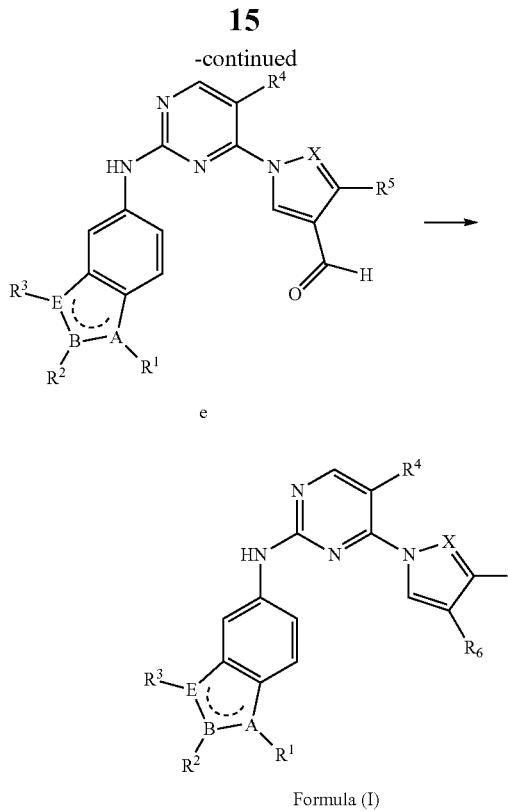

e

Formula (I)

With reference to Methods 1-3, while appropriate reaction solvents can be selected by one of ordinary skill in the art, the first organic solvent is generally selected from relatively polar, aprotic solvents such as acetone, tetrahydrofuran, N,N-dimethylformamide, dichloromethane, dichloroethane, or acetonitrile; the second organic solvent is generally selected from aprotic solvents such as toluene, dioxane, tetrahydrofuran, N,N-dimethylformamide, N,N-dimethylacetamide or N-methylmorpholine; the third organic solvent is generally selected from relatively polar, solvents such as tetrahydrofuran, methanol, ethanol, dichloromethane, dichloroethane, N,N-dimethylacetamide or N,N-dimethylformamide; the fourth solvent is generally selected from relatively polar, protic solvents such as methanol, ethanol, tert-butanol or water, and fifth solvent is generally selected from solvents such as dichloromethane, ethyl acetate, acetone, or water.

With reference to Methods 1-3, while bases and other reactants can be selected by one of ordinary skill in the art, the first base is generally selected from bases such as $K_2CO_3$, $Cs_2CO_3$, NaOH, KOH, NaH, tert-BuOK, ter-BuONa, triethylamine, or diisopropylethylamine; the second base is generally selected from bases such as tert-BuOK, tert-BuONa, $Cs_2CO_3$, or $K_2CO_3$; the third base is selected generally from bases such as NaH, n-BuLi, $Cs_2CO_3$; a palladium catalyst is generally selected from $Pd(OAc)_2$, $Pd_2(dba)_3$, or $Pd(dppf)Cl_2$; a ligand is generally selected from BiNap, Xantphose, or S-Phose; the oxidizing agent is selected from oxidizing agents such as m-chloroperbenzoic acid (mCPBA) or oxone; and the reducing agent is generally selected from $NaBH(OAc)_3$, $NaBH_4$, or $NaBH(CN)_3$.

In certain embodiments, the invention provides a method for preparing a compound of Formula (I), the method comprising reacting a compound of formula (f)

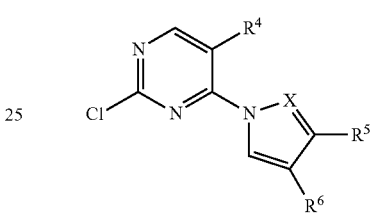

f in which $R^4$, $R^5$, $R^6$ and X are as defined in Formula (I), with an aniline derivative of formula (d)

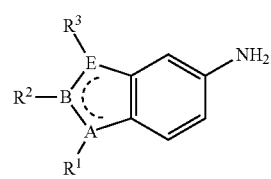

d in which A, B, E, $R^1$, $R^2$, and $R^3$ are as defined in Formula (I), in the presence of a base and a palladium catalyst under conditions such that a compound of Formula I is prepared.

Representative compounds of Formula (I) are listed below in Table 1.

TABLE 1

| | | | Representative compounds of Formula (I) | | | | | | | |
|---|---|---|---|---|---|---|---|---|---|---|
| No. | $R_1$ | $R_2$ | $R_3$ | $R_4$ | $R_5$ | $R_6$ | A | B | E | X |
| 1 | $CH_3$ | H | H | H | $CH_3$ | azetidine-OH | N | C | C | N |
| 2 | $CH_3$ | $CH_3$ | Cl | H | $CH_3$ | azetidine-OH | N | C | C | N |

TABLE 1-continued
Representative compounds of Formula (I)
| No. | R₁ | R₂ | R₃ | R₄ | R₅ | R₆ | A | B | E | X |
|---|---|---|---|---|---|---|---|---|---|---|
| 3 | CH₃ | CH₃ | H | H | CH₃ | 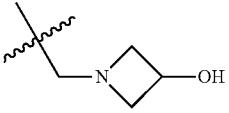 [SMILES: *CN1CC(O)C1] | N | C | C | N |
| 4 | CH₂CH₃ | H | H | H | CH₃ | 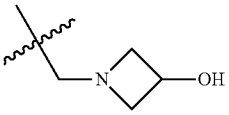 [SMILES: *CN1CC(O)C1] | N | C | C | N |
| 5 | CH₃ | H | Cl | H | CH₃ | 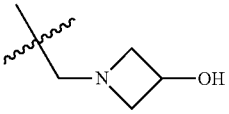 | N | C | C | N |
| 6 | iso-Pr | H | H | H | CH₃ | 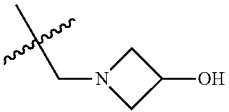 [SMILES: *CN1CC(O)C1] | N | C | C | CH |
| 7 | 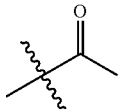 [SMILES: *C(C)=O] | H | H | H | CH₃ | 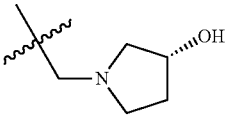 [SMILES: *CN1CC[C@@H](O)C1] | N | C | C | N |
| 8 | CH₃ | CH₃ | CH₃ | H | CH₃ | 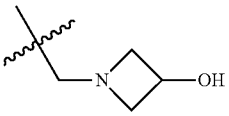 | N | C | C | N |
| 9 | iso-Pr | CH₃ | CH₃ | H | CH₃ | 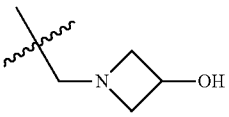 [SMILES: *CN1CC(O)C1] | N | C | C | N |
| 10 | CH₃ | H | Br | H | CH₃ | 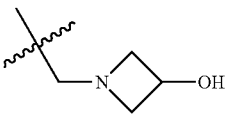 [SMILES: *CN1CC(O)C1] | N | C | C | N |
| 11 | 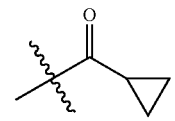 [SMILES: *C(=O)C1CC1] | H | H | H | CH₃ | 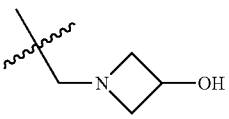 | N | C | C | N |
| 12 | 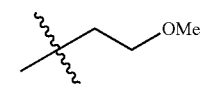 [SMILES: *CCOC] | H | H | H | CH₃ | 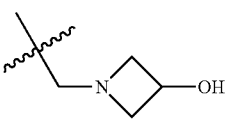 [SMILES: *CN1CC(O)C1] | N | C | C | N |
| 13 | 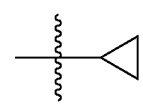 [SMILES: *C1CC1] | H | Cl | H | CH₃ | 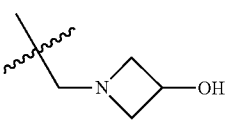 [SMILES: *CN1CC(O)C1] | N | C | C | N |

TABLE 1-continued
Representative compounds of Formula (I)
| No. | R₁ | R₂ | R₃ | R₄ | R₅ | R₆ | A | B | E | X |
|---|---|---|---|---|---|---|---|---|---|---|
| 14 | iso-Pr | H |  | H | CH₃ | 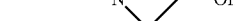 | N | C | C | N |
| 15 | CH₃ | H |  | H | CH₃ | 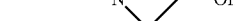 | N | C | C | N |
| 16 | CH₃ | H |  | H | CH₃ | 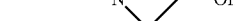 | N | C | C | N |
| 17 |  | H | H | H | CH₃ | 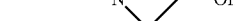 | N | C | C | N |
| 18 | CH₃ | H |  | H | CH₃ | 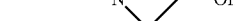 | N | C | C | N |
| 19 | CH₃ | H |  | H | CH₃ | 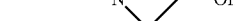 | N | C | C | N |
| 20 | CH₃ | H |  | H | CH₃ | 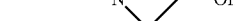 | N | C | C | N |
| 21 | CH₃ | CH₃ | Br | H | CH₃ | 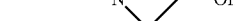 | N | C | C | N |
| 22 | CH₃ | CH₃ | Cl | H | CH₃ | 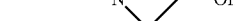 | N | C | C | N |
| 23 | CH₃ | H |  | H | CH₃ | 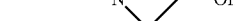 | N | C | C | N |
| 24 | CH₃ | H |  | H | CH₃ | 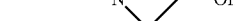 | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 25 | methylsulfonyl-dimethyl | H | Cl | H | CH₃ | CH₂-(3-hydroxyazetidin-1-yl) | N | C | C | N |
| 26 | CH₃ | H | pyrrolidinyl-sulfonyl | H | CH₃ | CH₂-(3-hydroxyazetidin-1-yl) | N | C | C | N |
| 27 | CH₃ | H | methylsulfonyl | H | CH₃ | CH₂-(3-hydroxyazetidin-1-yl) | N | C | C | N |
| 28 | CH₃ | — | H | H | CH₃ | CH₂-(3-hydroxyazetidin-1-yl) | N | N | C | N |
| 29 | CH₃ | — | H | H | CH₃ | CH₂-(3-hydroxyazetidin-1-yl) | N | N | C | CH |
| 30 | CH₃ | — | H | H | CH₃ | CH₂-((3S)-3-hydroxypyrrolidin-1-yl) | N | N | C | N |
| 31 | iso-Pr | — | H | H | CH₃ | CH₂-(3-hydroxyazetidin-1-yl) | N | N | C | N |
| 32 | CH₃ | — | Cl | H | CH₃ | CH₂-(3-hydroxyazetidin-1-yl) | N | N | C | N |
| 33 | cyclopropylmethyl | — | H | H | CH₃ | CH₂-(3-hydroxyazetidin-1-yl) | N | N | C | N |
| 34 | (tetrahydropyran-2-yl)methyl | — | H | H | CH₃ | CH₂-(3-hydroxyazetidin-1-yl) | N | N | C | N |
| 35 | iso-Pr | — | Cl | H | CH₃ | CH₂-(3-hydroxyazetidin-1-yl) | N | N | C | N |

TABLE 1-continued
Representative compounds of Formula (I)
| No. | R₁ | R₂ | R₃ | R₄ | R₅ | R₆ | A | B | E | X |
|---|---|---|---|---|---|---|---|---|---|---|
| 36 | 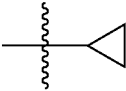 [SMILES: *C1CC1] | — | Cl | H | CH₃ | 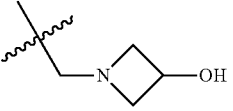 [SMILES: *CN1CC(O)C1] | N | N | C | N |
| 37 | CH₃ | — | 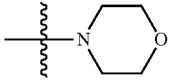 | H | CH3 | 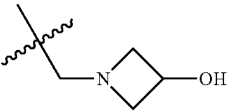 | N | N | C | N |
| 38 | CH₃ | — | 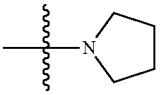 | H | CH₃ | 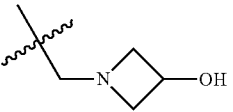 [SMILES: *CN1CC(O)C1] | N | N | C | N |
| 39 | 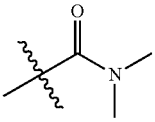 [SMILES: *C(=O)N(C)C] | — | Cl | H | CH₃ | 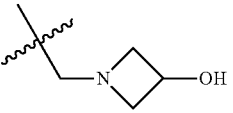 | N | N | C | N |
| 40 | CH₃ | — | 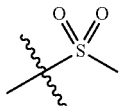 [SMILES: *S(C)(=O)=O] | H | CH₃ | 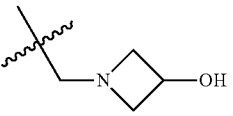 [SMILES: *CN1CC(O)C1] | N | N | C | N |
| 41 | CH₃ | H | H | H | CH₃ | 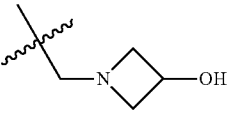 [SMILES: *CN1CC(O)C1] | N | CH | CH | N |
| 42 | iso-Pr | H | H | H | CH₃ | 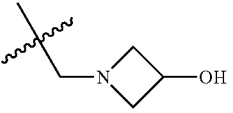 [SMILES: *CN1CC(O)C1] | N | CH | CH | N |
| 43 | 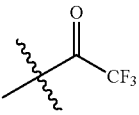 [SMILES: *C(=O)C(F)(F)F] | H | H | H | CH₃ | 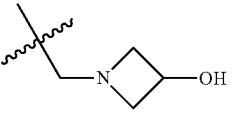 [SMILES: *CN1CC(O)C1] | N | CH | CH | N |
| 44 | 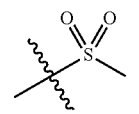 [SMILES: *S(C)(=O)=O] | H | H | H | CH₃ | 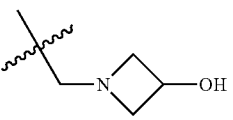 | N | CH | CH | N |
| 45 | H | H | H | H | CH₃ | 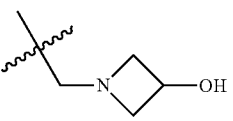 | CH | CH | CH | N |
| 46 | CH₃ | H | 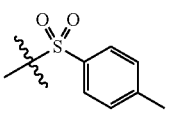 [SMILES: *S(=O)(=O)c1ccc(C)cc1] | H | CH₃ | 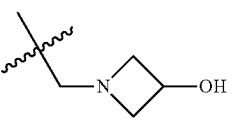 | N | C | C | N |

TABLE 1-continued
Representative compounds of Formula (I)
| No. | R₁ | R₂ | R₃ | R₄ | R₅ | R₆ | A | B | E | X |
|---|---|---|---|---|---|---|---|---|---|---|
| 47 | CH₃ | H | 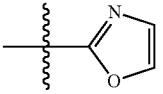 | H | CH₃ | 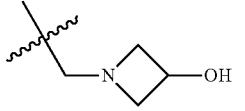 [SMILES: *CN1CC(O)C1] | N | C | C | N |
| 48 | — | CH₃ | Cl | H | CH₃ | 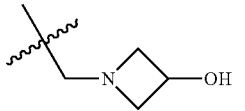 | O | C | C | N |
| 49 | — | CH₃ | H | H | CH₃ | 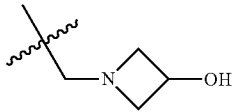 [SMILES: *CN1CC(O)C1] | O | C | C | N |
| 50 | CH₃ | H | H | F | CH₃ | 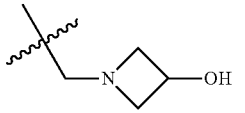 | N | C | C | CH |
| 51 | iso-Pr | H | H | F | CH₃ | 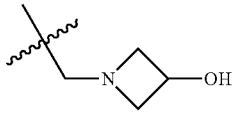 | N | C | C | N |
| 52 | CH₃ | — | H | F | CH₃ | 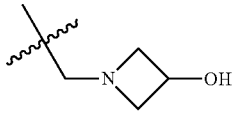 [SMILES: *CN1CC(O)C1] | N | N | C | N |
| 53 | iso-Pr | H | H | F | CH₃ | 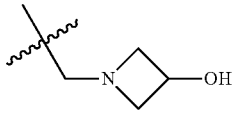 [SMILES: *CN1CC(O)C1] | N | C | C | CH |
| 54 | CH₃ | CH₃ | Cl | F | CH₃ | 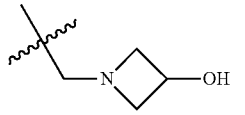 [SMILES: *CN1CC(O)C1] | N | C | C | CH |
| 55 | CH₃ | H | H | H | 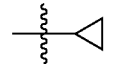 | 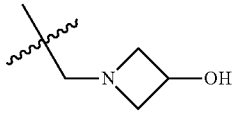 | N | C | C | N |
| 56 | CH₂CH₃ | H | H | H | 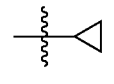 | 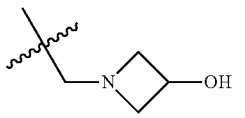 | N | C | C | N |
| 57 | iso-Pr | H | H | H | 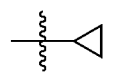 | 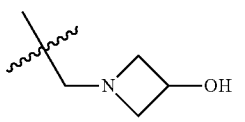 [SMILES: *CN1CC(O)C1] | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 58 | H | H | H | H | cyclopropyl | azetidine-3-OH (via CH₂) | CH | CH | CH | N |
| 59 | CH₃ | H | H | H | cyclopropyl | azetidine-3-OH (via CH₂) | N | CH | CH | N |
| 60 | H | — | H | H | cyclopropyl | azetidine-3-OH (via CH₂) | CH | N | N | N |
| 61 | — | H | — | H | cyclopropyl | azetidine-3-OH (via CH₂) | N | C | S | N |
| 62 | CH₃ | — | H | H | CH₃ | azetidin-3-yl pivalate (via CH₂) | N | N | C | N |
| 63 | CH₃ | — | H | H | CH₃ | azetidin-3-yl 2-ethylbutanoate (via CH₂) | N | N | C | N |
| 64 | CH₃ | H | thiazol-2-yl | H | CH₃ | azetidine-3-OH (via CH₂) | N | C | C | N |
| 65 | CH₃ | — | H | H | CH₃ | azetidine-3-OMe (via CH₂) | N | N | C | N |
| 66 | CH₃ | — | H | H | CH₃ | azetidine-3-CO₂Me (via CH₂) | N | N | C | N |
| 67 | CH₃ | — | H | CH₃ | CH₃ | azetidine-3-OH (via CH₂) | N | N | C | N |
| 68 | CH₃ | — | H | CF₃ | CH₃ | azetidine-3-OH (via CH₂) | N | N | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 69 | CH₃ | — | H | Br | CH₃ | azetidine-N-CH₂- with 3-OH | N | N | C | N |
| 70 | CH₃ | — | H | H | CH₃ | azetidine-N-CH₂- with 3-CO₂H | N | N | C | N |
| 71 | CH₃ | — | H | H | CH₃ | -CH₂-N(CH₃)₂ | N | N | C | N |
| 72 | CH₃ | — | H | H | CH₃ | piperidine-N-CH₂- with 4-OH | N | N | C | N |
| 73 | CH₃ | — | H | H | CH₃ | pyrrolidine-N-CH₂- with 3,4-diOH | N | N | C | N |
| 74 | CH₃ | — | H | H | CH₃ | pyrrolidine-N-CH₂- with 3-NH₂ | N | N | C | N |
| 75 | CH₃ | — | H | H | CH₃ | pyrrolidine-N-CH₂- with 3-NHC(O)NH₂ | N | N | C | N |
| 76 | -CH₂CH₂OH | H | H | H | CH₃ | azetidine-N-CH₂- with 3-OH | N | C | C | N |
| 77 | pyrrolidine-N-CH₂CH₂- | H | H | H | CH₃ | azetidine-N-CH₂- with 3-OH | N | C | C | N |
| 78 | morpholine-N-CH₂CH₂- | H | H | H | CH₃ | azetidine-N-CH₂- with 3-OH | N | C | C | N |
| 79 | CH₃ | CH₃ | CF₃ | H | CH₃ | azetidine-N-CH₂- with 3-OH | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 80 | CH₃ | CF₃ | CH₃ | H | CH₃ | azetidin-3-ol-CH₂- | N | C | C | N |
| 81 | CH₃ | H | CN | H | CH₃ | azetidin-3-ol-CH₂- | N | C | C | N |
| 82 | CH₃ | H | cyclopropyl | H | CH₃ | azetidin-3-ol-CH₂- | N | C | C | N |
| 83 | CH₃ | H | furan-3-yl | H | CH₃ | azetidin-3-ol-CH₂- | N | C | C | N |
| 84 | CH₃ | H | pyridin-3-yl | H | CH₃ | azetidin-3-ol-CH₂- | N | C | C | N |
| 85 | cyclopropyl-CH₂- | H | H | H | CH₃ | azetidin-3-ol-CH₂- | N | C | C | N |
| 86 | cyclobutyl | H | H | H | CH₃ | azetidin-3-ol-CH₂- | N | C | C | N |
| 87 | CH₃ | — | OMe | H | CH₃ | azetidin-3-ol-CH₂- | N | N | C | N |
| 88 | CH₃ | H | Cl | H | CH₃ | azetidin-3-ol-CH₂-, HCl | N | C | C | N |
| 89 | CH₃ | H | Cl | H | CH₃ | azetidin-3-ol-CH₂-, MsOH | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 90 | CH₃ | — | Cl | F | CH₃ | azetidine-3-ol (CH₂-linked) | N | N | C | CH |
| 91 | iso-Pr | — | Cl | F | CH₃ | azetidine-3-ol (CH₂-linked) | N | N | C | CH |
| 92 | — | iso-Pr | Cl | F | CH₃ | azetidine-3-ol (CH₂-linked) | N | N | C | CH |
| 93 | CH₃ | CH₃ | Cl | Me | CH₃ | azetidine-3-ol (CH₂-linked) | N | C | C | CH |
| 94 | CH₃ | H | Cl | H | CH₃ | (3R)-pyrrolidin-3-ol (CH₂-linked) | N | C | C | N |
| 95 | cyclopropyl (CH-linked) | H | Cl | H | CH₃ | (3R)-pyrrolidin-3-ol (CH₂-linked) | N | C | C | N |
| 96 | CH₃ | CH₃ | Br | H | CH₃ | (3R)-pyrrolidin-3-ol (CH₂-linked) | N | C | C | N |
| 97 | CH₃ | H | C(O)-cyclopropyl | H | CH₃ | (3R)-pyrrolidin-3-ol (CH₂-linked) | N | C | C | N |
| 98 | CH₃ | H | C(O)-cyclopropyl | H | CH₃ | (3R)-piperidin-3-ol (CH₂-linked) | N | C | C | N |
| 99 | CH₃ | CH₃ | Cl | H | CH₃ | (3R)-piperidin-3-ol (CH₂-linked) | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 100 | CH₃ | H | Cl | H | CH₃ | 3-hydroxypiperidin-1-ylmethyl | N | C | C | N |
| 101 | CH₃ | CH₃ | Cl | H | CH₃ | (3R)-3-hydroxypyrrolidin-1-ylmethyl | N | C | C | N |
| 102 | cyclopropyl | H | Cl | H | CH₃ | (3R)-3-hydroxypyrrolidin-1-ylmethyl | N | C | C | N |
| 103 | cyclopropyl | H | Cl | H | CH₃ | 3-hydroxyazetidin-1-ylcarbonyl | N | C | C | N |
| 104 | CH₃ | CH₃ | Cl | H | CH₃ | piperazin-1-ylmethyl | N | C | C | N |
| 105 | CH₃ | H | C(CH₃)(CF₃)=O | H | CH₃ | (3R)-3-hydroxypyrrolidin-1-ylmethyl | N | CH | C | N |
| 106 | H | H | C(CH₃)₂C(=O)CH₃ | H | CH₃ | (3R,4R)-3,4-dihydroxypyrrolidin-1-ylmethyl | N | C | C | N |
| 107 | H | H | C(CH₃)₂C(=O)CH₃ | H | CH₃ | (3R)-3-hydroxypyrrolidin-1-ylmethyl | N | C | C | N |
| 108 | H | H | C(CH₃)₂C(=O)CH₃ | H | CH₃ | 3-hydroxyazetidin-1-ylmethyl | N | C | C | N |
| 109 | H | H | C(CH₃)₂C(=O)CF₃ | H | CH₃ | (3R,4R)-3,4-dihydroxypyrrolidin-1-ylmethyl | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 110 | H | H | C(O)CF₃ (with methyl) | H | CH₃ | CH₂-N-pyrrolidinyl-3-OH | N | C | C | N |
| 111 | H | H | C(O)CF₃ (with methyl) | H | CH₃ | CH₂-N-pyrrolidinyl-4-OH, 2-CH₂OH | N | C | C | N |
| 112 | CH₃ | H | C(O)CF₃ (with methyl) | H | CH₃ | CH₂-N-pyrrolidinyl-3,4-diOH | N | C | C | N |
| 113 | CH₃ | H | C(O)CF₃ (with methyl) | H | CH₃ | CH₂-N-pyrrolidinyl-3-OH, 4-OMe | N | C | C | N |
| 114 | CH₃ | H | C(O)CF₃ (with methyl) | H | CH₃ | CH₂-N-pyrrolidinyl-4-OH, 2-CH₂OH | N | C | C | N |
| 115 | CH₃ | H | C(O)cyclopropyl (with methyl) | H | CH₃ | CH₂-N-pyrrolidinyl-3,4-diOH | N | C | C | N |
| 116 | CH₃ | H | C(O)cyclopropyl (with methyl) | H | CH₃ | CH₂-N-pyrrolidinyl-3-OH, 4-OMe | N | C | C | N |
| 117 | CH₃ | H | C(O)cyclopropyl (with methyl) | H | CH₃ | CH₂-N-pyrrolidinyl-3,4-diOH | N | C | C | N |
| 118 | CH₃ | H | C(O)cyclopropyl (with methyl) | H | CH₃ | CH₂-N-pyrrolidinyl-3,4-diOAc | N | C | C | N |

TABLE 1-continued
Representative compounds of Formula (I)
| No. | R₁ | R₂ | R₃ | R₄ | R₅ | R₆ | A | B | E | X |
|---|---|---|---|---|---|---|---|---|---|---|
| 119 | H | H | 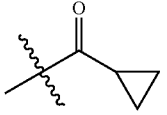 [SMILES: *C(=O)C1CC1] | H | CH₃ | 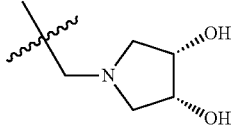 [SMILES: *CN1C[C@@H](O)[C@@H](O)C1] | N | C | C | N |
| 120 | H | H | 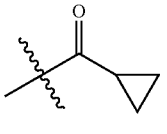 | H | CH₃ | 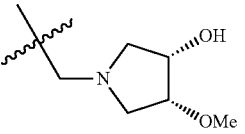 [SMILES: *CN1C[C@H](O)[C@H](OC)C1] | N | C | C | N |
| 121 | H | H | 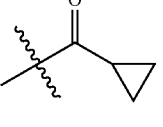 | H | CH₃ | 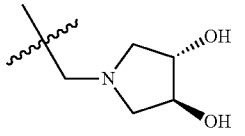 [SMILES: *CN1C[C@H](O)[C@@H](O)C1] | N | C | C | N |
| 122 | H | H | 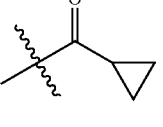 | H | CH₃ | 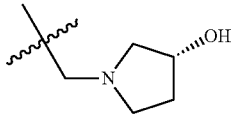 [SMILES: *CN1CC[C@@H](O)C1] | N | C | C | N |
| 123 | H | H | 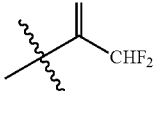 | H | CH₃ | 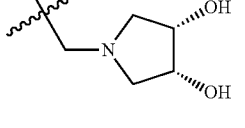 | N | C | C | N |
| 124 | H | H | 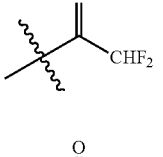 | H | CH₃ | 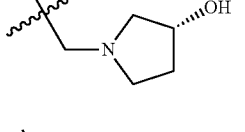 | N | C | C | N |
| 125 | H | H | 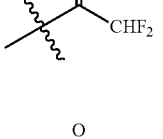 | H | CH₃ | 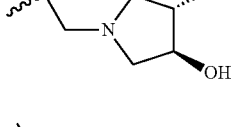 | N | C | C | N |
| 126 | H | H | 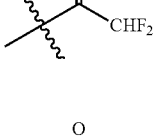 | H | CH₃ | 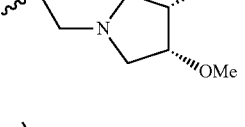 | N | C | C | N |
| 127 | CH₃ | H | 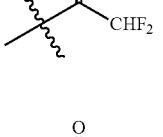 | H | CH₃ | 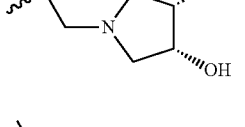 | N | C | C | N |
| 128 | CH₃ | H | 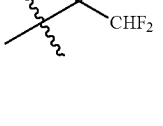 | H | CH₃ | 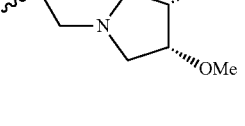 | N | C | C | N |

TABLE 1-continued
Representative compounds of Formula (I)
| No. | R$_1$ | R$_2$ | R$_3$ | R$_4$ | R$_5$ | R$_6$ | A | B | E | X |
|---|---|---|---|---|---|---|---|---|---|---|
| 129 | CH$_3$ | H | 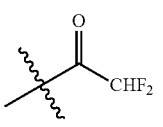 | H | CH$_3$ | 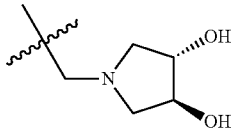 [SMILES: *CN1C[C@H](O)[C@@H](O)C1] | N | C | C | N |
| 130 | CH$_3$ | H | 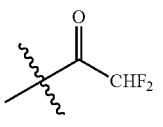 | H | CH$_3$ | 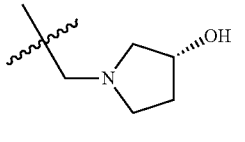 [SMILES: *CN1CC[C@@H](O)C1] | N | C | C | N |
| 131 | CH$_3$ | H | 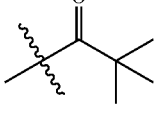 | H | CH$_3$ | 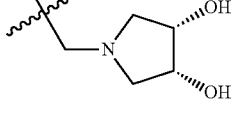 | N | C | C | N |
| 132 | CH$_3$ | H | 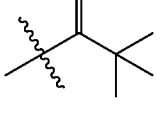 | H | CH$_3$ | 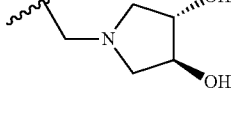 | N | C | C | N |
| 133 | CH$_3$ | H | 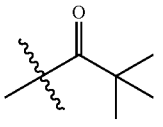 [SMILES: *C(=O)C(C)(C)C] | H | CH$_3$ | 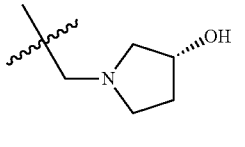 [SMILES: *CN1CC[C@@H](O)C1] | N | C | C | N |
| 134 | 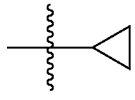 | H | 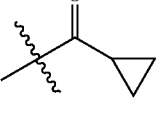 | H | CH$_3$ | 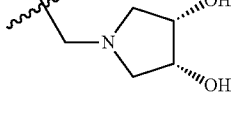 | N | C | C | N |
| 135 | 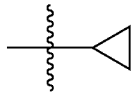 | H | 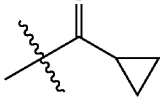 | H | CH$_3$ | 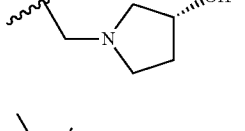 | N | C | C | N |
| 136 | 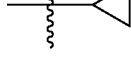 | H | 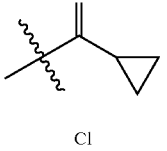 | H | CH$_3$ | 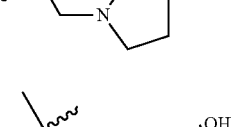 | N | C | C | N |
| 137 | CH$_3$ | CH$_3$ | Cl | H | CH$_3$ | 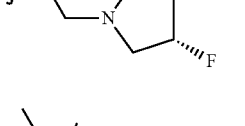 | N | C | C | N |
| 138 | CH$_3$ | CH$_3$ | Cl | H | CH$_3$ | 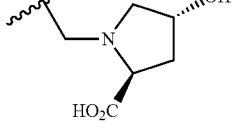 | N | C | C | N |

TABLE 1-continued

Representative compounds of Formula (I)

| No. | R₁ | R₂ | R₃ | R₄ | R₅ | R₆ | A | B | E | X |
|-----|-----|-----|-----|-----|-----|-----|---|---|---|---|
| 139 | CH₃ | CH₃ | Cl | H | CH₃ | *N-methylpyrrolidin-3-ol with dimethylamino* | N | C | C | N |
| 140 | CH₃ | CH₃ | Cl | H | CH₃ | *N-ethyl-2-methyl-aminopropanol* | N | C | C | N |
| 141 | CH₃ | CH₃ | Cl | H | CH₃ | *3-methoxyazetidine* | N | C | C | N |
| 142 | CH₃ | CH₃ | Cl | H | CH₃ | *4-hydroxy-2-(methoxymethyl)pyrrolidine* | N | C | C | N |
| 143 | CH₃ | H | *isopropyl ketone* | H | CH₃ | *3,4-dihydroxypyrrolidine* | N | C | C | N |
| 144 | CH₃ | H | *isopropyl ketone* | H | CH₃ | *3,4-dihydroxypyrrolidine* | N | C | C | N |
| 145 | CH₃ | H | *isopropyl ketone* | H | CH₃ | *3-hydroxypyrrolidine* | N | C | C | N |
| 146 | CH₃ | H | *isopropyl ketone* | H | CH₃ | *3-hydroxy-4-methoxypyrrolidine* | N | C | C | N |
| 147 | CH₃ | CH₃ | Cl | H | CH₃ | *3-hydroxypyrrolidine (ethylene linker)* | N | C | C | N |
| 148 | CH₃ | CH₃ | Cl | H | CH₃ | *3-hydroxyazetidine (ethylene linker)* | N | C | C | N |

TABLE 1-continued
Representative compounds of Formula (I)
| No. | R₁ | R₂ | R₃ | R₄ | R₅ | R₆ | A | B | E | X |
|---|---|---|---|---|---|---|---|---|---|---|
| 149 | CH₃ | CH₃ | Cl | H | CH₃ | 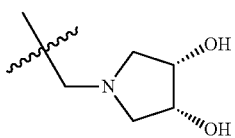 [SMILES: *CN1C[C@@H](O)[C@@H](O)C1] | N | C | C | N |
| 150 | CH₃ | CH₃ | Cl | H | CH₃ | 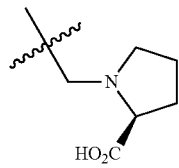 [SMILES: *CN1CCC[C@H]1C(=O)O] | N | C | C | N |
| 151 | CH₃ | CH₃ | Cl | H | CH₃ | 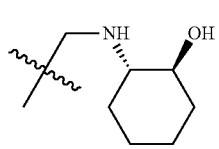 [SMILES: *CN[C@H]1CCCC[C@@H]1O] | N | C | C | N |
| 152 | CH₃ | CH₃ | Cl | H | CH₃ | 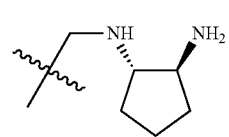 [SMILES: *CN[C@H]1CCC[C@@H]1N] | N | C | C | N |
| 153 | CH₃ | CH₃ | Cl | H | CH₃ | 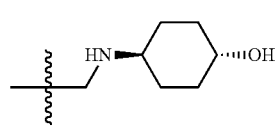 | N | C | C | N |
| 154 | CH₃ | CH₃ | Cl | H | CH₃ | 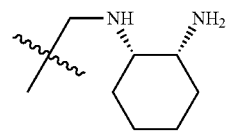 [SMILES: *CN[C@H]1CCCC[C@H]1N] | N | C | C | N |
| 155 | CH₃ | CH₃ | Cl | H | CH₃ | 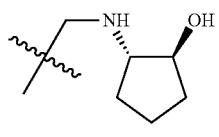 | N | C | C | N |
| 156 | CH₃ | CH₃ | Cl | H | CH₃ | 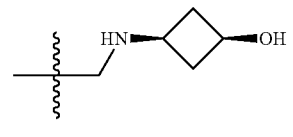 [SMILES: *CN[C@H]1C[C@@H](O)C1] | N | C | C | N |
| 157 | CH₃ | CH₃ | Cl | H | CH₃ | 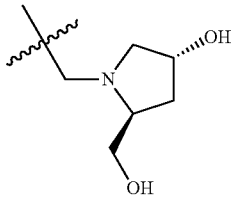 [SMILES: *CN1C[C@H](O)C[C@H]1CO] | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 158 | CH₃ | CH₃ | Cl | H | CH₃ | pyrrolidine with OH and OMe | N | C | C | N |
| 159 | CH₃ | CH₃ | Cl | H | CH₃ | pyrrolidine with OH and O-iPr | N | C | C | N |
| 160 | CH₃ | CH₃ | Cl | H | CH₃ | pyrrolidine with OMe and OMe | N | C | C | N |
| 161 | CH₃ | CH₃ | Cl | H | CH₃ | pyrrolidine with OH and CH₃ | N | C | C | N |
| 162 | CH₃ | — | methylsulfonyl-C(CH₃)₂ | H | CH₃ | pyrrolidine with OH and OH | N | N | C | N |
| 163 | CH₃ | — | methylsulfonyl-C(CH₃)₂ | H | CH₃ | pyrrolidine with OH and OMe | N | N | C | N |
| 164 | CH₃ | CH₃ | Br | H | CH₃ | pyrrolidine with OH and OH | N | C | C | N |
| 165 | n-Pr | CH₃ | Cl | H | CH₃ | azetidine with OH | N | C | C | N |
| 166 | n-Pr | CH₃ | Cl | H | CH₃ | pyrrolidine with OH and OH | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 167 | n-Pr | CH₃ | Cl | H | CH₃ | pyrrolidine with OH and CH₂OH | N | C | C | N |
| 168 | CH₃ | CH₃ | C(O)-cyclopropyl | H | CH₃ | 3,4-dihydroxypyrrolidine | N | C | C | N |
| 169 | CH₃ | CH₃ | C(O)-cyclopropyl | H | CH₃ | 3-hydroxyazetidine | N | C | C | N |
| 170 | CH(CH₂OMe)- | CH₃ | Br | H | CH₃ | 3-hydroxyazetidine | N | C | C | N |
| 171 | CH(CH₂OMe)- | CH₃ | Br | H | CH₃ | 3-hydroxypyrrolidine | N | C | C | N |
| 172 | CH(CH₂OMe)- | CH₃ | Br | H | CH₃ | 3,4-dihydroxypyrrolidine | N | C | C | N |
| 173 | CH₃ | H | SO₂CH₃ | H | CH₃ | 3,4-dihydroxypyrrolidine | N | C | C | N |
| 174 | CH(CH₂OH)- | CH₃ | Cl | H | CH₃ | 3,4-dihydroxypyrrolidine | N | C | C | N |
| 175 | CH₃ | H | SO₂CH₃ | H | CH₃ | pyrrolidine with OH and CH₂OH | N | C | C | N |

TABLE 1-continued

Representative compounds of Formula (I)

| No. | R₁ | R₂ | R₃ | R₄ | R₅ | R₆ | A | B | E | X |
|---|---|---|---|---|---|---|---|---|---|---|
| 176 | CH₃ | H | cyclopentyl | H | CH₃ | (3,4-dihydroxypyrrolidin-1-yl)methyl | N | C | C | N |

The compounds in Table 1 are named as follows:
1-((3-methyl-1-(2-(1-methyl-1H-indol-5-ylamino)pyrimidin-4-yl)-1H-pyrazol-4-yl)methyl)azetidin-3-ol,
1-((1-(2-(3-chloro-1,2-dimethyl-1H-indol-5-ylamino)pyrimidin-4-yl)-3-methyl-1H-pyrazol-4-yl)methyl)azetidin-3-ol,
1-((1-(2-(1,2-dimethyl-1H-indol-5-ylamino)pyrimidin-4-yl)-3-methyl-1H-pyrazol-4-yl)methyl)azetidin-3-ol,
1-((1-(2-(1-ethyl-1H-indol-5-ylamino)pyrimidin-4-yl)-3-methyl-1H-pyrazol-4-yl)methyl)azetidin-3-ol,
1-((1-(2-(3-chloro-1-methyl-1H-indol-5-ylamino)pyrimidin-4-yl)-3-methyl-1H-pyrazol-4-yl)methyl)azetidin-3-ol,
1-((1-(2-(1-isopropyl-1H-indol-5-ylamino)-pyrimidin-4-yl)-4-methyl-1H-pyrrol-3-yl)methyl)azetidin-3-ol,
1-(5-(6-(4-(((R)-3-hydroxypyrrolidin-1-yl)methyl)-3-methyl-1H-pyrazol-1-yl)-pyrimidin-2-ylamino)-1H-indol-1-yl)ethanone,
1-((3-methyl-1-(2-(1,2,3-trimethyl-1H-indol-5-ylamino)-pyrimidin-4-yl)-1H-pyrazol-4-yl)methyl)azetidin-3-ol,
1-((1-(2-(1-isopropyl-2,3-dimethyl-1H-indol-5-ylamino)-pyrimidin-4-yl)-3-methyl-1H-pyrazol-4-yl)methyl)azetidin-3-ol,
1-((1-(2-(3-bromo-1-methyl-1H-indol-5-ylamino)-pyrimidin-4-yl)-3-methyl-1H-pyrazol-4-yl)methyl)azetidin-3-ol,
cyclopropyl(5-(6-(4-((3-hydroxyazetidin-1-yl)methyl)-3-methyl-1H-pyrazol-1-yl)-pyrimidin-2-ylamino)-1H-indol-1-yl)methanone,
1-((1-(2-(1-(2-methoxyethyl)-1H-indol-5-ylamino)-pyrimidin-4-yl)-3-methyl-1H-pyrazol-4-yl)methyl)azetidin-3-ol,
1-((1-(2-(3-chloro-1-cyclopropyl-1H-indol-5-ylamino)-pyrimidin-4-yl)-3-methyl-1H-pyrazol-4-yl)methyl)azetidin-3-ol,
1-((1-(2-(1-isopropyl-3-(morpholinomethyl)-1H-indol-5-ylamino)-pyrimidin-4-yl)-3-methyl-1H-pyrazol-4-yl)methyl)azetidin-3-ol,
1-(5-(6-(4-((3-hydroxyazetidin-1-yl)methyl)-3-methyl-1H-pyrazol-1-yl)-pyrimidin-2-ylamino)-1-methyl-1H-indol-3-yl)-2,2,2-trifluoroethanone,
1-(5-(6-(4-((3-hydroxyazetidin-1-yl)methyl)-3-methyl-1H-pyrazol-1-yl)-pyrimidin-2-ylamino)-1-methyl-1H-indol-3-yl)ethanone,
1-((3-methyl-1-(2-(1-(methansulfonyl)-1H-indol-5-ylamino)-pyrimidin-4-yl)-1H-pyrazol-4-yl)methyl)azetidin-3-ol,
N,N-dimethyl 5-(6-(4-((3-hydroxyazetidin-1-yl)methyl)-3-methyl-1H-pyrazol-1-yl)-pyrimidin-2-ylamino)-1-methyl-1H-indole-3-carboxamide,
(5-(6-(4-((3-hydroxyazetidin-1-yl)methyl)-3-methyl-1H-pyrazol-1-yl)-1 pyrimidin-2-ylamino)-1-methyl-1H-indol-3-yl)(morpholino)methanone,
1-((3-methyl-1-(2-(1-methyl-3-(oxazol-5-yl)-1H-indol-5-ylamino)-pyrimidin-4-yl)-1H-pyrazol-4-yl)methyl)azetidin-3-ol,
1-((1-(2-(3-bromo-1,2-dimethyl-1H-indol-5-ylamino)-pyrimidin-4-yl)-3-methyl-1H-pyrazol-4-yl)methyl)azetidin-3-ol,
3-chloro-1,2-dimethyl-N-(6-(3-methyl-4-(pyrrolidin-1-ylmethyl)-1H-pyrazol-1-yl)-pyrimidin-2-yl)-1H-indol-5-amine,
(5-(6-(4-((3-hydroxyazetidin-1-yl)methyl)-3-methyl-1H-pyrazol-1-yl)-pyrimidin-2-ylamino)-1-methyl-1H-indol-3-yl)(pyrrolidin-1-yl)methanone, cyclopropyl(5-(6-(4-((3-hydroxyazetidin-1-yl)methyl)-3-methyl-1H-pyrazol-1-yl)-pyrimidin-2-ylamino)-1-methyl-1H-indol-3-yl)methanone,
1-((1-(2-(3-chloro-1-(methansulfonyl)-1H-indol-5-ylamino)-pyrimidin-4-yl)-3-methyl-1H-pyrazol-4-yl)methyl)azetidin-3-ol,
1-((3-methyl-1-(2-(1-methyl-3-(pyrrolidin-1-ylsulfonyl)-1H-indol-5-ylamino)-pyrimidin-4-yl)-1H-pyrazol-4-yl)methyl)azetidin-3-ol,
1-((3-methyl-1-(2-(1-methyl-3-(methansulfonyl)-1H-indol-5-ylamino)-pyrimidin-4-yl)-1H-pyrazol-4-yl)methyl)azetidin-3-ol,
1-((3-methyl-1-(2-(1-methyl-1H-indazol-5-ylamino)-pyrimidin-4-yl)-1H-pyrazol-4-yl)methyl)azetidin-3-ol,
1-((4-methyl-1-(2-(1-methyl-1H-indazol-5-ylamino)-pyrimidin-4-yl)-1H-pyrrol-3-yl)methyl)azetidin-3-ol,
(R)-1-((3-methyl-1-(2-(1-methyl-1H-indazol-5-ylamino)-pyrimidin-4-yl)-1H-pyrazol-4-yl)methyl)pyrrolidin-3-ol,
1-((1-(2-(1-isopropyl-1H-indazol-5-ylamino)-pyrimidin-4-yl)-3-methyl-1H-pyrazol-4-yl)methyl)azetidin-3-ol,
1-((1-(2-(3-chloro-1-methyl-1H-indazol-5-ylamino)-pyrimidin-4-yl)-3-methyl-1H-pyrazol-4-yl)methyl)azetidin-3-ol,
1-((1-(2-(1-cyclopropyl-1H-indazol-5-ylamino)-pyrimidin-4-yl)-3-methyl-1H-pyrazol-4-yl)methyl)azetidin-3-ol,
1-((3-methyl-1-(2-(1-(tetrahydro-1H-pyran-2-yl)-1H-indazol-5-ylamino)-pyrimidin-4-yl)-1H-pyrazol-4-yl)methyl)azetidin-3-ol,
1-((1-(2-(3-chloro-1-isopropyl-1H-indazol-5-ylamino)-pyrimidin-4-yl)-3-methyl-1H-pyrazol-4-yl)methyl)azetidin-3-ol,
1-((1-(2-(3-chloro-1-cyclopropyl-1H-indazol-5-ylamino)-pyrimidin-4-yl)-3-methyl-1H-pyrazol-4-yl)methyl)azetidin-3-ol,
1-((3-methyl-1-(2-(1-methyl-3-morpholino-1H-indazol-5-ylamino)-pyrimidin-4-yl)-1H-pyrazol-4-yl)methyl)azetidin-3-ol,
1-((3-methyl-1-(2-(1-methyl-3-(pyrrolidin-1-yl)-1H-indazol-5-ylamino)-pyrimidin-4-yl)-1H-pyrazol-4-yl)methyl)azetidin-3-ol, N,N-dimethyl 3-chloro-5-(6-(4-((3-hydroxyazetidin-1-yl)methyl)-3-methyl-1H-pyrazol-1-yl)-pyrimidin-2-ylamino)-1H-indazole-1-carboxamide,
1-((3-methyl-1-(2-(1-methyl-3-(methansulfonyl)-1H-indazol-5-ylamino)-pyrimidin-4-yl)-1H-pyrazol-4-yl)methyl)azetidin-3-ol,
1-((3-methyl-1-(2-(1-methylindolin-5-ylamino)-pyrimidin-4-yl)-1H-pyrazol-4-yl)methyl)azetidin-3-ol,
1-((1-(2-(1-isopropylindolin-5-ylamino)-pyrimidin-4-yl)-3-methyl-1H-pyrazol-4-yl)methyl)azetidin-3-ol,
1-(5-(6-(4-((3-hydroxyazetidin-1-yl)methyl)-3-methyl-1H-pyrazol-1-yl)-pyrimidin-2-ylamino)indolin-1-yl)-2,2,2-trifluoro-ethanone,
1-((3-methyl-1-(2-(1-(methansulfonyl)indolin-5-ylamino)-pyrimidin-4-yl)1H-pyrazol-4-yl)methyl)azetidin-3-ol,
1-((1-(2-(2,3-dihydro-1H-inden-5-ylamino)-pyrimidin-4-yl)-3-methyl-1H-pyrazol-4-yl)methyl)azetidin-3-ol,
1-((3-methyl-1-(2-(1-methyl-3-tosyl-1H-indol-5-ylamino)-pyrimidin-4-yl)-1H-pyrazol-4-yl)methyl)azetidin-3-ol,
1-((3-methyl-1-(2-(1-methyl-3-(oxazol-2-yl)-1H-indol-5-ylamino)-pyrimidin-4-yl)-1H-pyrazol-4-yl)methyl)azetidin-3-ol,
1-((1-(2-(3-chloro-2-methylbenzofuran-5-ylamino)-pyrimidin-4-yl)-3-methyl-1H-pyrazol-4-yl)methyl)azetidin-3-ol,
1-((3-methyl-1-(2-(2-methylbenzofuran-5-ylamino)-pyrimidin-4-yl)-1H-pyrazol-4-yl)methyl)azetidin-3-ol,
1-((1-(5-fluoro-2-(1-methyl-1H-indol-5-ylamino)-pyrimidin-4-yl)-4-methyl-1H-pyrrol-3-yl)methyl)azetidin-3-ol,
1-((1-(5-fluoro-2-(1-isopropyl-1H-indol-5-ylamino)-pyrimidin-4-yl)-3-methyl-1H-pyrazol-4-yl)methyl)azetidin-3-ol,
1-((1-(5-fluoro-2-(1-methyl-1H-indazol-5-ylamino)-pyrimidin-4-yl)-3-methyl-1H-pyrazol-4-yl)methyl)azetidin-3-ol,
1-((1-(5-fluoro-2-(1-isopropyl-1H-indazol-5-ylamino)-pyrimidin-4-yl)-4-methyl-1H-pyrrol-3-yl)methyl)azetidin-3-ol,
1-((1-(2-(3-chloro-1,2-dimethyl-1H-indol-5-ylamino)-5-fluoro-pyrimidin-4-yl)-4-methyl-1H-pyrrol-3-yl)methyl)azetidin-3-ol,
1-(3-cyclopropyl-1-(2-(1-methyl-1H-indol-5-ylamino)-pyrimidin-4-yl)-1H-pyrazol-4-yl)methyl)azetidin-3-ol,
1-((3-cyclopropyl-1-(2-(1-ethyl-1H-indol-5-ylamino)-pyrimidin-4-yl)-1H-pyrazol-4-yl)methyl)azetidin-3-ol,
1-((3-cyclopropyl-1-(2-(1-isopropyl-1H-indol-5-ylamino)-pyrimidin-4-yl)-1H-pyrazol-4-yl)methyl)azetidin-3-ol,
1-((3-cyclopropyl-1-(2-(2,3-dihydro-1H-inden-5-ylamino)-pyrimidin-4-yl)-1H-pyrazol-4-yl)methyl)azetidin-3-ol,
1-((3-cyclopropyl-1-(2-(1-methylindolin-5-ylamino)-pyrimidin-4-yl)-1H-pyrazol-4-yl)methyl)azetidin-3-ol,
1-((1-(2-(1H-indazol-6-ylamino)-pyrimidin-4-yl)-3-cyclopropyl-1H-pyrazol-4-yl)methyl)azetidin-3-ol,
1-((1-(2-(benzo[d]thiazol-6-ylamino)-pyrimidin-4-yl)-3-cyclopropyl-1H-pyrazol-4-yl)methyl)azetidin-3-ol,
1-((3-methyl-1-(2-(1-methyl-1H-indazol-5-ylamino)-pyrimidin-4-yl)-1H-pyrazol-4-yl)methyl)azetidin-3-yl pivalate,
1-((3-methyl-1-(2-(1-methyl-1H-indazol-5-ylamino)-pyrimidin-4-yl)-1H-pyrazol-4-yl)methyl)azetidin-3-yl 2-ethylbutanoate,
1-((3-methyl-1-(2-(1-methyl-3-(thiazol-2-yl)-1H-indol-5-ylamino)-pyrimidin-4-yl)-1H-pyrazol-4-yl)methyl)azetidin-3-ol,
N-(6-(4-((3-methoxyazetidin-1-yl)methyl)-3-methyl-1H-pyrazol-1-yl)-pyrimidin-2-yl)-1-methyl-1H-indazol-5-amine,
methyl 1-((3-methyl-1-(2-(1-methyl-1H-indazol-5-ylamino)-pyrimidin-4-yl)-1H-pyrazol-4-yl)methyl)azetidine-3-carboxylate,
1-((3-methyl-1-(5-methyl-2-(1-methyl-1H-indazol-5-ylamino)-pyrimidin-4-yl)-1H-pyrazol-4-yl)methyl)azetidin-3-ol,
1-((3-methyl-1-(2-(1-methyl-1H-indazol-5-ylamino)-5-(trifluoromethyl)-pyrimidin-4-yl)-1H-pyrazol-4-yl)methyl)azetidin-3-ol,
1-((1-(5-bromo-2-(1-methyl-1H-indazol-5-ylamino)-pyrimidin-4-yl)-3-methyl-1H-pyrazol-4-yl)methyl)azetidin-3-ol,
1-((3-methyl-1-(2-(1-methyl-1H-indazol-5-ylamino)-pyrimidin-4-yl)-1H-pyrazol-4-yl)methyl)azetidine-3-carboxylic acid,
N-(6-(4-((3-(dimethylamino)azetidin-1-yl)methyl)-3-methyl-1H-pyrazol-1-yl)-pyrimidin-2-yl)-1-methyl-1H-indazol-5-amine,
1-((3-methyl-1-(2-(1-methyl-1H-indazol-5-ylamino)-pyrimidin-4-yl)-1H-pyrazol-4-yl)methyl)piperidin-4-ol,
(3S,4S)-1-((3-methyl-1-(2-(1-methyl-1H-indazol-5-ylamino)-pyrimidin-4-yl)-1H-pyrazol-4-yl)methyl)pyrrolidine-3,4-diol,
N-(6-(4-(((R)-3-aminopyrrolidin-1-yl)methyl)-3-methyl-1H-pyrazol-1-yl)-pyrimidin-2-yl)-1-methyl-1H-indazol-5-amine,
1-((3R)-1-((3-methyl-1-(2-(1-methyl-1H-indazol-5-ylamino)-pyrimidin-4-yl)-1H-pyrazol-4-yl)methyl)pyrrolidin-3-yl)urea,
1-((1-(2-(1-(2-hydroxyethyl)-1H-indol-5-ylamino)-pyrimidin-4-yl)-3-methyl-1H-pyrazol-4-yl)methyl)azetidin-3-ol,
1-((3-methyl-1-(2-(1-(2-(pyrrolidin-1-yl)ethyl)-1H-indol-5-ylamino)-pyrimidin-4-yl)-1H-pyrazol-4-yl)methyl)azetidin-3-ol,
1-((3-methyl-1-(2-(1-(2-morpholinoethyl)-1H-indol-5-ylamino)-pyrimidin-4-yl)-1H-pyrazol-4-yl)methyl)azetidin-3-ol,
1-((1-(2-(1,2-dimethyl-3-(trifluoromethyl)-1H-indol-5-ylamino)-pyrimidin-4-yl)-3-methyl-1H-pyrazol-4-yl)methyl)azetidin-3-ol,
1-((1-(2-(1,3-dimethyl-2-(trifluoromethyl)-1H-indol-5-ylamino)-pyrimidin-4-yl)-3-methyl-1H-pyrazol-4-yl)methyl)azetidin-3-ol,
5-(6-(4-((3-hydroxyazetidin-1-yl)methyl)-3-methyl-1H-pyrazol-1-yl)-pyrimidin-2-ylamino)-1-methyl-1H-indole-3-carbonitrile,
1-((1-(2-(3-cyclopropyl-1-methyl-1H-indol-5-ylamino)-pyrimidin-4-yl)-3-methyl-1H-pyrazol-4-yl)methyl)azetidin-3-ol,
1-((1-(2-(3-(furan-3-yl)-1-methyl-1H-indol-5-ylamino)-pyrimidin-4-yl)-3-methyl-1H-pyrazol-4-yl)methyl)azetidin-3-ol,
1-((3-methyl-1-(2-(1-methyl-3-(pyridin-3-yl)-1H-indol-5-ylamino)-pyrimidin-4-yl)-1H-pyrazol-4-yl)methyl)azetidin-3-ol,
1-((1-(2-(1-(cyclopropylmethyl)-1H-indol-5-ylamino)-pyrimidin-4-yl)-3-methyl-1H-pyrazol-4-yl)methyl)azetidin-3-ol,
1-((1-(2-(1-cyclobutyl-1H-indol-5-ylamino)-pyrimidin-4-yl)-3-methyl-1H-pyrazol-4-yl)methyl)azetidin-3-ol,
1-((1-(2-(3-methoxy-1-methyl-1H-indazol-5-ylamino)-pyrimidin-4-yl)-3-methyl-1H-pyrazol-4-yl)methyl)azetidin-3-ol,
1-((1-(2-(3-chloro-1-methyl-1H-indol-5-ylamino)-pyrimidin-4-yl)-3-methyl-1H-pyrazol-4-yl)methyl)azetidin-3-ol hydrochloride, 1-((1-(2-(3-chloro-1-methyl-1H-indol-5-ylamino)-pyrimidin-4-yl)-3-methyl-1H-pyrazol-4-yl)methyl)azetidin-3-ol methanesulfonic acid,
1-((1-(2-(3-chloro-1-methyl-1H-indazol-5-ylamino)-5-fluoropyrimidin-4-yl)-4-methyl-1H-pyrrol-3-yl)methyl)azetidin-3-ol,
1-((1-(2-(3-chloro-1-isopropyl-1H-indazol-5-ylamino)-5-fluoropyrimidin-4-yl)-4-methyl-1H-pyrrol-3-yl)methyl)azetidin-3-ol,
1-((1-(2-(3-chloro-2-isopropyl-2H-indazol-5-ylamino)-5-fluoropyrimidin-4-yl)-4-methyl-1H-pyrrol-3-yl)methyl)azetidin-3-ol,
1-((1-(2-(3-chloro-1,2-dimethyl-1H-indol-5-ylamino)-5-methylpyrimidin-4-yl)-4-methyl-1H-pyrrol-3-yl)methyl)azetidin-3-ol,
(R)-1-((1-(2-(3-chloro-1-methyl-1H-indol-5-ylamino)pyrimidin-4-yl)-3-methyl-1H-pyrazol-4-yl)methyl)pyrrolidin-3-ol,
(R)-1-((1-(2-(3-chloro-1-cyclopropyl-1H-indol-5-ylamino)pyrimidin-4-yl)-3-methyl-1H-pyrazol-4-yl)methyl)pyrrolidin-3-ol,
(R)-1-((1-(2-(3-bromo-1,2-dimethyl-1H-indol-5-ylamino)pyrimidin-4-yl)-3-methyl-1H-pyrazol-4-yl)methyl)pyrrolidin-3-ol,
(R)-cyclopropyl(5-(4-(4-((3-hydroxypyrrolidin-1-yl)methyl)-3-methyl-1H-pyrazol-1-yl)pyrimidin-2-ylamino)-1-methyl-1H-indol-3-yl)methanone,
(R)-cyclopropyl(5-(4-(4-((3-hydroxypiperidin-1-yl)methyl)-3-methyl-1H-pyrazol-1-yl)pyrimidin-2-ylamino)-1-methyl-1H-indol-3-yl)methanone,
(R)-1-((1-(2-(3-chloro-1,2-dimethyl-1H-indol-5-ylamino)pyrimidin-4-yl)-3-methyl-1H-pyrazol-4-yl)methyl)piperidin-3-ol,
(R)-1-((1-(2-(3-chloro-1-methyl-1H-indol-5-ylamino)pyrimidin-4-yl)-3-methyl-1H-pyrazol-4-yl)methyl)piperidin-3-ol,
(S)-1-((1-(2-(3-chloro-1,2-dimethyl-1H-indol-5-ylamino)pyrimidin-4-yl)-3-methyl-1H-pyrazol-4-yl)methyl)pyrrolidin-3-ol,
(S)-1-((1-(2-(3-chloro-1-cyclopropyl-1H-indol-5-ylamino)pyrimidin-4-yl)-3-methyl-1H-pyrazol-4-yl)methyl)pyrrolidin-3-ol,
1-((1-(2-(3-chloro-1-methyl-1H-indazol-5-ylamino)-5-fluoropyrimidin-4-yl)-4-methyl-1H-pyrrol-3-yl)methyl)azetidin-3-ol,
1-((1-(2-(3-chloro-1-isopropyl-1H-indazol-5-ylamino)-5-fluoropyrimidin-4-yl)-4-methyl-1H-pyrrol-3-yl)methyl)azetidin-3-ol,
1-((1-(2-(3-chloro-2-isopropyl-2H-indazol-5-ylamino)-5-fluoropyrimidin-4-yl)-4-methyl-1H-pyrrol-3-yl)methyl)azetidin-3-ol,
1-((1-(2-(3-chloro-1,2-dimethyl-1H-indol-5-ylamino)-5-methylpyrimidin-4-yl)-4-methyl-1H-pyrrol-3-yl)methyl)azetidin-3-ol,
(R)-1-((1-(2-(3-chloro-1-methyl-1H-indol-5-ylamino)pyrimidin-4-yl)-3-methyl-1H-pyrazol-4-yl)methyl)pyrrolidin-3-ol,
(R)-1-((1-(2-(3-chloro-1-cyclopropyl-1H-indol-5-ylamino)pyrimidin-4-yl)-3-methyl-1H-pyrazol-4-yl)methyl)pyrrolidin-3-ol,
(R)-1-((1-(2-(3-bromo-1,2-dimethyl-1H-indol-5-ylamino)pyrimidin-4-yl)-3-methyl-1H-pyrazol-4-yl)methyl)pyrrolidin-3-ol,
(R)-cyclopropyl(5-(4-(4-((3-hydroxypyrrolidin-1-yl)methyl)-3-methyl-1H-pyrazol-1-yl)pyrimidin-2-ylamino)-1-methyl-1H-indol-3-yl)methanone,
(R)-cyclopropyl(5-(4-(4-((3-hydroxypiperidin-1-yl)methyl)-3-methyl-1H-pyrazol-1-yl)pyrimidin-2-ylamino)-1-methyl-1H-indol-3-yl)methanone,
(R)-1-((1-(2-(3-chloro-1,2-dimethyl-1H-indol-5-ylamino)pyrimidin-4-yl)-3-methyl-1H-pyrazol-4-yl)methyl)piperidin-3-ol,
(R)-1-((1-(2-(3-chloro-1-methyl-1H-indol-5-ylamino)pyrimidin-4-yl)-3-methyl-1H-pyrazol-4-yl)methyl)piperidin-3-ol,
(S)-1-((1-(2-(3-chloro-1,2-dimethyl-1H-indol-5-ylamino)pyrimidin-4-yl)-3-methyl-1H-pyrazol-4-yl)methyl)pyrrolidin-3-ol,
(S)-1-((1-(2-(3-chloro-1-cyclopropyl-1H-indol-5-ylamino)pyrimidin-4-yl)-3-methyl-1H-pyrazol-4-yl)methyl)pyrrolidin-3-ol,
(1-(2-(1-cyclopropyl-3-methyl-1H-indol-5-ylamino)pyrimidin-4-yl)-3-methyl-1H-pyrazol-4-yl)(3-hydroxyazetidin-1-yl)methanone,
3-chloro-1,2-dimethyl-N-(6-(3-methyl-4-(piperazin-1-ylmethyl)-1H-pyrrol-1-yl)pyridin-2-yl)-1H-indol-5-amine,
(R)-1-(5-(6-(3-((3-hydroxypyrrolidin-1-yl)methyl)-4-methyl-1H-pyrrol-1-yl)pyridin-2-ylamino)-1-methyl-1H-indol-3-yl)-2,2,2-trifluoroethanone,
1-(5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)ethanone,
(R)-1-(5-(4-(4-((3-hydroxypyrrolidin-1-yl)methyl)-3-methyl-1H-pyrazol-1-yl)pyrimidin-2-ylamino)-1H-indol-3-yl)ethanone,
1-(5-(4-(4-((3-hydroxyazetidin-1-yl)methyl)-3-methyl-1H-pyrazol-1-yl)pyrimidin-2-ylamino)-1H-indol-3-yl)ethanone,
1-(5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)-2,2,2-trifluoroethanone
(R)-1-(5-(4-(4-((3-hydroxypyrrolidin-1-yl)methyl)-3-methyl-1H-pyrazol-1-yl)pyrimidin-2-ylamino)-1H-indol-3-yl)-2,2,2-trifluoroethanone,
1-(5-(4-(4-(((2S,4R)-4-hydroxy-2-(hydroxymethyl)pyrrolidin-1-yl)methyl)-3-methyl-1H-pyrazol-1-yl)pyrimidin-2-ylamino)-1H-indol-3-yl)-2,2,2-trifluoroethanone
1-(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)-2,2,2-trifluoroethanone,
1-(5-(4-(4-(((3S,4R)-4-hydroxy-4-methoxypyrrolidin-1-yl)methyl)-3-methyl-1H-pyrazol-1-yl)pyrimidin-2-ylamino)-1-methyl-1H-indol-3-yl)-2,2,2-trifluoroethanone,
1-(5-(4-(4-(((2S,4R)-4-hydroxy-2-(hydroxymethyl)pyrrolidin-1-yl)methyl)-3-methyl-1H-pyrazol-1-yl)pyrimidin-2-ylamino)-1-methyl-1H-indol-3-yl)-2,2,2-trifluoroethanone,
cyclopropyl(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)methanone,
cyclopropyl(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)methanone
cyclopropyl(5-(4-(4-(((3S,4S)-3,4-dihydroxypyrrolidin-1-yl)methyl)-3-methyl-1H-pyrazol-1-yl)pyrimidin-2-ylamino)-1-methyl-1H-indol-3-yl)methanone,
(3R,4S)-1-((1-(2-(3-(cyclopropanecarbonyl)-1-methyl-1H-indol-5-ylamino)pyrimidin-4-yl)-3-methyl-1H-pyrazol-4-yl)methyl)pyrrolidine-3,4-dihydroxyl diacetate,
cyclopropyl(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)methanone, cyclopropyl(5-(4-(4-(((3S,4R)-3-hydroxy-4-methoxypyrrolidin-1-yl)methyl)-3-methyl-1H-pyrazol-1-yl)pyrimidin-2-ylamino)-1H-indol-3-yl)methanone, (R)-cyclopropyl(5-(4-(4-((3-hydroxypyrrolidin-1-yl)methyl)-3-methyl-1H-pyrazol-1-yl)pyrimidin-2-ylamino)-1H-indol-3-yl)methanone, 1-(5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)-2,2-difluoroethanone, (R)-2,2-difluoro-1-(5-(4-(4-((3-hydroxypyrrolidin-1-yl)methyl)-3-methyl-1H-pyrazol-1-yl)pyrimidin-2-ylamino)-1H-indol-3-yl)ethanone, 1-(5-(4-(4-(((3S,4S)-3,4-dihydroxypyrrolidin-1-yl)methyl)-3-methyl-1H-pyrazol-1-yl)pyrimidin-2-ylamino)-1H-indol-3-yl)-2,2-difluoroethanone, 2,2-difluoro-1-(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)ethanone, 1-(5-(4-(4-(((3S,4S)-3,4-dihydroxypyrrolidin-1-yl)methyl)-3-methyl-1H-pyrazol-1-yl)pyrimidin-2-ylamino)-1-methyl-1H-indol-3-yl)-2,2-difluoroethanone, (R)-2,2-difluoro-1-(5-(4-(4-((3-hydroxypyrrolidin-1-yl)methyl)-3-methyl-1H-pyrazol-1-yl)pyrimidin-2-ylamino)-1-methyl-1H-indol-3-yl)ethanone, 1-(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one, 1-(5-(4-(4-(((3S,4S)-3,4-dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one, (R)-1-(5-(4-(4-((3-hydroxypyrrolidin-1-yl)methyl)-3-methyl-1H-pyrazol-1-yl)pyrimidin-2-ylamino)-1-methyl-1H-indol-3-yl)-2,2-dimethylpropan-1-one, cyclopropyl(1-cyclopropyl-5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)methanone, (R)-cyclopropyl(1-cyclopropyl-5-(4-(4-((3-hydroxypyrrolidin-1-yl)methyl)-3-methyl-1H-pyrazol-1-yl)pyrimidin-2-ylamino)-1H-indol-3-yl)methanone, (R)-cyclopropyl(1-cyclopropyl-5-(4-(4-((3-methoxypyrrolidin-1-yl)methyl)-3-methyl-1H-pyrazol-1-yl)pyrimidin-2-ylamino)-1H-indol-3-yl)methanone, (3S,4R)-1-((1-(2-(3-chloro-1,2-dimethyl-1H-indol-5-ylamino)pyrimidin-4-yl)-3-methyl-1H-pyrazol-4-yl)methyl)-4-fluoropyrrolidin-3-ol, (2S,4R)-1-((1-(2-(3-chloro-1,2-dimethyl-1H-indol-5-ylamino)pyrimidin-4-yl)-3-methyl-1H-pyrazol-4-yl)methyl)-4-hydroxypyrrolidine-2-carboxylic acid, (3S,4S)-1-((1-(2-(3-chloro-1,2-dimethyl-1H-indol-5-ylamino)pyrimidin-4-yl)-3-methyl-1H-pyrazol-4-yl)methyl)-4-(dimethylamino)pyrrolidin-3-ol, (R)-2-(((1-(2-(3-chloro-1,2-dimethyl-1H-indol-5-ylamino)pyrimidin-4-yl)-3-methyl-1H-pyrazol-4-yl)methyl)(ethyl)amino)propan-1-ol, 3-chloro-N-(4-(4-((3-methoxyazetidin-1-yl)methyl)-3-methyl-1H-pyrazol-1-yl)pyrimidin-2-yl)-1,2-dimethyl-1H-indol-5-amine, (3R,5S)-1-((1-(2-(3-chloro-1,2-dimethyl-1H-indol-5-ylamino)pyrimidin-4-yl)-3-methyl-1H-pyrazol-4-yl)methyl)-5-(methoxymethyl)pyrrolidin-3-ol, 1-(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)-2-methylpropan-1-one, 1-(5-(4-(4-(((3 S,4 S)-3,4-dihydroxypyrrolidin-1-yl)methyl)-3-methyl-1H-pyrazol-1-yl)pyrimidin-2-ylamino)-1-methyl-1H-indol-3-yl)-2-methylpropan-1-one, (R)-1-(5-(4-(4-((3-hydroxypyrrolidin-1-yl)methyl)-3-methyl-1H-pyrazol-1-yl)pyrimidin-2-ylamino)-1-methyl-1H-indol-3-yl)-2-methylpropan-1-one, 1-(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)-2-methylpropan-1-one, (R)-1-(2-(1-(2-(3-chloro-1,2-dimethyl-1H-indol-5-ylamino)pyrimidin-4-yl)-3-methyl-1H-pyrazol-4-yl)ethyl)pyrrolidin-3-ol, 1-(2-(1-(2-(3-chloro-1,2-dimethyl-1H-indol-5-ylamino)pyrimidin-4-yl)-3-methyl-1H-pyrazol-4-yl)ethyl)azetidin-3-ol, cis-1-((1-(2-(3-chloro-1,2-dimethyl-1H-indol-5-ylamino)pyrimidin-4-yl)-3-methyl-1H-pyrazol-4-yl)methyl)pyrrolidine-3,4-diol, (S)-1-((1-(2-(3-chloro-1,2-dimethyl-1H-indol-5-ylamino)pyrimidin-4-yl)-3-methyl-1H-pyrazol-4-yl)methyl)pyrrolidine-2-carboxylic acid, (1S,2S)-2-((1-(2-(3-chloro-1,2-dimethyl-1H-indol-5-ylamino)pyrimidin-4-yl)-3-methyl-1H-pyrazol-4-yl)methylamino)cyclohexanol, (1S,2S)—N1-((1-(2-(3-chloro-1,2-dimethyl-1H-indol-5-ylamino)pyrimidin-4-yl)-3-methyl-1H-pyrazol-4-yl)methyl)cyclopentane-1,2-diamine, trans-4-((1-(2-(3-chloro-1,2-dimethyl-1H-indol-5-ylamino)pyrimidin-4-yl)-3-methyl-1H-pyrazol-4-yl)methylamino)cyclohexanol, (1S,2R)—N1-((1-(2-(3-chloro-1,2-dimethyl-1H-indol-5-ylamino)pyrimidin-4-yl)-3-methyl-1H-pyrazol-4-yl)methyl)cyclohexane-1,2-diamine, (1S,2S)-2-((1-(2-(3-chloro-1,2-dimethyl-1H-indol-5-ylamino)pyrimidin-4-yl)-3-methyl-1H-pyrazol-4-yl)methylamino)cyclopentanol, (1S,3 S)-3-((1-(2-(3-chloro-1,2-dimethyl-1H-indol-5-ylamino)pyrimidin-4-yl)-3-methyl-1H-pyrazol-4-yl)methylamino)cyclobutanol, (3R,5S)-1-((1-(2-(3-chloro-1,2-dimethyl-1H-indol-5-ylamino)pyrimidin-4-yl)-3-methyl-1H-pyrazol-4-yl)methyl)-5-(hydroxymethyl)pyrrolidin-3-ol, (3S,4R)-1-((1-(2-(3-chloro-1,2-dimethyl-1H-indol-5-ylamino)pyrimidin-4-yl)-3-methyl-1H-pyrazol-4-yl)methyl)-4-methoxypyrrolidin-3-ol, (3S,4R)-1-((1-(2-(3-chloro-1,2-dimethyl-1H-indol-5-ylamino)pyrimidin-4-yl)-3-methyl-1H-pyrazol-4-yl)methyl)-4-isopropoxypyrrolidin-3-ol, cis-3-chloro-N-(4-(4-((3,4-dimethoxypyrrolidin-1-yl)methyl)-3-methyl-1H-pyrazol-1-yl)pyrimidin-2-yl)-1,2-dimethyl-1H-indol-5-amine, (3R,5R)-1-((1-(2-(3-chloro-1,2-dimethyl-1H-indol-5-ylamino)pyrimidin-4-yl)-3-methyl-1H-pyrazol-4-yl)methyl)-5-methylpyrrolidin-3-ol, cyclopropyl(5-(4-(4-(((3R,4S)-3,4-dihydroxypyrrolidin-1-yl)methyl)-3-methyl-1H-pyrazol-1-yl)pyrimidin-2-ylamino)-1,2-dimethyl-1H-indol-3-yl)methanone, cyclopropyl(5-(4-(4-((3-hydroxyazetidin-1-yl)methyl)-3-methyl-1H-pyrazol-1-yl)pyrimidin-2-ylamino)-1,2-dimethyl-1H-indol-3-yl)methanone, cis-1-((3-methyl-1-(2-(1-methyl-3-(methylsulfonyl)-1H-indazol-5-ylamino)pyrimidin-4-yl)-1H-pyrazol-4-yl)methyl)pyrrolidine-3,4-diol, (3S,4R)-4-methoxy-1-((3-methyl-1-(2-(1-methyl-3-(methylsulfonyl)-1H-indazol-5-ylamino)pyrimidin-4-yl)-1H-pyrazol-4-yl)methyl)pyrrolidin-3-ol, cis-1-((1-(2-(3-bromo-1,2-dimethyl-1H-indol-5-ylamino)pyrimidin-4-yl)-3-methyl-1H-pyrazol-4-yl)methyl)pyrrolidine-3,4-diol, 1-((1-(2-(3-chloro-2-methyl-1-propyl-1H-indol-5-ylamino)pyrimidin-4-yl)-3-methyl-1H-pyrazol-4-yl)methyl)azetidin-3-ol,
cis-1-((1-(2-(3-chloro-2-methyl-1-propyl-1H-indol-5-ylamino)pyrimidin-4-yl)-3-methyl-1H-pyrazol-4-yl)methyl)pyrrolidine-3,4-diol,
(3R,5S)-1-((1-(2-(3-chloro-2-methyl-1-propyl-1H-indol-5-ylamino)pyrimidin-4-yl)-3-methyl-1H-pyrazol-4-yl)methyl)-5-(hydroxymethyl)pyrrolidin-3-ol,
cyclopropyl(5-(4-(4-((cis-3,4-dihydroxypyrrolidin-1-yl)methyl)-3-methyl-1H-pyrazol-1-yl)pyrimidin-2-ylamino)-1,2-dimethyl-1H-indol-3-yl)methanone,
cyclopropyl(5-(4-(4-((3-hydroxyazetidin-1-yl)methyl)-3-methyl-1H-pyrazol-1-yl)pyrimidin-2-ylamino)-1,2-dimethyl-1H-indol-3-yl)methanone,
1-((1-(2-(3-bromo-1-(2-methoxyethyl)-2-methyl-1H-indol-5-ylamino)pyrimidin-4-yl)-3-methyl-1H-pyrazol-4-yl)methyl)azetidin-3-ol,
(R)-1-((1-(2-(3-Bromo-1-(2-methoxyethyl)-2-methyl-1H-indol-5-ylamino)pyrimidin-4-yl)-3-methyl-1H-pyrazol-4-yl)methyl)pyrrolidin-3-ol,
cis-1-((1-(2-(3-bromo-1-(2-methoxyethyl)-2-methyl-1H-indol-5-ylamino)pyrimidin-4-yl)-3-methyl-1H-pyrazol-4-yl)methyl)pyrrolidine-3,4-diol,
cis-1-((3-methyl-1-(2-(1-methyl-3-(methylsulfonyl)-1H-indol-5-ylamino)pyrimidin-4-yl)-1H-pyrazol-4-yl)methyl)pyrrolidine-3,4-diol,
cis-1-((1-(2-(3-chloro-1-(2-hydroxyethyl)-2-methyl-1H-indol-5-ylamino)pyrimidin-4-yl)-3-methyl-1H-pyrazol-4-yl)methyl)pyrrolidine-3,4-diol,
(3R,5S)-5-(hydroxymethyl)-1-((3-methyl-1-(2-(1-methyl-3-(methylsulfonyl)-1H-indol-5-ylamino)pyrimidin-4-yl)-1H-pyrazol-4-yl)methyl)pyrrolidin-3-ol and
cis-1-((1-(2-(3-cyclopentyl-1-methyl-1H-indol-5-ylamino)pyrimidin-4-yl)-3-methyl-1H-pyrazol-4-yl)methyl)pyrrolidine-3,4-diol;
or a pharmaceutically acceptable salt thereof.

As used herein, the term "dermatological disorder" refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

As used herein, the term "neurogenerative disease" or "nervous system disorder" refers to conditions that alter the structure or function of the brain, spinal cord or peripheral nervous system, including but not limited to Alzheimer's disease, cerebral edema, cerebral ischemia, multiple sclerosis, neuropathies, Parkinson's disease, those found after blunt or surgical trauma (including post-surgical cognitive dysfunction and spinal cord or brain stem injury), as well as the neurological aspects of disorders such as degenerative disk disease and sciatica. The acronym "CNS" refers to the central nervous system (brain and spinal cord).

As used herein, the term "respiratory disease" refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

As used herein, the term "cancer" refers to an abnormal growth of cells which tend to proliferate in an uncontrolled way and, in some cases, to metastasize. The types of cancer include, but is not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function, which may be partial or complete, temporary or permanent. Inflammation takes many forms and includes, but is not limited to, inflammation that is one or more of the following, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract; skin (dermatitis); or multiple organs and tissues (systemic lupus erythematosus).

As used herein, the term "cardiovascular disease" refers to diseases affecting the heart or blood vessels or both, including but not limited to atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

As used herein, the term "bone disease" means a disease or condition of the bone, including, but not limited to, inappropriate bone remodeling, loss or gain, osteopenia, osteomalacia, osteofibrosis, osteoporosis and Paget's disease.

As used herein, the term "inhibitor" refers to a compound which inhibits one or more kinases described herein. For example, the term "SYK inhibitor" refers to a compound which inhibits the SYK receptor or reduces the signaling effect.

As used herein, the term "pharmaceutically acceptable" refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein. Pharmaceutically acceptable salts include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts. As used herein, the term "pharmaceutical combination" means a product that results from the mixing or combining of more than one active ingredient.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into the parent drug in vivo.

As used herein, the term "protein kinase-mediated disease" or a "disorder or disease or condition mediated by inappropriate protein kinase activity" refers to any disease state mediated or modulated by protein kinases described herein. Such disease states include, but are not limited to, asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, bullous disorders, collagenoses, contact dermatitis eczema, Kawasaki Disease, rosacea, Sjogren-Larsso Syndrome, rheumatoid arthritis, multiple sclerosis, inflammatory bowel syndrome, HIV, lupus, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, gastrointestinal cancer, Alzheimer's disease, Parkinson's disease, osteoporosis, osteopenia, osteomalacia, osteofibrosis, Paget's disease, diabetes, blood vessel proliferative disorders, ocular diseases, cardiovascular disease, restenosis, fibrosis, atherosclerosis, arrhythmia, angina, myocardial ischemia, myocardial infarction, cardiac or vascular aneurysm, vasculitis, stroke, peripheral obstructive arteriopathy, reperfusion injury following ischemia of an organ or a tissue, endotoxic, surgical or traumatic shock, hypertension, valvular heart disease, heart failure, abnormal blood pressure, vasoconstriction, vascular abnormality, transplant rejection and infectious diseases including viral and fungal infections.

As used herein, the term "kinase-mediated disease" or "kinase-mediated disease" or a "disorder or disease or condition mediated by inappropriate kinase activity" refers to any disease state mediated or modulated by a kinase mechanism. For example "SYK-mediated disease" refers to any disease state mediated or modulated by SYK mechanisms. Such SYK-mediated disease states include, but are not limited to, inflammatory, respiratory diseases and autoimmune diseases, such as, by way of example only, asthma, chronic obstructive pulmonary disease (COPD), adult respiratory distress syndrome (ARDs), ulcerative colitis, Crohn's disease, bronchitis, dermatitis, allergic rhinitis, psoriasis, scleroderma, urticaria, rheumatoid arthritis, multiple sclerosis, cancer, HIV-associated disease and lupus.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention and/or prodrugs thereof to a subject in need of treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. By way of example only, a therapeutically effective amount of a compound of the invention may be in the range of e.g., about 0.01 mg/kg/day to about 100 mg/kg/day, or from about 0.1 mg/kg/day to about 10 mg/kg/day.

1. Human Protein Kinases

The compounds of the present invention were screened against the kinase panel and inhibited the activity of at least one kinase on the panel. Examples of kinases include, but are not limited to SYK and mutant forms thereof.

The compounds described herein are inhibitors of SYK kinase activity and have therapeutic benefit in the treatment of disorders associated with inappropriate kinase activity, in particular in the treatment and prevention of disease states mediated by kinases, including SYK kinase. Therefore, the present invention provides methods of regulating and, in particular, inhibiting signal transduction cascades in which a kinase plays a role. The method generally involves administering to a subject or contacting a cell expressing the kinase with an effective amount of a compound described herein, prodrug, or an acceptable salt, hydrate, solvate, N-oxide and/or composition thereof, to regulate or inhibit the signal transduction cascade. The methods are also used to regulate and, in particular, inhibit downstream processes or cellular responses elicited by activation of the particular kinase signal transduction cascade. The methods are also practiced in in vitro contexts or in in vivo contexts as a therapeutic approach towards the treatment or prevention of diseases characterized by, caused by, or associated with activation of the kinase-dependent signal transduction cascade.

2. Pharmaceutical Compositions

For the therapeutic uses of compounds provided herein, including compounds of Formula (I), or pharmaceutically acceptable salts, solvates, N-oxides, prodrugs, or isomers thereof, such compounds are administered in therapeutically effective amounts either alone or as part of a pharmaceutical composition. Accordingly, provided herein are pharmaceutical compositions, which comprise at least one compound provided herein, including at least one compound of Formula (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or optic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al., Bioorg. Med. Chem. Letters, 1994, 4, 1985; the entire teachings of which are incorporated herein by reference).

Protected derivatives of the compounds of the invention may be prepared by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of the invention may be prepared as their individual stereoisomers by reaction of a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet and Samuel H. Wilen, "Enantiomers, Racemates and Resolutions," John Wiley And Sons, Inc., 1981, the entire teachings of which are incorporated herein by reference.

Suitable pharmaceutically acceptable carriers, diluents, adjuvants, or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

Compounds of Formula (I) can be made according to a variety of methods, some of which are known in the art. For example, the methods disclosed in PCT Publication WO2011/060295 (incorporated herein by reference) can be used, with suitable modifications, to prepare compounds according to the present invention. Exemplary methods for preparing the compounds of the invention are described herein, including in the Examples.

In certain embodiments, compounds of Formula (I) are made by:
(a) optionally converting a compound of the invention into a pharmaceutically acceptable salt; (b) optionally converting a salt form of a compound of the invention to a non-salt form; (c) optionally converting an unoxidized form of a compound of the invention into a pharmaceutically acceptable N-oxide; (d) optionally resolving an individual isomer of a compound of the invention from a mixture of isomers; (e) optionally converting a non-derivatized compound of the invention into a pharmaceutically acceptable prodrug derivative; and (f) optionally converting a prodrug derivative of a compound of the invention to its non-derivatized form.

The teachings of all patents, published applications and references cited herein are incorporated by reference in their entirety.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.

Nuclear magnetic resonance (NMR) and mass spectrometry (MS) spectra obtained for compounds described in the examples below and those described herein were consistent with that of the compounds of formulae herein.

Liquid Chromatography-Mass Spectrometry (LC-MS) Method:
1. Samples are run on Agilent Technologies 6120 MSD system with a Zorbax Eclipse XDB-C18 (3.5µ) reverse phase column (4.6×50 mm) run at room temperature with flow rate of 1.5 mL/minute.
2. The mobile phase uses solvent A (water/0.1% formic acid) and solvent B (acetonitrile/0.1% formic acid): 95%/5% to 0%/100% (A/B) for 5 minute.
3. The mass spectra (m/z) were recorded using electrospray ionization (ESI).
4. Ionization data was rounded to the nearest integer.

Proton NMR Spectra:
Unless otherwise indicated, all $^1$H NMR spectra are run on a Varian series Mercury 300 MHz. All observed protons are reported as parts-per-million (ppm) downfield from tetramethylsilane using conventional abbreviations for designation of major peaks: e.g., s (singlet), d (doublet), t (triplet), q (quartet), m (multiplet) and br (broad).

Preparation of ethyl 1-(2-chloropyrimidin-4-yl)-3-methyl-1H-pyrazole-4-carboxylate; Intermediate 1

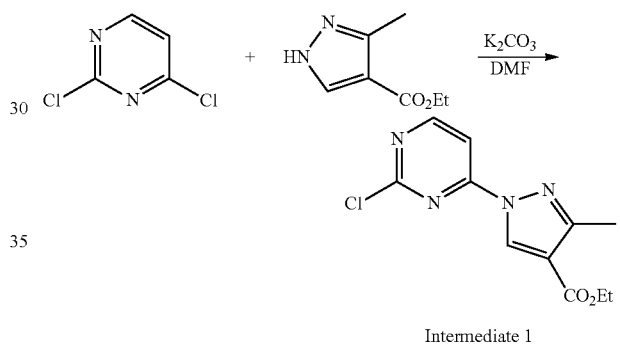

Intermediate 1

To a solution of ethyl 3-methyl-1H-pyrazole-4-carboxylate (6.0 g, 38.9 mmol) in 50 mL of anhydrous N,N-dimethylformamide (DMF) were added potassium carbonate (10.8 g, 77.8 mmol) and 2,4-dichloropyrimidine (5.8 g, 38.9 mmol) at room temperature. The resulting suspension was stirred for 8 hours with monitoring a reaction with LC-MS or thin layer chromatography (TLC). Volatiles were removed and the residue was extracted with dichloromethane. The collected organic layer was washed with brine, dried over anhydrous sodium sulfate and then concentrated in vacuo. The resulting residue was purified by silica gel chromatography using a mixture of heptanes and ethyl acetate to afford the desired intermediate 1 as a white solid (5.45 g, 52%); MS (ESI) m/z 267 [M+H]$^+$, $^1$H NMR (300 MHz, CDCl$_3$) δ 8.99 (s, 1H), 8.68 (d, 1H, J=5.4 Hz), 7.86 (d, 1H, J=5.4 Hz), 4.35 (q, 2H, J=7.2 Hz), 2.57 (s, 3H), 1.40 (t, 3H, J=7.2 Hz).

Preparation of 1-(2-chloropyrimidin-4-yl)-3-methyl-1H-pyrazole-4-carbaldehyde; Intermediate 2

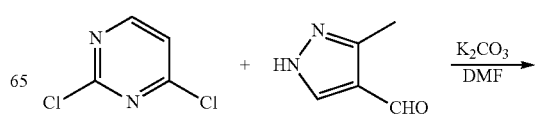

67

-continued

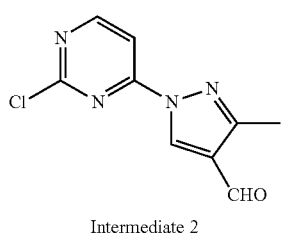

Intermediate 2

To a solution of ethyl 3-methyl-1H-pyrazole-4-carbaldehyde (6.4 g, 58.0 mmol) in 60 mL of anhydrous N,N-dimethylformamide were added potassium carbonate (10.8 g, 77.8 mmol) and 2,4-dichloropyrimidine (8.64 g, 58.0 mmol) at room temperature. The resulting suspension was stirred for 14 hours at room temperature with monitoring a reaction with LC-MS or thin layer chromatography (TLC). The reaction mixture was diluted with ethyl acetate and washed with brine (×2). The collected organic layer was dried over anhydrous sodium sulfate and then concentrated in vacuo. The resulting residue was purified by silica gel chromatography using a mixture of heptanes and ethyl acetate to afford the desired intermediate 2 as a white solid (5.47 g, 42%); MS (ESI) m/z 223 [M+H]$^+$, $^1$H NMR (300 MHz, CDCl$_3$) δ 10.06 (s, 1H), 9.04 (s, 1H), 8.70 (d, 1H, J=5.4 Hz), 7.87 (1H, d, J=5.4 Hz), 2.59 (s, 3H).

Preparation of ethyl 1-(2-chloro-5-fluoropyrimidin-4-yl)-3-methyl-1H-pyrazole-4-carboxylate; Intermediate 3

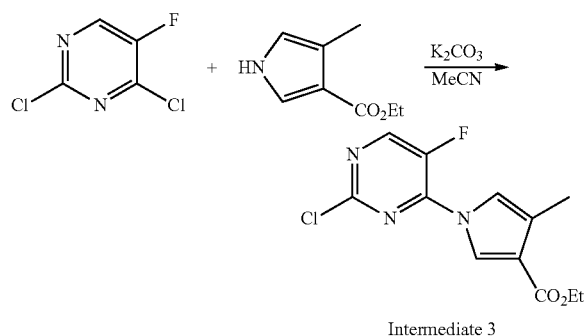

Intermediate 3

To a solution of ethyl 3-methyl-1H-pyrrole-4-carboxylate (3.15 g, 20.5 mmol) in acetonitrile (MeCN) were added potassium carbonate (5.7 g, 41 mmol) and 2,4-dichloro-5-fluoropyrimidine (3.4 g, 20.5 mmol) at room temperature. The resulting slurry was heated at 80° C. for 3 hours with monitoring a reaction with LC-MS or thin layer chromatography (TLC). It was diluted with ethyl acetate and washed with brine. The collected organic layer was dried over anhydrous sodium sulfate and then partially concentrated in vacuo. To this, n-hexanes were added to form pale yellow precipitates. The resulting solids were collected by filtration and rinsed with n-hexanes and then dried under high vacuum to give 4.9 g (85%) of the target intermediate 3; MS (ESI) m/z 285 [M+H]$^+$

68

Preparation of ethyl 1-(2-chloropyrimidin-4-yl)-3-cyclopropyl-1H-pyrazole-4-carboxylate; Intermediate 4

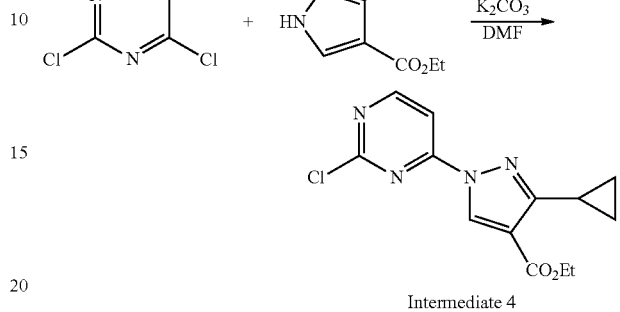

Intermediate 4

To a solution of ethyl 3-cyclopropyl-1H-pyrazole-4-carbaldehyde (5.4 g, 30.0 mmol) in 100 mL of anhydrous N,N-dimethylformamide were added potassium carbonate (10.4 g, 75 mmol) and 2,4-dichloropyrimidine (7.1 g, 30.0 mmol) at room temperature. The resulting suspension was stirred for 6 hours at 60° C. with monitoring a reaction with LC-MS or thin layer chromatography (TLC). Volatiles were removed and the residue was extracted with dichloromethane. The collected organic layer was washed with brine, dried over anhydrous sodium sulfate and then concentrated in vacuo. The resulting solid was recrystallized in acetonitrile to afford the desired intermediate 4 as a pale yellow solid (6.0 g, 68%); MS (ESI) m/z 293 [M+H]$^+$.

Preparation of ethyl 1-(2-chloro-5-methylpyrimidin-4-yl)-3-methyl-1H-pyrazole-4-carboxylate; Intermediate 5

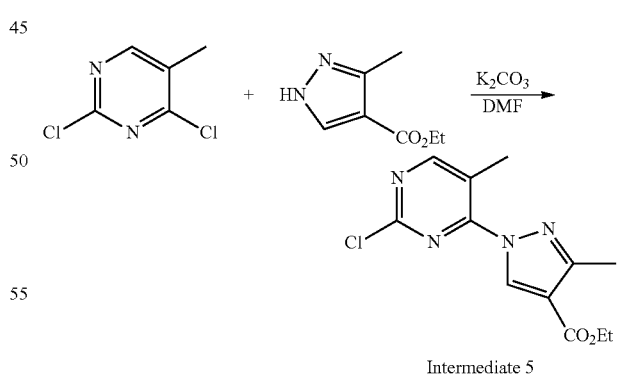

Intermediate 5

To a solution of ethyl 3-methyl-1H-pyrazole-4-carboxylate (4.7 g, 30.6 mmol) in acetonitrile were added potassium carbonate (10.6 g, 75.0 mmol) and 2,4-dichloro-5-methylpyrimidine (5.0 g, 30.6 mmol) at room temperature. The resulting suspension was heated at 80° C. for 3 hours with monitoring a reaction with LC-MS or thin layer chromatography (TLC). Volatiles were partially removed and the residue was extracted with ethyl acetate. The collected organic layer was washed with brine, dried over anhydrous sodium sulfate and then concentrated in vacuo. The resulting solid was recrystallized in a mixture of heptanes and ethyl acetate to afford the desired intermediate 5 as a pale yellow solid (5.2 g, 61%); MS (ESI) m/z 281 [M+H]+.

Method I: Preparation 1-((3-methyl-1-(2-(1-methyl-1H-indol-5-ylamino)pyrimidin-4-yl)-1H-pyrazol-4-yl)methyl)azetidin-3-ol; Compound 1

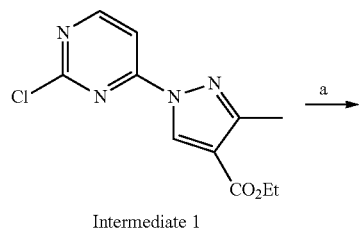

Intermediate 1

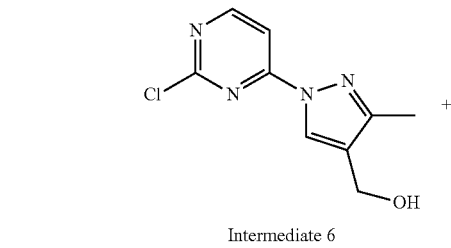

Intermediate 6

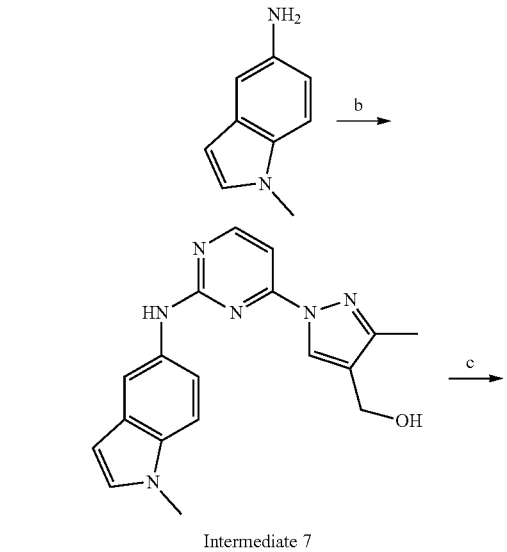

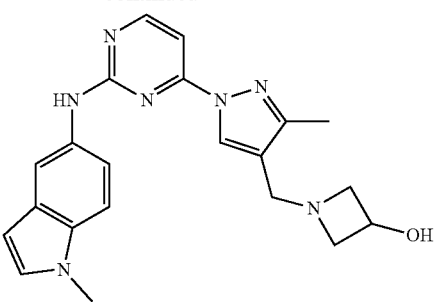

Compound 1 a) DIBAL-H, THF, b) Pd(OAc)₂, Xantphos, K₂CO₃, Dioxane, c) MnO₂, DCM, rt, d) 3-azetidinole hydrochloride, NaBH(OAc)₃, Et₃N, DCM Preparation of (1-(2-chloropyrimidin-4-yl)-3-methyl-1H-pyrazol-4-yl)methanol; Intermediate 6

To a solution of ethyl 1-(2-chloropyrimidin-4-yl)-3-methyl-1H-pyrazole-4-carboxylate intermediate 1 (6.5 g, 24.0 mmol) in 50 mL of anhydrous tetrahydrofuran (THF), was slowly added 109 mL (4.5 equiv.) of 1M solution of di-isobutylaluminum hydride (DIBAL-H) in toluene with ice bath cooling. After being stirred for 2 hours at room temperature, the reaction was quenched by slow addition of 1N—NaOH solution. It was diluted with ethyl acetate and washed with brine. The collected organic layer was dried over anhydrous sodium sulfate and then partially concentrated in vacuo. To this, was heptane added to form pale yellow precipitates. The resulting solids were collected by filtration and rinsed with heptanes and then dried under high vacuum to give 3.6 g (66%) of intermediate alcohol 6. MS (ESI) m/z 225 [M+H]+.

71

Preparation of (3-methyl-1-(2-(1-methyl-1H-indol-5-ylamino)pyrimidin-4-yl)-1H-pyrazol-4-yl)methanol; Intermediate 7

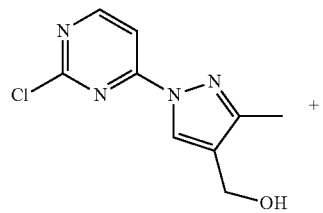

Intermediate 6

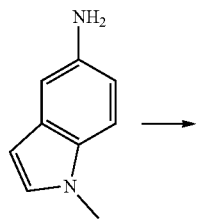

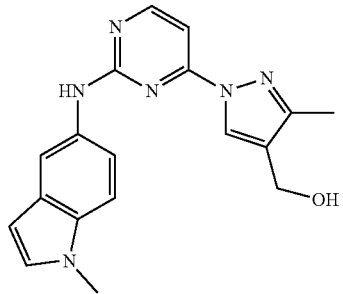

Intermediate 7

A round bottomed flask was charged with methyl (1-(2-chloropyrimidin-4-yl)-3-methyl-1H-pyrazol-4-yl)methanol (400 mg, 1.78 mmol), 1-methyl-1H-indol-5-amine (338 mg, 1.3 equiv.), potassium carbonate (0.74 g, 3.0 equiv), palladium acetate (40 mg, 0.1 equiv), (9,9-dimethyl-9H-xanthene-4,5-diyl)bis(diphenylphosphine) (Xantphos, 206 mg, 0.2 equiv.) and 40 mL of anhydrous dioxane. After being degassed by nitrogen bubbling, the reaction mixture was heated at 100° C. for 12 hours. Volatiles were removed in vacuo and then the resulting residue was extracted with ethyl acetate. The collected organic layer was dried over anhydrous sodium sulfate and then concentrated in vacuo. The resulting residue was purified by recrystallization in acetonitrile to give 241 mg (36%) of the desired product as a brown solid. MS (ESI) m/z 335 [M+H]+.

Preparation of 3-methyl-1-(2-(1-methyl-1H-indol-5-ylamino)pyrimidin-4-yl)-1H-pyrazole-4-carbaldehyde; Intermediate 8

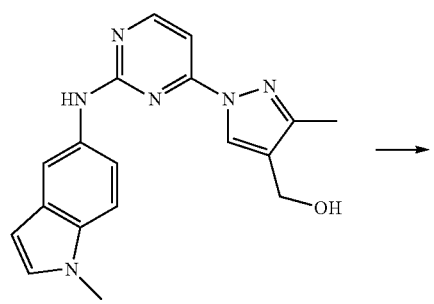

Intermediate 7

72

-continued

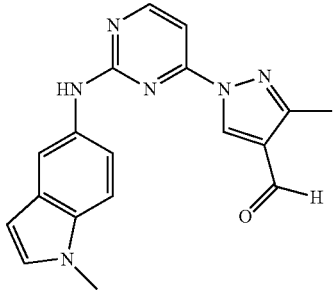

Intermediate 8

To a solution of intermediate 7 (214 mg, 0.64 mmol) in 100 mL of dichloromethane (DCM), was added 58% of activated MnO$_2$ (0.58 g, 6 equiv.). After being stirred for 12 hours at room temperature, the reaction mixture was passed through a pad of Celite and rinsed with dichloromethane. The filtrate was concentrated in vacuo to give desired intermediate 8 as a pale yellow solid (0.77 g, 36%); MS (ESI) m/z 333 [M+H]+

Preparation of 1-((4-methyl-1-(2-(1-methyl-1H-indol-5-ylamino)pyrimidin-4-yl)-1H-pyrrol-3-yl)methyl)azetidin-3-ol; Compound 52, described in PCT/US2010/056583)

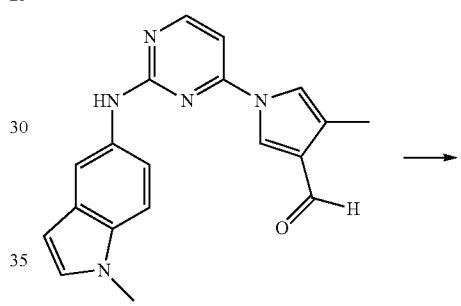

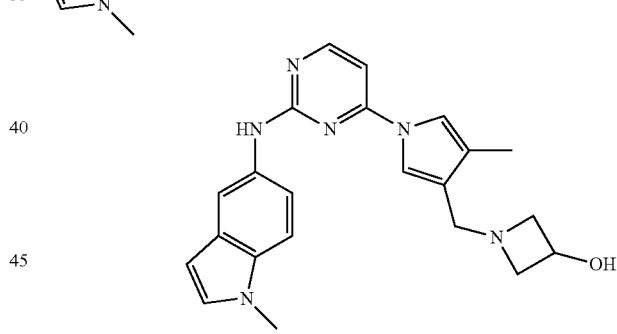

Compound 52

MS (ESI) m/z 389 [M+H]+

Preparation of 1-((3-methyl-1-(2-(1-methyl-1H-indol-5-ylamino)pyrimidin-4-yl)-1H-pyrazol-4-yl)methyl)azetidin-3-ol; Compound 140

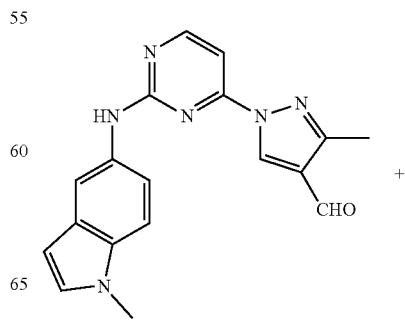

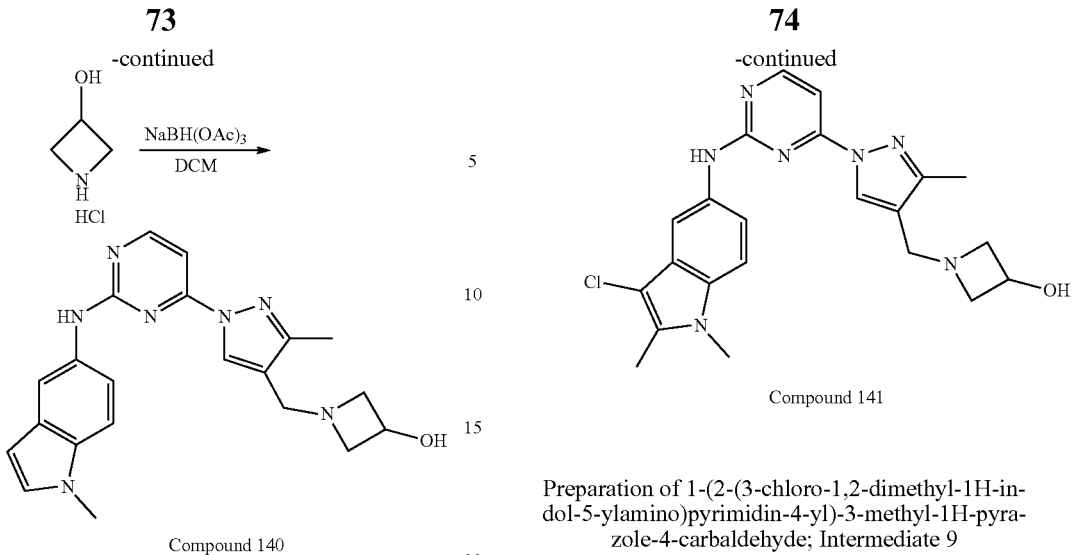

Compound 140

To a slurry of intermediate 8 (77 mg, 0.23 mmol), 3-azetidinole hydrochloride (50 mg, 2 equiv.) and triethylamine (30 mL, 1 equiv.) in 20 mL of dichloromethane, was added NaBH(OAc)$_3$ (146 mg, 3 equiv.) at room temperature. The reaction was stirred for 15 hour at room temperature and then quenched with 1N—NaOH. It was extracted with ethyl acetate and washed twice with brine. The collected organic layer was dried over anhydrous sodium sulfate and then concentrated in vacuo. The resulting residue was purified by recrystallization in a mixture of ethyl acetate and heptanes to afford desired Compound No. 140 as a pale yellow solid (62 mg, 69%); MS (ESI) m/z 390 [M+H]$^+$.

Method 2: Preparation of 1-((1-(2-(3-chloro-1,2-dimethyl-1H-indol-5-ylamino)pyrimidin-4-yl)-3-methyl-1H-pyrazol-4-yl)methyl)azetidin-3-ol; Compound 141

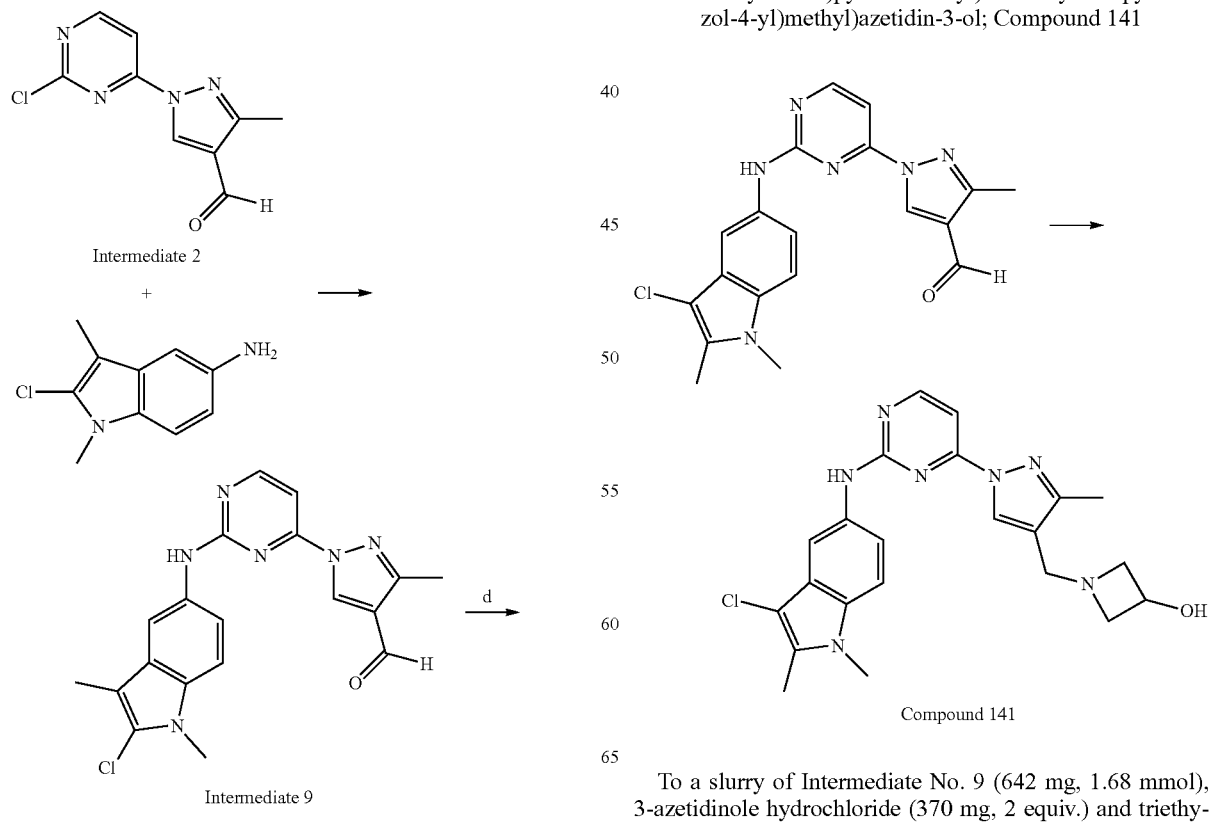

Preparation of 1-(2-(3-chloro-1,2-dimethyl-1H-indol-5-ylamino)pyrimidin-4-yl)-3-methyl-1H-pyrazole-4-carbaldehyde; Intermediate 9

A round bottomed flask was charged with 1-(2-chloropyrimidin-4-yl)-3-methyl-1H-pyrazole-4-carbaldehyde (574 mg, 2.58 mmol), 2-chloro-1,3-dimethyl-1H-indol-5-amine (502 mg, 1.0 equiv.), potassium carbonate (1.1 g, 3.0 equiv), palladium acetate (58 mg, 0.1 equiv.), Xantphos (298 mg, 0.2 equiv.) and 50 mL of anhydrous dioxane. After being degassed by nitrogen bubbling, the reaction mixture was heated at 100° C. for 3 hours. Volatiles were removed in vacuo and then the resulting residue was extracted with dichloromethane. The collected organic layer was dried over anhydrous sodium sulfate and then concentrated in vacuo. The resulting residue was purified by silica gel chromatography (DCM/MeOH) to give 467 mg (48%) of the desired intermediate 9 as a pale yellow solid. MS (ESI) m/z 381 [M+H]$^+$.

Preparation of -((1-(2-(3-chloro-1,2-dimethyl-1H-indol-5-ylamino)pyrimidin-4-yl)-3-methyl-1H-pyrazol-4-yl)methyl)azetidin-3-ol; Compound 141

To a slurry of Intermediate No. 9 (642 mg, 1.68 mmol), 3-azetidinole hydrochloride (370 mg, 2 equiv.) and triethylamine (1.4 mL, 6 equiv.) in 100 mL of dichloromethane, was added NaBH(OAc)$_3$ (1.07 g, 3 equiv.) at room temperature. The reaction was stirred for 12 hour at room temperature and then quenched with 1N—NaOH. It was extracted with ethyl acetate and washed twice with brine. The collected organic layer was dried over anhydrous sodium sulfate and then concentrated in vacuo. The resulting residue was purified by silica gel chromatography (DCM/MeOH) to afford desired Compound No. 141 as a pale yellow solid (540 mg, 73%); MS (ESI) m/z 438 [M+H]$^+$; $^1$H NMR (300 MHz, DMSO-d$_3$) δ 9.72 (s, 1H), 8.59 (s, 1H), 8.52 (d, 1H, J=5.4 Hz), 7.95 (s, 1H), 7.45 (s, 2H), 7.14 (s, 1H, J=5.4 Hz), 4.41 (m, 1H), 4.05 (m, 4H), 3.70 (s, 3H), 3.35 (m, 2H), 2.42 (s, 3H), 2.34 (s, 3H).

Method 3: Preparation of (R)-1-((1-(2-(3-chloro-1-cyclopropyl-1H-indol-5-ylamino)pyrimidin-4-yl)-3-methyl-1H-pyrazol-4-yl)methyl)pyrrolidin-3-ol; Compound 142

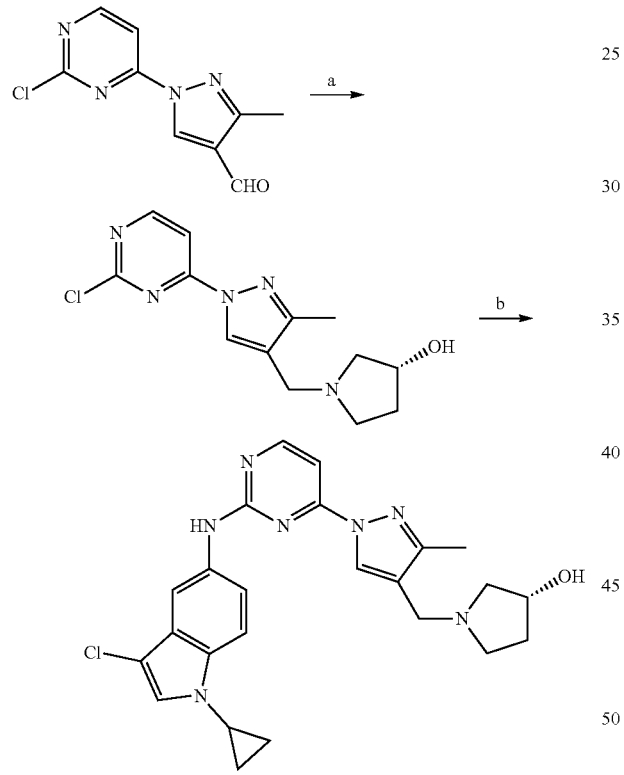

a) (R)-pyrrolidin-3-ol, NaBH(OAc)$_3$, DCM, b) 3-chloro-1-cyclopropyl-1H-indol-5-amine, Pd(OAc)$_2$, Xantphos, K$_2$CO$_3$, Dioxane To a slurry of intermediate No. 2 (440 mg, 2.0 mmol) and (R)-pyrrolidin-3-ol (250 mg, 1.5 equiv.) in 30 mL of dichloromethane, was added NaBH(OAc)$_3$ (1.3 g, 3 equiv.) at room temperature. The reaction was stirred for 5 hour at room temperature and then quenched with 1N—NaOH. It was extracted with ethyl acetate and washed twice with brine. The collected organic layer was dried over anhydrous sodium sulfate and then concentrated in vacuo. The resulting residue was purified by silica gel chromatography (heptane/ethyl acetate) to afford desired intermediate as a pale yellow solid (468 mg, 80%).

A round bottomed flask was charged with (R)-1-((1-(2-chloropyrimidin-4-yl)-3-methyl-1H-pyrazol-4-yl)methyl) pyrrolidin-3-ol (268 mg, 1.6 mmol), 3-chloro-1-cyclopropyl-1H-indol-5-amine (430 mg, 1.3 equiv.), potassium carbonate (0.66 g, 3.0 equiv), palladium acetate (18 mg, 0.05 equiv.), Xantphos (0.1 equiv.) and 50 mL of anhydrous dioxane. After being degassed by nitrogen bubbling, the reaction mixture was heated at 100° C. for 5 hours. Volatiles were removed in vacuo and then the resulting residue was extracted with dichloromethane. The collected organic layer was dried over anhydrous sodium sulfate and then concentrated in vacuo. The resulting residue was purified by silica gel chromatography (DCM/MeOH) to give 519 mg (70%) of the desired Compound 142 as a pale yellow solid. MS (ESI) m/z 464 [M+H]$^+$.

Method 4: Preparation of 1-((3-methyl-1-(2-(1-methyl-1H-indol-5-ylamino)pyrimidin-4-yl)-1H-pyrazol-4-yl)methyl)azetidin-3-ol; Compound 143

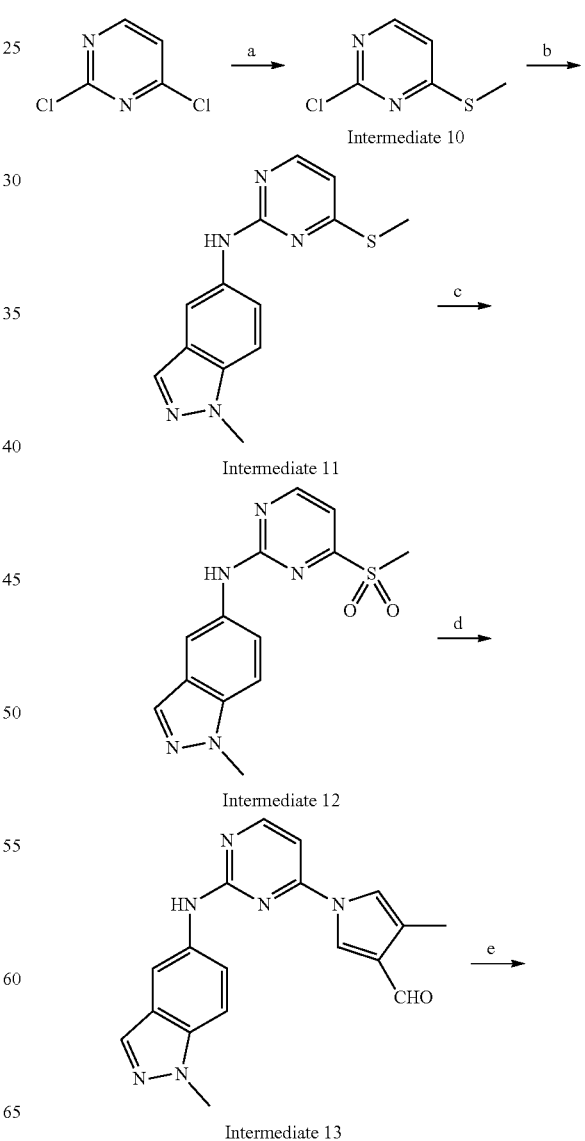

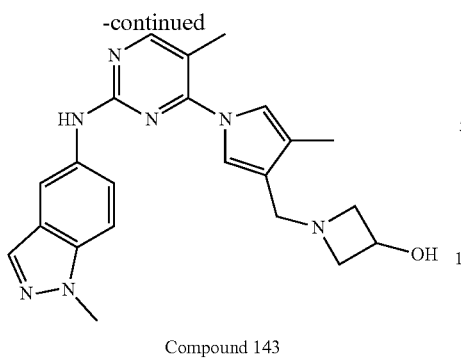

Compound 143

1) MeSNa, THF, b) Aniline delivatives, H⁺, EtOH, c) mCPBA, DCM, d) R₆Amine, NaBH(OAC)₃

Preparation of 2-chloro-4-(methylthio)pyrimidine; Intermediate 10

To a solution of ethyl 2,4-dichloropyrimidine (20.0 g, 0.13 mol) in 150 mL of anhydrous tetrahydrofurane was added sodium thiomethoxide (49.30 mL, 0.15 mol) at −10° C. The reaction mixture was allowed to warm up to room temperature and then stirred for 5 hours with monitoring a reaction with LC-MS or thin layer chromatography (TLC). The reaction mixture was diluted with ethyl acetate and washed with brine (×2). The collected organic layer was dried over anhydrous sodium sulfate and then concentrated in vacuo. The resulting solid was slurrified with diethyl ether and then collected by filtration to afford the desired intermediate 10 as a white solid (11.2 g, 52%)

Preparation of 1-methyl-N-(4-(methylsulfonyl)pyrimidin-2-yl)-1H-indazol-5-amine; Intermediate 12

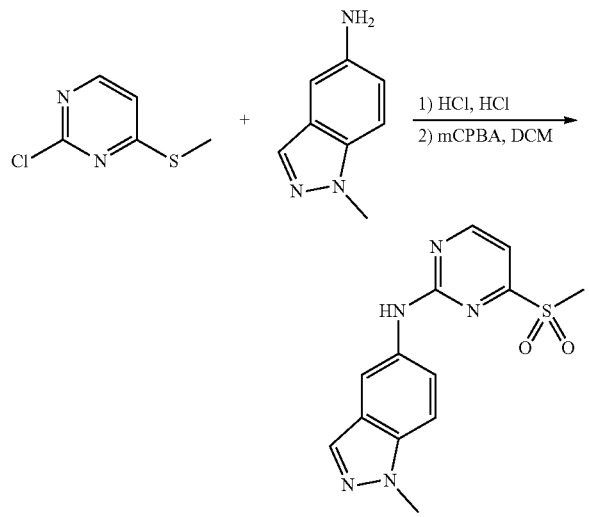

To a solution of 2-chloro-4-(methylthio)pyrimidine (1.0 g, 6.2 mmol) and 1-methyl-1H-indazol-5-amine (1.0 g, 6.8 mmol) in 10 mL of ethanol was added 1 mL of concentrated hydrochloric acid at room temperature. The reaction mixture was heated at 80° C. for 5 hours with monitoring a reaction with LC-MS or thin layer chromatography (TLC). The reaction mixture was cooled to room temperature to form a solid. The resulting solid was collected by filtration and rinsed with cold ethanol to afford 1-methyl-N-(4-(methylthio)pyrimidin-2-yl)-1H-indazol-5-amine, intermediate 11 (0.7 g, 41%). The resulting solid was dissolved in 20 mL of dichloromethane and treated with m-chloroperbenzoic acid (mCPBA, 0.9 g, 5.2 mmol) at room temperature. After being stirred for 12 hours at room temperature, the reaction mixture was extracted with dichloromethane (×3) and washed with brine. The collected organic layer was dried over anhydrous sodium sulfate and then concentrated in vacuo. The resulting solid was slurrified with heptane and then collected by filtration to afford the desired intermediate 12 as a white solid (0.6 g, 77%).

Preparation of 4-methyl-1-(2-(1-methyl-1H-indazol-5-ylamino)pyrimidin-4-yl)-1H-pyrrole-3-carbaldehyde; Intermediate 13

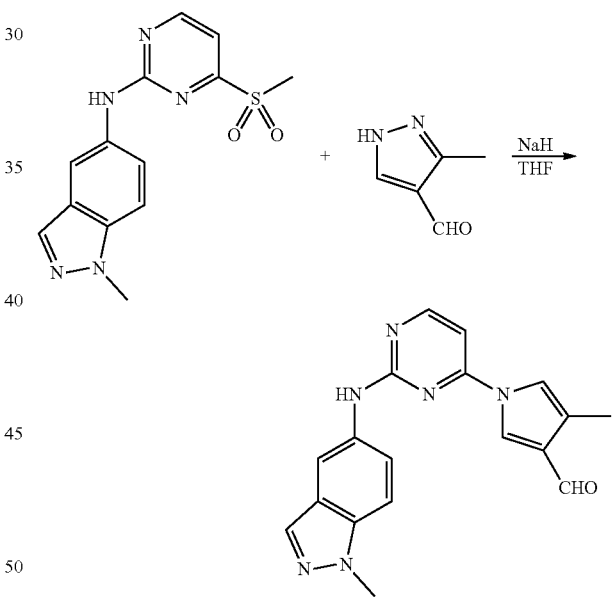

To a solution of 3-methyl-1H-pyrazole-4-carbaldehyde, intermediate 12 (0.33 g, 3.0 mmol) in 10 mL of THF was added 0.12 g of 60% sodium hydride with ice bath cooling and then it was stirred for 20 minute at the same temperature. To this, was added of 10 mL solution of 1-methyl-N-(4-(methansulfonyl)pyrimidin-2-yl)-1H-indazol-5-amine (0.6 g, 2.0 mmol) in THF. The reaction was allowed to warm up to room temperature and then stirred for 2 hours at rt. The reaction was quenched with water, extracted with dichloromethane (×2) and washed with brine. The collected organic layers were dried over anhydrous sodium sulfate and then concentrated in vacuo. The resulting residue was solidified with heptane and then collected by filtration to afford the desired intermediate 13 as a white solid (0.45 g, 66%).

Preparation of 1-((4-methyl-1-(2-(1-methyl-1H-indazol-5-ylamino)pyrimidin-4-yl)-1H-pyrrol-3-yl)methyl)azetidin-3-ol; Compound 143

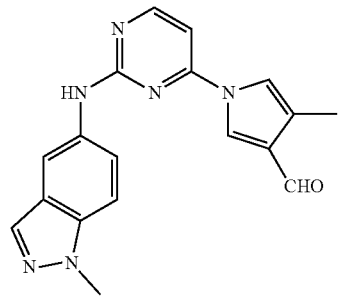

+

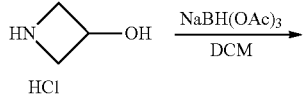

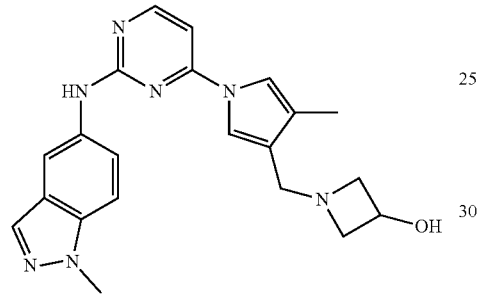

To a slurry of intermediate 13 (0.45 g, 1.3 mmol), 3-azetidinol hydrochloride (0.3 g, 2.7 mmol) and triethylamine (0.76 mL) in 50 mL of dichloromethane, was added NaBH(OAc)₃ (0.86 g, 4.5 mmol) at room temperature. The reaction was stirred for 12 hour at room temperature and then quenched with 1N—NaOH. It was extracted with dichloromethane (×2) and washed with brine. The collected organic layers were dried over anhydrous sodium sulfate and then concentrated in vacuo. The resulting residue was purified by column chromatography to afford desired Compound No. 143 as a pale yellow solid (0.27 g, 51%); MS (ESI) m/z 391 [M+H]$^+$.]$^+$; $^1$H NMR (300 MHz, DMSO-d$_6$) δ 9.75 (s, 1H), 8.48 (d, 1H, J=5.4 Hz), 8.30 (s, 1H), 8.21 (s, 1H), 7.99 (s, 1H), 7.62 (m, 2H), 7.12 (d, 1H, J=5.4 Hz), 5.34 (m, 1H), 4.19 (m, 1H), 4.04 (s, 3H), 3.49 (m, 2H), 3044 (s, 2H), 2.77 (m, 2H), 2.29 (m, 3H).

Preparation of Compound 144 to Compound 267

The following compounds were prepared by a method similar to that described for preparations of Compound No. 140 (Method I), Compound No. 141 (Method 2) Compound No. 143 (Method 2) or Compound No. 143 (method 3) using the appropriate 2-amino substituted pyrimidinyl aldehyde and the appropriate amine with or without base by reductive amination.

1-((1-(2-(3-Chloro-1-methyl-1H-indol-5-ylamino)pyrimidin-4-yl)-3-methyl-1H-pyrazol-4-yl)methyl)azetidin-3-ol; Compound 144

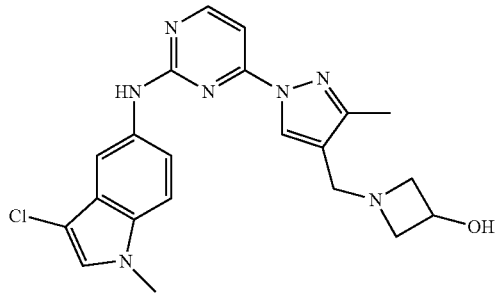

MS (ESI) m/z 424 [M+H]$^+$; $^1$H NMR (300 MHz, DMSO-d$_6$) δ 9.76 (s, 1H), 8.81 (d, 1H, J=5.4 Hz), 8.47 (s, 1H), 7.5 (s, 1H), 7.46 (s, 2H), 7.13 (d, 1H, J=5.4 Hz), 4.31 (s, 1H), 3.78 (s, 3H), 3.48 (m, 2H), 2.73 (m, 2H), 2.44 (m, 2H), 2.29 (s, 3H).

1-((3-Methyl-1-(2-(1,2,3-trimethyl-1H-indol-5-ylamino)pyrimidin-4-yl)-1H-pyrazol-4-yl)methyl)azetidin-3-ol; Compound 145

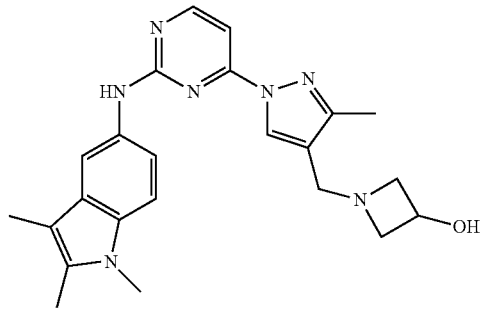 [SMILES: Cc1nn(-c2ccnc(Nc3ccc4c(c3)c(C)c(C)n4C)n2)cc1CN1CC(O)C1]

MS (ESI) m/z 418 [M+H]$^+$; $^1$H NMR (300 MHz, CDCl₃) δ 8.50 (s, 1H), 8.35 (d, 1H, J=5.4 Hz), 7.67 (s, 1H), 7.27 (m, 2H), 7.14 (d, 1H, J=5.4 Hz), 4.48 (m, 1H), 3.88 (m, 2H), 3.67 (s, 3H), 3.37 (s, 2H), 3.26 (m, 2H), 2.37 (s, 6H), 2.26 (s, 3H).

1-((1-(2-(1-Isopropyl-2,3-dimethyl-1H-indol-5-ylamino)pyrimidin-4-yl)-3-methyl-1H-pyrazol-4-yl)methyl)azetidin-3-ol; Compound 146

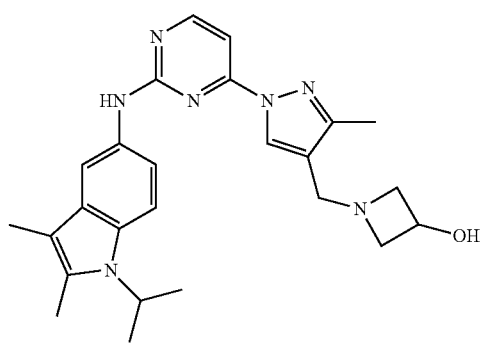 [SMILES: Cc1nn(-c2ccnc(Nc3ccc4c(c3)c(C)c(C)n4C(C)C)n2)cc1CN1CC(O)C1]

MS (ESI) m/z 446 [M+H]⁺; ¹H NMR (300 MHz, DMSO-d₆) δ 9.51 (s, 1H), 8.44 (d, 1H, J=5.4 Hz), 8.31 (s, 1H), 7.94 (s, 1H), 7.45 (d, 1H, J=8.8 Hz), 7.20~7.17 (m, 1H), 7.06 (d, 1H, J=5.4 Hz,), 5.32 (d, 1H, J=6.46 Hz), 4.69-4.64 (m, 1H), 4.21~4.15 (m, 1H), 3.51~3.43 (m, 4H), 2.74 (t, 2H, J=7.5 Hz), 2.35 (s, 3H), 2.23 (s, 3H), 2.21 (s, 3H), 1.54 (d, 6H, J=6.9H).

1-((1-(2-(3-Bromo-1-methyl-1H-indol-5-ylamino) pyrimidin-4-yl)-3-methyl-1H-pyrazol-4-yl)methyl) azetidin-3-ol; Compound 147

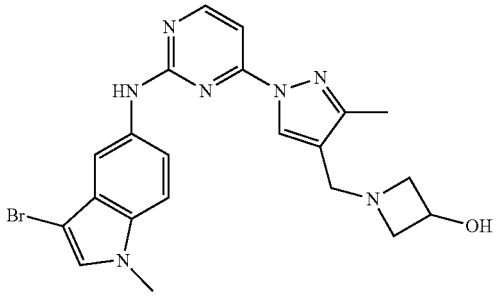

MS (ESI) m/z 468 [M+H]⁺, 470 [M+2+H]⁺; ¹H NMR (300 MHz, DMSO-d₆) δ 9.79 (s, 1H), 8.50 (d, 1H, J=5.4 Hz), 8.42 (s, 1H), 8.22 (s, 1H), 7.54 (s, 1H), 7.48~7.38 (m, 2H), 7.13 (d, 1H, J=5.4 Hz), 5.34 (d, 1H, J=6.2 Hz,), 4.22~4.15 (m, 1H), 3.50~3.41 (m, 4H), 2.75 (s, 2H), 2.25 (s, 3H).

Cyclopropyl(5-(4-(4-((3-hydroxyazetidin-1-yl)methyl)-3-methyl-1H-pyrazol-1-yl)pyrimidin-2-ylamino)-1H-indol-1-yl)methanone; Compound 148

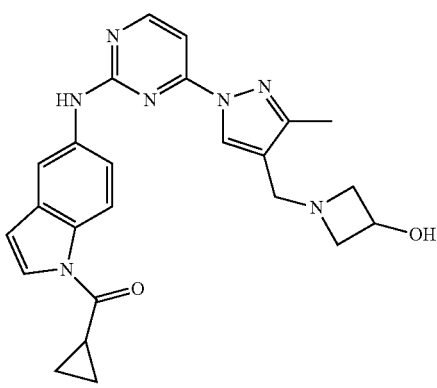 [SMILES: Cc1nn(-c2ccnc(Nc3ccc4c(ccn4C(=O)C4CC4)c3)n2)cc1CN1CC(O)C1]

MS (ESI) m/z 444 [M+H]⁺; ¹H NMR (300 MHz, CDCl₃) δ 8.33~8.38 (m, 3H), 7.91 (d, 1H, J=5.4 Hz,), 7.71 (d, 1H, J=3.9 Hz), 7.41~7.48 (m, 1H), 7.19 (d, 1H, J=5.7 Hz), 6.69 (d, J=3.9 Hz, 1H), 4.38~4.44 (m, 1H), 3.61~3.66 (m, 2H), 3.52 (s, 2H), 2.96~3.01 (m, 2H), 2.30 (s, 3H), 1.30~1.32 (m, 2H), 1.09~1.11 (m, 2H).

1-((1-(2-(1-(2-Methoxyethyl)-1H-indol-5-ylamino) pyrimidin-4-yl)-3-methyl-1H-pyrazol-4-yl)methyl) azetidin-3-ol; Compound 149

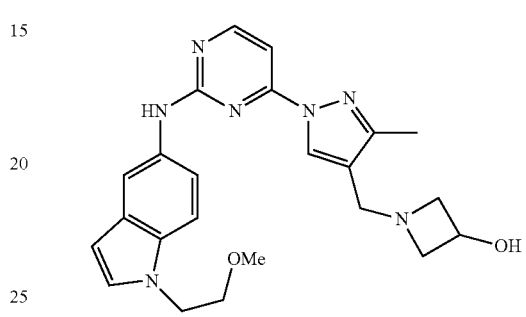

MS (ESI) m/z 434 [M+H]⁺; ¹H NMR (300 MHz, DMSO-d₆) δ 9.53 (s, 1H), 8.45 (d, 1H, J=5.4 Hz), 8.28 (s, 1H), 7.95 (s, 1H), 7.45~7.32 (m, 3H), 7.07 (d, 1H, J=5.4 Hz), 6.38 (d, 1H, J=3.0 Hz), 5.34 (d, 1H, J=6.5 Hz), 4.32 (t, 2H, J=5.3 Hz), 4.23~4.16 (m, 1H), 3.66 (t, 2H, J=5.3 Hz), 3.53~3.45 (m, 4H), 3.23 (s, 3H), 2.77 (s, 2H), 2.23 (s, 3H).

1-((1-(2-(3-Chloro-1-cyclopropyl-1H-indol-5-ylamino)pyrimidin-4-yl)-3-methyl-1H-pyrazol-4-yl) methyl)azetidin-3-ol; Compound 150

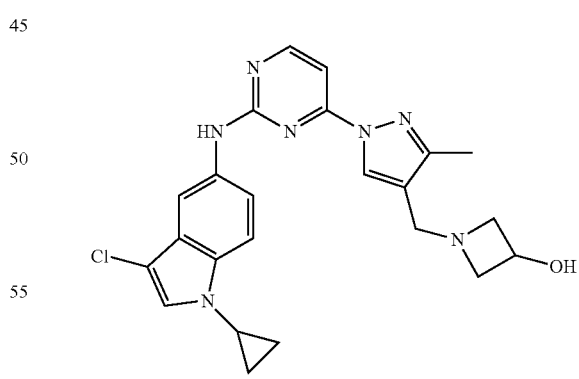

MS (ESI) m/z 450 [M+H]⁺; ¹H NMR (300 MHz, DMSO-d₆) δ 9.77 (s, 1H), 8.49 (d, 1H, J=5.4 Hz), 8.35 (s, 1H), 8.20 (s, 1H), 7.53 (t, J=8.94 Hz, 2H), 7.47~7.43 (m, 1H), 7.12 (d, 1H, J=5.4 Hz), 5.30 (d, 1H, J=6.4 Hz), 4.19~4.17 (m, 1H), 3.52~3.47 (m, 4H), 3.46~3.41 (m, 2H), 2.76~2.71 (m, 2H), 2.24 (s, 3H), 1.06~1.00 (m, 4H).

2,2,2-Trifluoro-1-(5-(4-(4-((3-hydroxyazetidin-1-yl)methyl)-3-methyl-1H-pyrazol-1-yl)pyrimidin-2-ylamino)-1-methyl-1H-indol-3-yl)ethanone; Compound 151

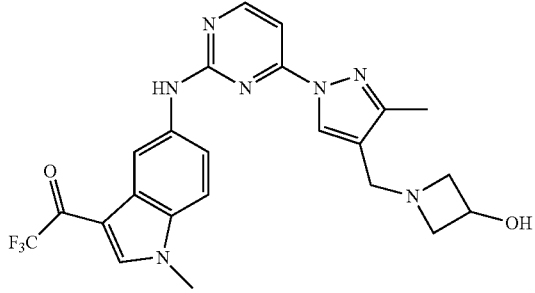 [SMILES: Cc1nn(-c2ccnc(Nc3ccc4c(c3)c(C(=O)C(F)(F)F)cn4C)n2)cc1CN1CC(O)C1]

MS (ESI) m/z 486 [M+H]⁺; ¹H NMR (300 MHz, CDCl₃) δ 9.39 (s, 1H), 9.23 (s, 1H), 8.39 (d, 1H, J=5.7 Hz), 7.94 (s, 1H), 7.23~7.38 (m, 3H), 4.42~4.46 (m, 1H), 3.91 (s, 7H), 3.46~3.51 (m, 2H), 2.39 (s, 3H).

1-(5-(4-(4-((3-Hydroxyazetidin-1-yl)methyl)-3-methyl-1H-pyrazol-1-yl)pyrimidin-2-ylamino)-1-methyl-1H-indol-3-yl)ethanone; Compound 152

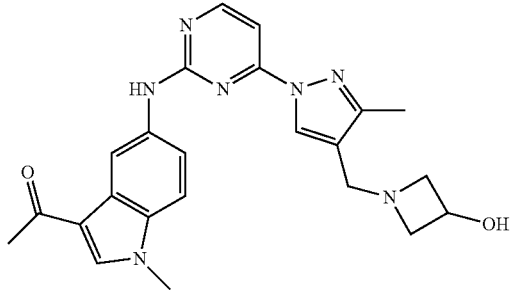 [SMILES: CC(=O)c1cn(C)c2ccc(Nc3nccc(-n4cc(CN5CC(O)C5)c(C)n4)n3)cc12]

MS (ESI) m/z 432 [M+H]⁺; ¹H NMR (300 MHz, CDCl₃) δ 8.93 (br s, 1H), 8.75 (s, 1H), 8.36 (d, 1H, J=5.7 Hz), 7.73 (s, 1H), 7.30~7.35 (m, 2H), 7.20 (d, 1H, J=5.7 Hz), 4.33~4.39 (m, 1H), 3.85 (s, 3H), 3.60~3.65 (m, 4H), 3.06~3.11 (m, 2H), 2.53 (s, 3H), 2.33 (s, 3H).

1-((3-Methyl-1-(2-(1-(methylsulfonyl)-1H-indol-5-ylamino)pyrimidin-4-yl)-1H-pyrazol-4-yl)methyl)azetidin-3-ol; Compound 153

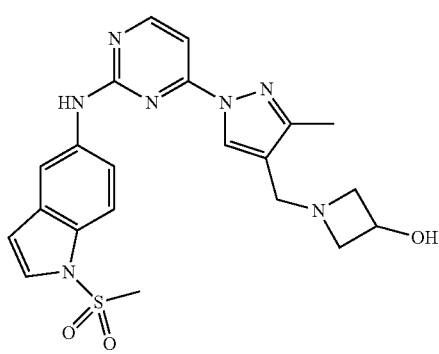 [SMILES: Cc1nn(-c2ccnc(Nc3ccc4c(ccn4S(C)(=O)=O)c3)n2)cc1CN1CC(O)C1]

MS (ESI) m/z 454 [M+H]⁺; ¹H NMR (300 MHz, DMSO-d₆) δ 9.82 (s, 1H), 8.51 (d, J=5.4 Hz, 1H), 8.32 (s, 1H), 8.15 (s, 1H) 7.80 (d, 1H, J=8.96 Hz), 7.68~7.64 (m, 1H), 7.56 (d, 1H, J=3.6 Hz,), 7.15 (d, J=5.4 Hz, 1H), 6.84 (d, 1H, J=3.6 Hz), 5.33 (d, J=6.4 Hz,), 4.23~4.17 (m, 1H), 3.53~3.46 (m, 4H), 3.40 (s, 3H), 2.78 (t, J=6.4 Hz, 2H), 2.24 (s, 3H).

5-(4-(4-((3-Hydroxyazetidin-1-yl)methyl)-3-methyl-1H-pyrazol-1-yl)pyrimidin-2-ylamino)-N,N,1-trimethyl-1H-indole-3-carboxamide; Compound 154

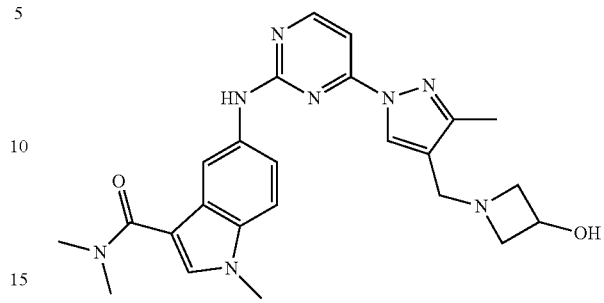

MS (ESI) m/z 462 [M+H]⁺; ¹H NMR (300 MHz, CDCl₃) δ 8.50 (s, 1H), 8.36 (d, 1H, J=5.4 Hz), 8.24 (s, 1H), 7.72 (s, 1H), 7.37 (s, 1H), 7.25~7.30 (m, 2H), 7.16 (d, 1H, J=5.4 Hz), 4.42 (m, 1H), 3.79 (s, 3H), 3.60~3.68 (m, 2H), 3.61 (s, 2H), 3.00-3.30 (m, 8H), 2.29 (s, 3H).

(5-(4-(4-((3-Hydroxyazetidin-1-yl)methyl)-3-methyl-1H-pyrazol-1-yl)pyrimidin-2-ylamino)-1-methyl-1H-indol-3-yl)(morpholino)methanone; Example 155

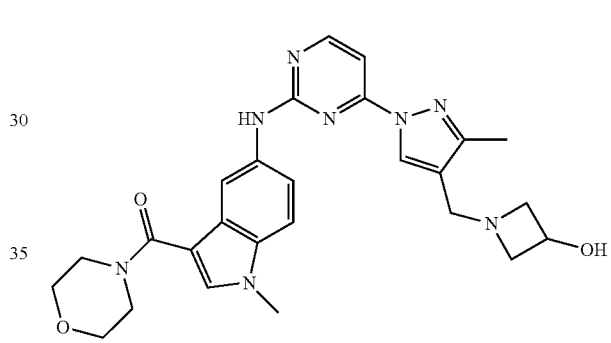

MS (ESI) m/z 503 [M+H]⁺; ¹H NMR (300 MHz, CDCl₃) δ 8.40 (d, 1H, J=5.4 Hz), 8.38 (s, 1H), 8.21 (s, 1H), 7.55 (s, 1H), 7.47 (s, 1H), 7.32 (d, 1H, J=8.7 Hz), 7.24 (d, 1H, J=8.7 Hz), 7.22 (d, 1H, J=5.4 Hz), 4.36~4.42 (m, 1H), 3.83 (s, 3H), 3.75 (br s, 8H), 3.53~3.59 (m, 2H), 3.51 (s, 2H), 3.00~3.05 (m, 2H), 2.31 (s, 3H).

1-((1-(2-(3-Bromo-1,2-dimethyl-1H-indol-5-ylamino)pyrimidin-4-yl)-3-methyl-1H-pyrazol-4-yl)methyl)azetidin-3-ol; Compound 156

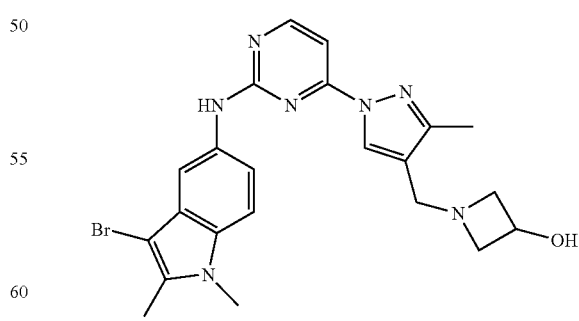

MS (ESI) m/z 482 [M+H]⁺, 484 [M+2+H]⁺; ¹H NMR (300 MHz, DMSO-d₆) δ 9.74 (s, 1H), 8.49 (d, 1H, J=5.4 Hz), 8.41 (s, 1H), 8.15 (s, 1H), 7.43 (d, 1H, J=8.8 Hz,), 7.34~7.30 (m, 1H), 7.11 (d, 1H, J=5.4 Hz,), 5.33 (d, 1H, J=6.4 Hz,), 4.22~4.15 (m, 1H), 3.72 (s, 3H), 3.52~3.45 (m, 4H), 2.74 (s, 2H), 2.43 (s, 3H), 2.25 (s, 3H).

(5-(4-(4-((3-Hydroxyazetidin-1-yl)methyl)-3-methyl-1H-pyrazol-1-yl)pyrimidin-2-ylamino)-1,2-dimethyl-1H-indol-3-yl)(pyrrolidin-1-yl)methanone; Compound 157

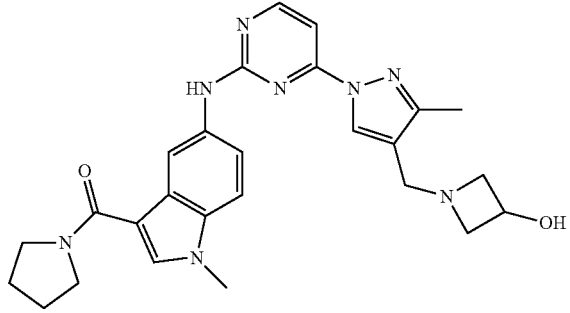 [SMILES: Cc1nn(-c2ccnc(Nc3ccc4c(c3)c(C(=O)N3CCCC3)cn4C)n2)cc1CN1CC(O)C1]

MS (ESI) m/z 487 [M+H]+; 1H NMR (300 MHz, CDCl3) δ 8.70 (s, 1H), 8.66 (s, 1H), 8.39 (d, 1H, J=5.4 Hz), 7.43 (s, 1H), 7.32 (d, 2H, J=8.4 Hz), 7.21 (d, 1H, J=5.4 Hz), 4.40~4.48 (m, 1H), 3.80~3.85 (s, 3H), 3.55~3.80 (m, 8H), 3.1-3.18 (m, 2H), 2.35 (s, 3H), 1.90~1.99 (m, 4H).

Cyclopropyl(5-(4-(4-((3-hydroxyazetidin-1-yl)methyl)-3-methyl-1H-pyrazol-1-yl)pyrimidin-2-ylamino)-1-methyl-1H-indol-3-yl)methanone; Compound 158

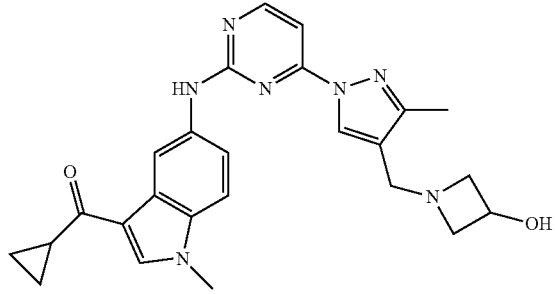 [SMILES: Cc1nn(-c2ccnc(Nc3ccc4c(c3)c(C(=O)C3CC3)cn4C)n2)cc1CN1CC(O)C1]

MS (ESI) m/z 458 [M+H]+; 1H NMR (300 MHz, CDCl3) δ 8.91 (s, 1H), 8.82 (s, 1H), 8.39 (d, 1H, J=5.4 Hz), 7.86 (s, 1H), 7.28~7.32 (m, 2H), 7.10 (39 (d, 1H, J=5.4 Hz), 4.28~4.34 (m, 1H), 3.85 (s, 3H), 3.60~3.68 (m, 2H), 3.60 (s, 2H), 3.10~3.15 (m, 2H), 2.38~2.43 (m, 1H), 2.27 (s, 3H), 1.08~1.12 (m, 2H), 0.90~0.94 (m, 2H).

1-((3-Methyl-1-(2-(1-methyl-3-(pyrrolidin-1-ylsulfonyl)-1H-indol-5-ylamino)pyrimidin-4-yl)-1H-pyrazol-4-yl)methyl)azetidin-3-ol; Compound 159

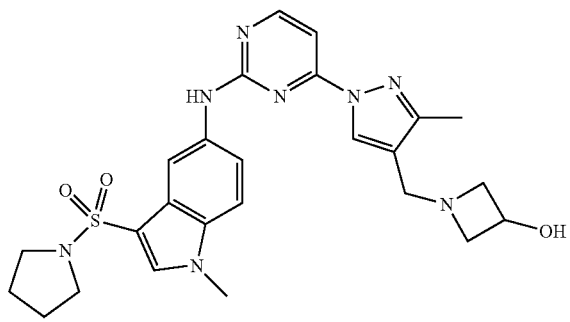 [SMILES: Cc1nn(-c2ccnc(Nc3ccc4c(c3)c(S(=O)(=O)N3CCCC3)cn4C)n2)cc1CN1CC(O)C1]

MS (ESI) m/z 523 [M+H]+; 1H NMR (300 MHz, CDCl3) δ 8.84 (s, 2H), 8.41 (d, 1H, J=5.7 Hz,), 7.63 (s, 1H), 7.20~7.37 (m, 4H), 4.41~4.45 (m, 1H), 3.89 (s, H), 3.72~3.77 (m, 2H), 3.68 (s, 2H), 3.28~3.33 (m, 4H), 3.19~3.22 (m, 2H), 2.37 (s, 3H), 1.73~1.77 (m, 4H).

1-((3-Methyl-1-(2-(1-methyl-1H-indazol-5-ylamino)pyrimidin-4-yl)-1H-pyrazol-4-yl)methyl)azetidin-3-ol; Compound 160

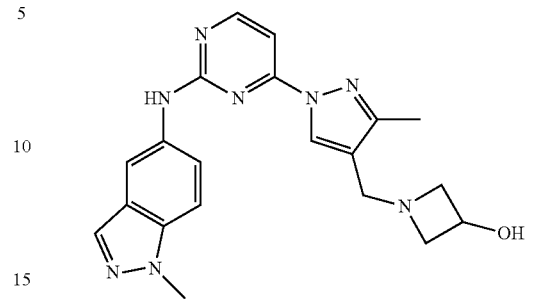

MS (ESI) m/z 391 [M+H]+; 1H NMR (300 MHz, DMSO-D6) δ 9.75 (s, 1H), 8.48 (d, 1H, J=5.4 Hz), 8.30 (s, 1H), 8.21 (s, 1H), 7.99 (s, 1H), 7.58~7.63 (m, 2H), 7.12 (d, 1H, J=5.4 Hz), 5.30~5.35 (m, 1H), 4.15~4.20 (m, 1H), 4.04 (s, 3H), 3.45~3.50 (m, 2H), 3.44 (s, 2H), 2.72~2.80 (m, 2H), 2.23 (s, 3H).

1-((1-(2-(3-Chloro-1-methyl-1H-indazol-5-ylamino)pyrimidin-4-yl)-3-methyl-1H-pyrazol-4-yl)methyl)azetidin-3-ol; Compound 161

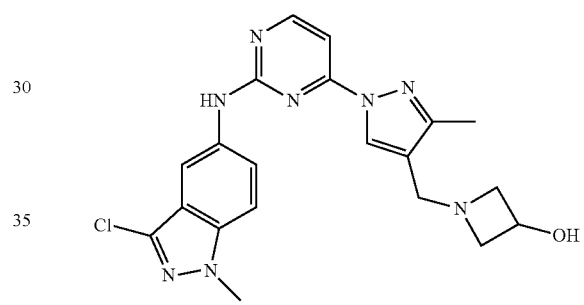

MS (ESI) m/z 425 [M+H]+; 1H NMR (300 MHz, CDCl3) δ 9.95 (s, 1H), 8.54 (d, 1H, J=5.4 Hz), 8.35 (s, 1H), 8.32 (s, 1H), 7.67 (s, 2H), 7.17 (d, 1H, J=5.4 Hz), 5.31 (d, 1H, J=6.3 Hz), 4.20~4.18 (m, 1H), 4.02 (s, 3H), 3.53~3.49 (m, 2H), 3.41 (s, 2H), 2.77~2.72 (m, 2H), 2.24 (s, 3H).

1-((1-(2-(1-Cyclopropyl-1H-indazol-5-ylamino)pyrimidin-4-yl)-3-methyl-1H-pyrazol-4-yl)methyl)azetidin-3-ol; Compound 162

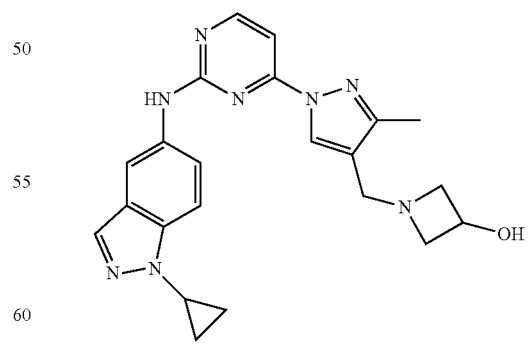

MS (ESI) m/z 417 [M+H]+; 1H NMR (300 MHz, CDCl3) δ 9.75 (s, 1H), 8.48 (d, 1H, J=5.4 Hz), 8.30 (s, 1H), 8.20 (s, 1H), 7.96 (s, 1H), 7.66 (s, 2H), 7.12 (d, 1H, J=5.4 Hz), 5.32 (d, 1H, J=6.1 Hz), 4.20~4.18 (m, 1H), 3.77~3.70 (m, 2H), 3.52~3.47 (m, 2H), 3.45 (s, 2H), 2.79~2.75 (m, 2H), 2.24 (s, 3H), 1.13~1.11 (m, 4H).

87

1-((1-(2-(3-Chloro-1-isopropyl-1H-indazol-5-ylamino)pyrimidin-4-yl)-3-methyl-1H-pyrazol-4-yl)methyl)azetidin-3-ol; Compound 163

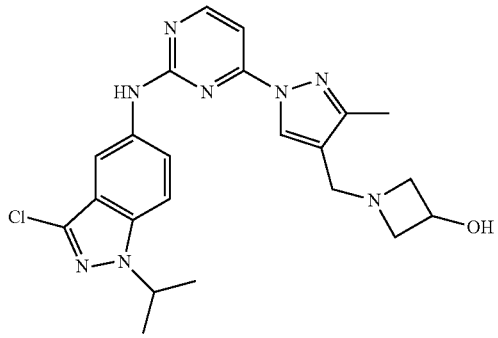 [SMILES: Cc1nn(-c2ccnc(Nc3ccc4c(c3)c(Cl)nn4C(C)C)n2)cc1CN1CC(O)C1]

MS (ESI) m/z 453 [M+H]$^+$; $^1$H NMR (300 MHz, DMSO-D$_6$) δ 9.99 (s, 1H), 8.64 (s, 1H), 8.59-8.57 (d, 1H, J=5.4 Hz), 8.17 (s, 1H), 7.78~7.70 (m, 2H), 7.20 (d, 1H, J=5.4 Hz), 6.17 (s, 1H), 4.99~4.91 (m, 1H), 4.47~4.46 (m, 1H), 4.32~4.12 (m, 4H), 3.73~3.60 (m, 2H), 2.36 (s, 3H), 1.47 (d, 6H, J=6.5 Hz).

1-((1-(2-(3-Chloro-1-cyclopropyl-1H-indazol-5-ylamino)pyrimidin-4-yl)-3-methyl-1H-pyrazol-4-yl)methyl)azetidin-3-ol; Compound 164

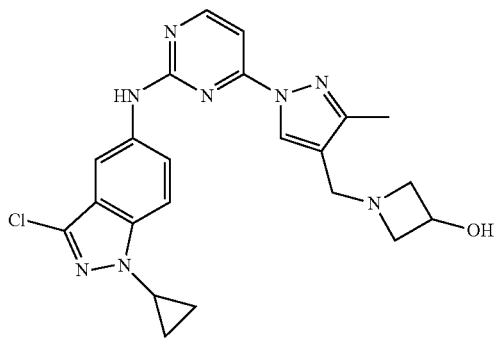 [SMILES: Cc1nn(-c2ccnc(Nc3ccc4c(c3)c(Cl)nn4C3CC3)n2)cc1CN1CC(O)C1]

MS (ESI) m/z 451 [M+H]$^+$; $^1$H NMR (300 MHz, DMSO-D$_6$) δ 9.77 (s, 1H), 8.49 (d, 1H, J=5.1 Hz), 8.35 (s, 1H), 8.20 (s, 1H), 7.53 (t, 2H, J=8.9 Hz), 7.47~7.43 (m, 1H), 7.12 (d, 1H, J=5.4 Hz), 5.30 (d, 1H, J=6.4 Hz), 4.19~4.17 (m, 1H), 3.52~3.47 (m, 4H), 3.46~3.41 (m, 2H), 2.76~2.71 (m, 2H), 2.24 (s, 3H), 1.06-1.00 (m, 4H).

1-((3-Methyl-1-(2-(1-methyl-3-morpholino-1H-indazol-5-ylamino)pyrimidin-4-yl)-1H-pyrazol-4-yl)methyl)azetidin-3-ol; Compound 165

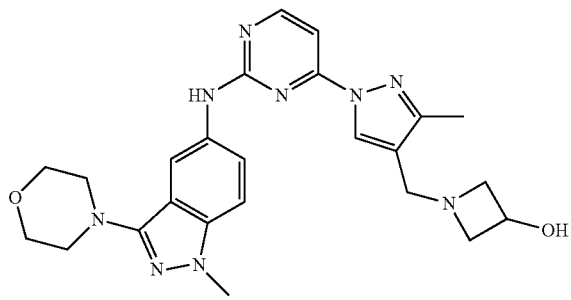 [SMILES: Cc1nn(-c2ccnc(Nc3ccc4c(c3)c(N3CCOCC3)nn4C)n2)cc1CN1CC(O)C1]

MS (ESI) m/z 476 [M+H]$^+$; $^1$H NMR (300 MHz, CDCl$_3$) δ 8.38 (d, 1H, J=5.4 Hz), 8.30 (s, 1H), 7.98 (s, 1H), 7.42~7.47 (m, 2H), 7.20~7.27 (m, 2H), 4.41~4.49 (m, 1H), 3.91~3.95 (m, 7H), 3.64~3.69 (m, 2H), 3.54 (s, 2H), 3.42~3.45 (m, 4H), 3.03~3.08 (m, 2H), 2.33 (s, 3H).

88

1-((3-Methyl-1-(2-(1-methyl-3-(pyrrolidin-1-yl)-1H-indazol-5-ylamino)pyrimidin-4-yl)-1H-pyrazol-4-yl)methyl)azetidin-3-ol; Compound 166

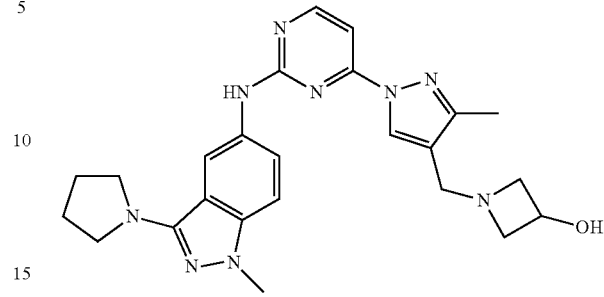

MS (ESI) m/z 460 [M+H]$^+$; $^1$H NMR (300 MHz, CDCl$_3$) δ 8.32 (d, 1H, J=5.4 Hz), 8.25 (s, 1H), 7.95 (s, 1H), 7.43 (d, 1H, J=8.7 Hz), 7.11~7.17 (m, 2H), 4.33~4.38 (m, 1H), 3.81 (s, 3H), 3.59~3.63 (m, 6H), 3.50 (s, 2H), 2.92~3.04 (m, 2H), 2.28 (s, 3H), 1.98~2.02 (m, 4H).

3-Chloro-5-(4-(4-((3-hydroxyazetidin-1-yl)methyl)-3-methyl-1H-pyrazol-1-yl)pyrimidin-2-ylamino)-N,N-dimethyl-1H-indazole-1-carboxamide; Compound 167

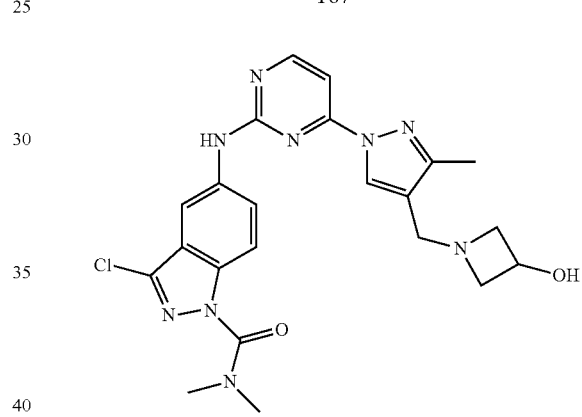

MS (ESI) m/z 482 [M+H]$^+$; $^1$H NMR (300 MHz, CDCl$_3$) δ 8.36 (d, 1H, J=5.4 Hz), 8.32 (s, 1H), 8.18 (s, 1H), 7.56 (d, 1H, J=9.0 Hz), 7.18 (d, 1H, J=5.4 Hz), 4.35 (m, 1H), 3.61 (t, 2H, J=7.5 Hz), 3.49 (s, 2H), 3.20 (s, 6H), 2.94 (t, 2H, J=7.4 Hz), 2.27 (s, 3H).

1-((3-Methyl-1-(2-(1-methylindolin-5-ylamino)pyrimidin-4-yl)-1H-pyrazol-4-yl)methyl)azetidin-3-ol; Compound 168

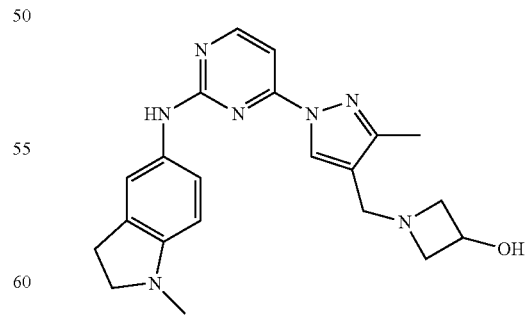

MS (ESI) m/z 392 [M+H]$^+$; $^1$H NMR (300 MHz, DMSO-d$_6$) δ 9.64 (s, 1H), 8.46 (d, 1H, J=5.4 Hz), 8.28 (s, 1H), 7.64 (s, 1H), 7.51~7.48 (m, 1H), 7.11 (d, 1H, J=5.4 Hz), 5.35 (d, 1H, J=6.4 Hz), 4.23~4.16 (m, 1H), 3.97 (t, 2H, J=8.4 Hz), 3.75 (s, 3H), 3.53~3.46 (m, 4H), 3.12 (t, 2H, J=8.5 Hz), 2.78 (s, 2H), 2.23 (s, 3H).

2,2,2-Trifluoro-1-(5-(4-(4-((3-hydroxyazetidin-1-yl)methyl)-3-methyl-1H-pyrazol-1-yl)pyrimidin-2-ylamino)indolin-1-yl)ethanone; Compound 169

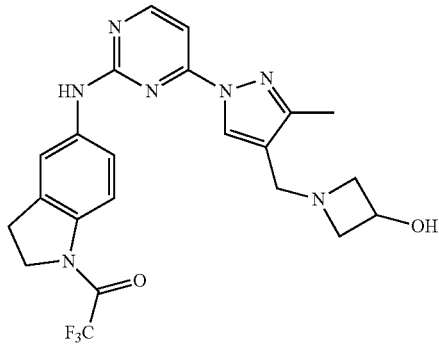 [SMILES: Cc1nn(-c2ccnc(Nc3ccc4c(c3)CCN4C(=O)C(F)(F)F)n2)cc1CN1CC(O)C1]

MS (ESI) m/z 474 [M+H]+; 1H NMR (300 MHz, DMSO-d6) δ 9.88 (s, 1H), 8.51 (d, 1H, J=5.4 Hz), 8.31 (s, 1H), 8.04 (d, J=8.8 Hz, 1H), 7.81 (s, 1H), 7.65~7.61 (m, 1H), 7.17 (d, 1H, J=5.4 Hz), 5.34 (d, 1H, J=6.4 Hz), 4.28 (t, 2H, J=7.84 Hz), 4.25~4.16 (m, 1H), 3.52~3.46 (m, 4H), 3.31~3.18 (m, 2H), 2.77 (s, 2H), 2.24 (s, 3H).

1-((3-Methyl-1-(2-(1-(methylsulfonyl)indolin-5-ylamino)pyrimidin-4-yl)-1H-pyrazol-4-yl)methyl)azetidin-3-ol; Compound 170

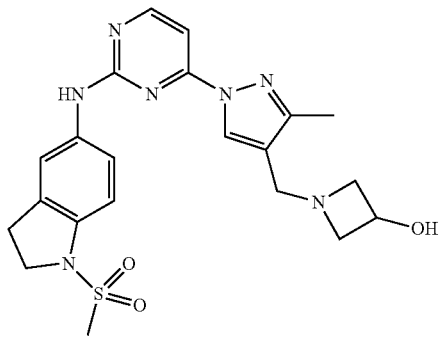 [SMILES: Cc1nn(-c2ccnc(Nc3ccc4c(c3)CCN4S(C)(=O)=O)n2)cc1CN1CC(O)C1]

MS (ESI) m/z 456 [M+H]+; 1H NMR (300 MHz, DMSO-d6) δ 9.71 (s, 1H), 8.46 (d, 1H, J=5.4 Hz), 8.29 (s, 1H), 7.71 (s, 1H), 7.54 (d, 1H, J=7.3 Hz), 7.22 (d, 1H, J=8.7 Hz), 7.12 (d, 1H, J=5.4 Hz), 5.31 (d, 1H, J=6.4 Hz), 4.22~4.16 (m, 1H), 3.94 (t, 2H, J=8.2 Hz), 3.51~3.47 (m, 2H), 3.44 (s, 2H), 3.14 (t, 2H, J=8.2 Hz), 2.96 (s, 3H), 2.78~2.74 (m, 2H), 2.23 (s, 3H).

1-((3-Methyl-1-(2-(1-methyl-3-tosyl-1H-indol-5-ylamino)pyrimidin-4-yl)-1H-pyrazol-4-yl)methyl)azetidin-3-ol; Compound 171

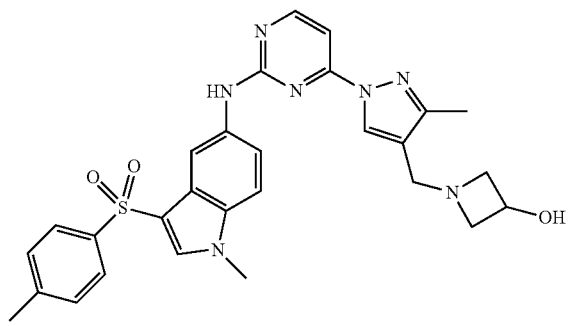 [SMILES: Cc1ccc(S(=O)(=O)c2cn(C)c3ccc(Nc4nccc(-n5cc(CN6CC(O)C6)c(C)n5)n4)cc23)cc1]

MS (ESI) m/z 544 [M+H]+; 1H NMR (300 MHz, CDCl3) δ 8.78 (s, 1H), 8.67 (s, 1H), 8.40 (d, 1H, J=5.4 Hz), 7.91 (d, 2H, J=8.1 Hz), 7.71 (m, 2H), 7.27 (m, 3H), 7.22 (d, 2H, J=8.1 Hz), 4.35~4.40 (m, 1H), 3.81 (s, 3H), 3.60~3.65 (m, 2H), 3.56 (s, 2H), 3.03-3.08 (m, 2H), 2.34 (s, 3H), 2.33 (s, 3H).

1-((3-Methyl-1-(2-(1-methyl-3-(oxazol-2-yl)-1H-indol-5-ylamino)pyrimidin-4-yl)-1H-pyrazol-4-yl)methyl)azetidin-3-ol; Compound 172

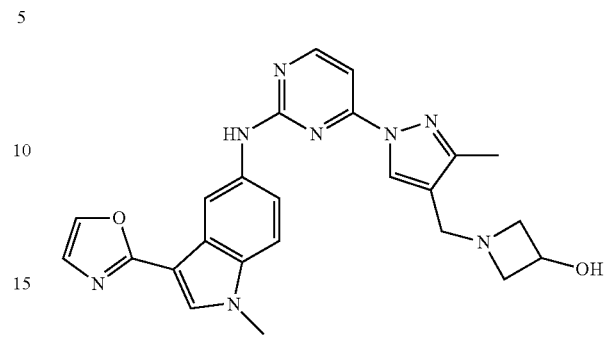

MS (ESI) m/z 457 [M+H]+; 1H NMR (300 MHz, CDCl3) δ 8.46 (s, 1H), 8.39 (s, 1H), 8.35 (d, 1H, J=5.7 Hz), 7.76 (s, 1H), 7.68 (s, 1H), 7.48 (d, 1H, J=8.7 Hz), 7.36 (d, J=8.7 Hz, 1H), 4.28~4.34 (m, 1H), 7.15~7.17 (m, 2H), 3.86 (s, 3H), 3.50~3.55 (m, 2H), 3.46 (s, 2H), 2.84~2.94 (m, 2H), 2.29 (s, 3H).

1-((1-(2-(3-Chloro-2-methylbenzofuran-5-ylamino)pyrimidin-4-yl)-3-methyl-1H-pyrazol-4-yl)methyl)azetidin-3-ol; Compound 173

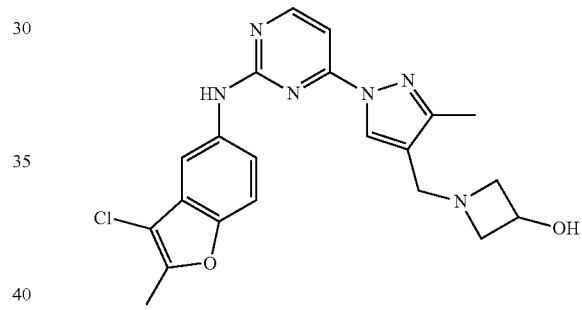

MS (ESI) m/z 425 [M+H]+; 1H NMR (300 MHz, CDCl3) δ 8.35-8.37 (m, 2H), 7.92 (br s, 1H), 7.32~7.34 (m, 2H), 7.19 (d, 1H, J=5.7 Hz), 4.36~4.40 (m, 1H), 3.63~3.66 (m, 2H), 3.61 (s, 2H), 2.98~3.00 (m, 2H), 2.45 (s, 3H), 2.30 (s, 3H).

1-((3-Methyl-1-(2-(2-methylbenzofuran-5-ylamino)pyrimidin-4-yl)-1H-pyrazol-4-yl)methyl)azetidin-3-ol; Compound 174

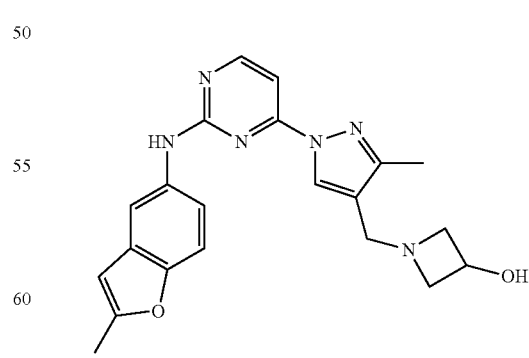

MS (ESI) m/z 391 [M+H]+; 1H NMR (300 MHz, CDCl3) δ 8.41 (d, 1H, J=5.7 Hz), 8.30 (s, 1H), 7.76 (s, 1H), 7.38~7.45 (m, 2H), 7.20 (d, 1H, J=5.7 Hz), 7.17 (s, 1H), 6.39 (s, 1H), 4.40~4.48 (m, 1H), 3.68~3.72 (m, 2H), 3.50 (s, 2H), 2.93~2.98 (m, 2H), 2.48 (s, 3H), 2.33 (s, 3H).

1-((1-(5-Fluoro-2-(1-methyl-1H-indol-5-ylamino)pyrimidin-4-yl)-3-methyl-1H-pyrazol-4-yl)methyl)azetidin-3-ol; Compound 175

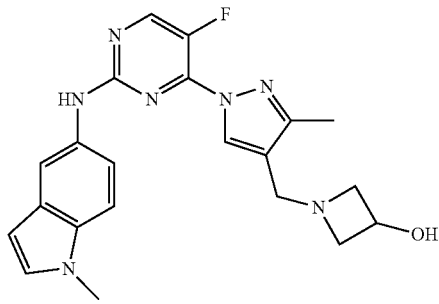 [SMILES: Cc1nn(-c2nc(Nc3ccc4c(ccn4C)c3)ncc2F)cc1CN1CC(O)C1]

MS (ESI) m/z 407 [M+H]$^+$; $^1$H NMR (300 MHz, DMSO-d$_6$) δ 9.55 (s, 1H), 8.56~8.54 (d, 1H, J=5.4 Hz), 7.91 (s, 1H), 7.67 (s, 1H), 7.46~7.38 (m, 2H), 7.29 (d, 1H, J=5.4 Hz,), 6.39 (d, 1H, J=3.0 Hz), 5.90 (s, 1H), 4.39~4.38 (m, 1H), 3.92 (s, 4H), 3.78 (s, 3H), 2.09 (s, 3H).

1-((1-(2-(3-Chloro-1,2-dimethyl-1H-indol-5-ylamino)-5-fluoropyrimidin-4-yl)-3-methyl-1H-pyrazol-4-yl)methyl)azetidin-3-ol; Compound 176

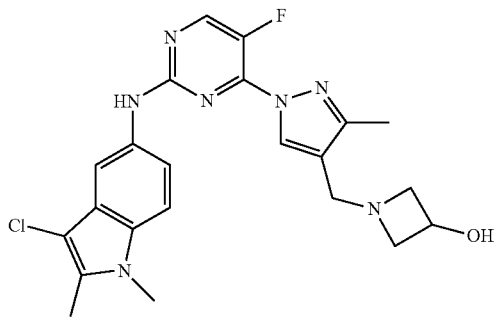 [SMILES: Cc1nn(-c2nc(Nc3ccc4c(c3)c(Cl)c(C)n4C)ncc2F)cc1CN1CC(O)C1]

MS (ESI) m/z 455 [M+H]$^+$; $^1$H NMR (300 MHz, DMSO-d$_6$) δ 9.76 (s, 1H), 8.64 (d, 1H, J=5.4 Hz), 8.05 (s, 1H), 7.83 (s, 1H), 7.57 (s, 1H), 7.45 (d, 1H, J=5.4 Hz), 7.34~7.30 (m, 1H), 6.23 (s, 1H), 4.46~4.42 (m, 1H), 4.27~4.16 (m, 4H), 4.03~3.79 (m, 2H), 3.69 (s, 3H), 2.40 (s, 3H), 2.15 (s, 3H).

1-((3-Cyclopropyl-1-(2-(2,3-dihydro-1H-inden-5-ylamino)pyrimidin-4-yl)-1H-pyrazol-4-yl)methyl)azetidin-3-ol; Compound 177

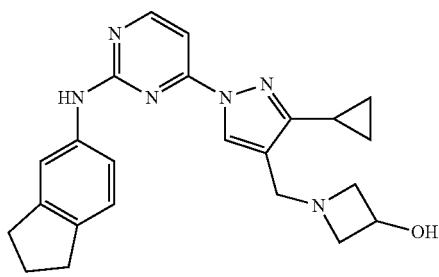 [SMILES: OC1CN(Cc2cn(-c3ccnc(Nc4ccc5c(c4)CCC5)n3)nc2C2CC2)C1]

MS (ESI) m/z 403 [M+H]$^+$; $^1$H NMR (300 MHz, DMSO-d$_6$) δ 9.61 (s, 1H), 8.45 (d, 1H, J=5.4 Hz), 8.24 (s, 1H), 7.67 (s, 1H), 7.45~7.42 (m, 1H), 7.17 (d, 1H, J=8.1 Hz,), 7.05 (d, 1H, J=5.4 Hz), 5.33 (d, 1H, J=6.3 Hz, 1H), 4.23~4.17 (m, 1H), 3.54~3.50 (m, 4H), 2.89~2.76 (m, 3H), 0.97~0.85 (m, 4H).

1-((3-Cyclopropyl-1-(2-(1-methylindolin-5-ylamino)pyrimidin-4-yl)-1H-pyrazol-4-yl)methyl)azetidin-3-ol; Compound 178

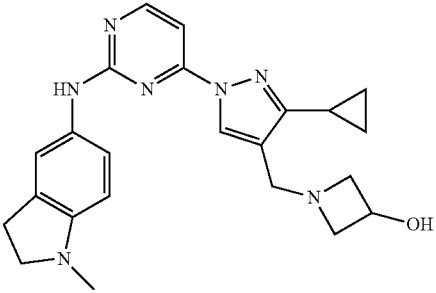 [SMILES: CN1CCc2cc(Nc3nccc(-n4cc(CN5CC(O)C5)c(C5CC5)n4)n3)ccc21]

MS (ESI) m/z 418 [M+H]$^+$; $^1$H NMR (300 MHz, DMSO-d$_6$) δ 10.1 (s, 1H), 8.44 (d, 1H, J=5.4 Hz), 8.25 (s, 1H), 7.64 (s, 2H), 7.50~7.48 (m, 1H), 7.05 (d, 1H, J=5.4 Hz), 5.33 (d, 1H, J=6.5 Hz), 4.24~4.14 (m, 1H), 3.97 (t, 2H, J=8.4 Hz), 3.74 (s, 3H), 3.53~3.49 (m, 4H), 3.12 (t, 2H, J=8.6 Hz), 2.81~2.76 (m, 2H), 2.00~1.91 (m, 1H), 0.99~0.85 (m, 4H).

1-((3-Methyl-1-(2-(1-methyl-1H-indazol-5-ylamino)pyrimidin-4-yl)-1H-pyrazol-4-yl)methyl)azetidin-3-yl pivalate; Compound 179

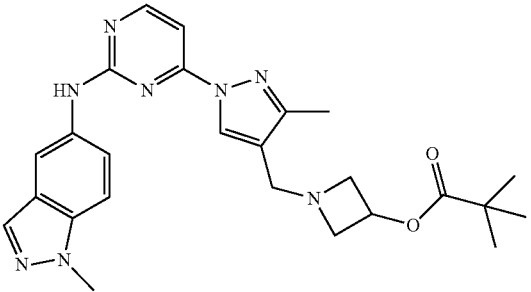 [SMILES: Cc1nn(-c2ccnc(Nc3ccc4c(cnn4C)c3)n2)cc1CN1CC(OC(=O)C(C)(C)C)C1]

To a solution of 1-((3-methyl-1-(2-(1-methyl-1H-indazol-5-ylamino)pyrimidin-4-yl)-1H-pyrazol-4-yl)methyl)azetidin-3-ol, Compound 160 (0.30 g, 0.77 mmol) in anhydrous DMF, were added N,N-dimethylaminopyridine (28 mg) and pivalic anhydride (0.62 mL, 4 equiv.). The reaction mixture was heated at 70° C. for 6 hours. Volatiles were removed in vacuo and then the resulting residue was extracted with dichloromethane. The collected organic layer was dried over anhydrous sodium sulfate and then partially concentrated in vacuo. To the resulting residue, was added heptane to form a solid. The solids were collected by filtration to give 0.30 g (83%) of the desired product as a pale yellow solid. MS (ESI) m/z 475 [M+H]$^+$; $^1$H NMR (300 MHz, CDCl$_3$) δ 8.40 (d, 1H, J=5.4 Hz), 8.29 (s, 1H), 8.02 (s, 1H), 7.97 (s, 1H), 7.50 (d, 1H, J=9.0 Hz), 7.40 (d, 1H, J=9.0 Hz), 7.22 (d, 1H, J=5.4 Hz), 5.04~5.07 (m, 1H), 4.10 (s, 3H), 3.76 (t, 2H, J=7.5 Hz), 3.54 (s, 2H), 3.02 (t, 2H, J=7.4 Hz), 2.33 (s, 3H), 1.21 (s, 9H).

1-((3-Methyl-1-(2-(1-methyl-3-(thiazol-2-yl)-1H-indol-5-ylamino)pyrimidin-4-yl)-1-pyrazol-4-yl)methyl)azetidin-3-ol; Compound 180

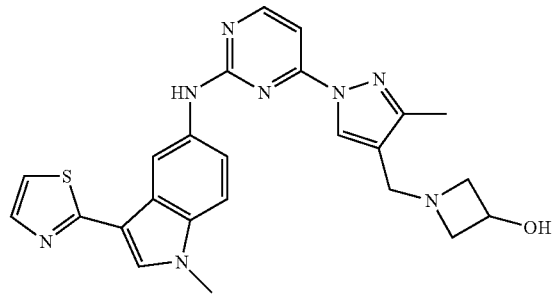 [SMILES: Cc1nn(-c2ccnc(Nc3ccc4c(c3)c(-c3nccs3)cn4C)n2)cc1CN1CC(O)C1]

MS (ESI) m/z 473 [M+H]$^+$; $^1$H NMR (300 MHz, DMSO-d$_6$) δ 8.50 (s, 1H), 8.42 (s, 1H), 8.38 (d, 1H, J=5.4 Hz), 7.76~7.73 (m, 2H), 7.44 (dd, 1H, J=1.8, 8.7 Hz), 7.37 (d, 1H, J=8.7 Hz), 7.17~7.23 (m, 1H), 4.31~4.35 (m, 1H), 3.87 (s, 3H), 3.56~3.61 (m, 2H), 3.51 (s, 2H), 2.94~2.99 (m, 2H), 2.31 (s, 3H).

1-((1-(2-(3-Chloro-1-methyl-1H-indol-5-ylamino)pyrimidin-4-yl)-3-methyl-1H-pyrazol-4-yl)methyl)azetidin-3-ol methanesulfonate; Compound 181

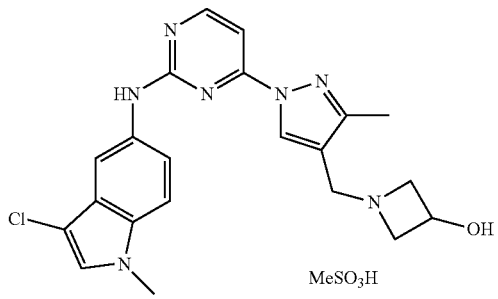 [SMILES: "MeSO3H" ; Cc1nn(-c2ccnc(Nc3ccc4c(c3)c(Cl)cn4C)n2)cc1CN1CC(O)C1]

MeSO$_3$H

To a slurry of 1-((1-(2-(3-chloro-1-methyl-1H-indol-5-ylamino)pyrimidin-4-yl)-3-methyl-1H-pyrazol-4-yl)methyl)azetidin-3-ol, Compound No. 144 (127 mg, 0.3 mmol) in methanol, was added 1 equivalant of methanesulfonic acid at room temperature. After being stirred at room temperature, the resulting solids were collected by filtration, rinsed with cold methanol and then vacuum dried to give 85 mg (54%) of the desired compound 181 as a pale yellow solid. MS (ESI) m/z 424 [M+H]$^+$; $^1$H NMR (300 MHz, DMSO-d$_6$) δ 9.9 (br s, 1H), 9.98 (s, 1H), 8.66 (s, 1H), 8.53 (d, 1H, J=5.4 Hz), 7.92 (S, 1H), 7.53~7.51 (m, 3H), 7.19 (d, 1H, J=5.4 Hz), 4.45~4.50 (m, 1H), 4.32~4.38 (m, 2H), 4.22~4.28 (m, 2H), 3.85~3.91 (m, 2H), 3.79 (s, 3H), 2.36 (s, 3H).

1-((1-(2-(3-Chloro-1-methyl-1H-indazol-5-ylamino)-5-fluoropyrimidin-4-yl)-4-methyl-1H-pyrrol-3-yl)methyl)azetidin-3-ol; Compound 182

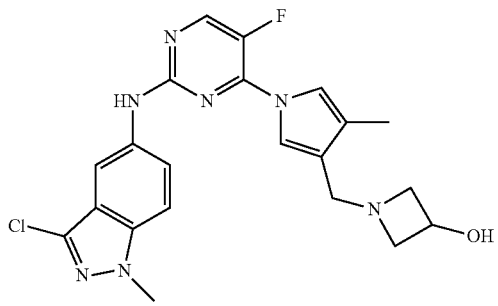 [SMILES: Cc1cn(-c2nc(Nc3ccc4c(c3)c(Cl)nn4C)ncc2F)cc1CN1CC(O)C1]

MS (ESI) m/z 442 [M+H]$^+$.

1-((1-(2-(3-Chloro-1-isopropyl-1H-indazol-5-ylamino)-5-fluoropyrimidin-4-yl)-4-methyl-1H-pyrrol-3-yl)methyl)azetidin-3-ol; Compound 183

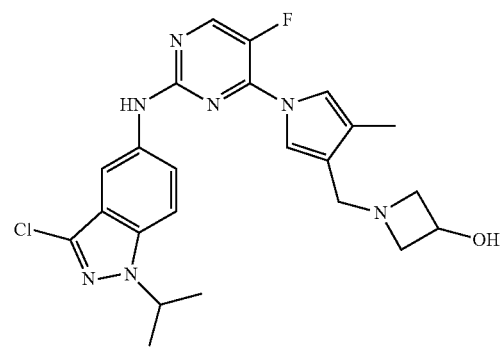 [SMILES: Cc1cn(-c2nc(Nc3ccc4c(c3)c(Cl)nn4C(C)C)ncc2F)cc1CN1CC(O)C1]

MS (ESI) m/z 470 [M+H]$^+$.

1-((1-(2-(3-Chloro-2-isopropyl-2H-indazol-5-ylamino)-5-fluoropyrimidin-4-yl)-4-methyl-1H-pyrrol-3-yl)methyl)azetidin-3-ol; Compound 184

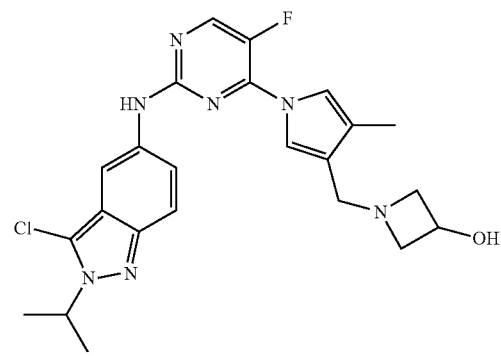 [SMILES: Cc1cn(-c2nc(Nc3ccc4nn(C(C)C)c(Cl)c4c3)ncc2F)cc1CN1CC(O)C1]

MS (ESI) m/z 470 [M+H]$^+$.

1-((1-(2-(3-Chloro-1,2-dimethyl-1H-indol-5-ylamino)-5-methylpyrimidin-4-yl)-4-methyl-1H-pyrrol-3-yl)methyl)azetidin-3-ol; Compound 185

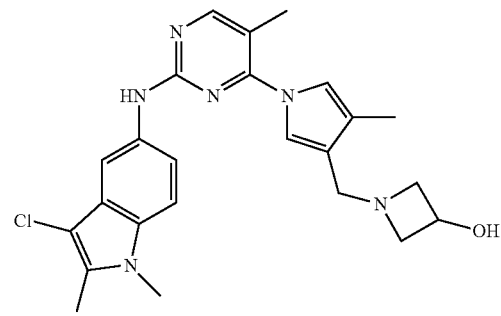 [SMILES: Cc1cn(-c2nc(Nc3ccc4c(c3)c(Cl)c(C)n4C)ncc2C)cc1CN1CC(O)C1]

MS (ESI) m/z 451 [M+H]$^+$.

95

(R)-1-((1-(2-(3-Chloro-1-methyl-1H-indol-5-ylamino)pyrimidin-4-yl)-3-methyl-1H-pyrazol-4-yl)methyl)pyrrolidin-3-ol; Compound 186

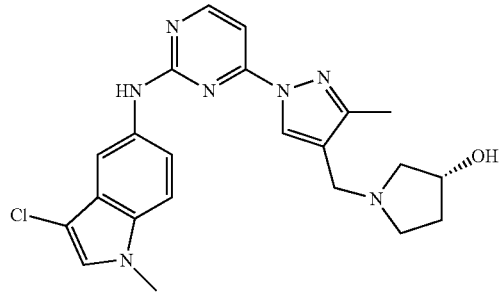 [SMILES: Cc1nn(-c2ccnc(Nc3ccc4c(c3)c(Cl)cn4C)n2)cc1CN1CC[C@@H](O)C1]

MS (ESI) m/z 438 [M+H]+.

(R)-1-((1-(2-(3-Chloro-1-cyclopropyl-1H-indol-5-ylamino)pyrimidin-4-yl)-3-methyl-1H-pyrazol-4-yl)methyl)pyrrolidin-3-ol; Compound 187

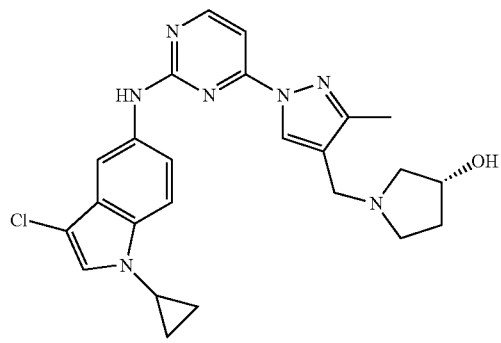 [SMILES: Cc1nn(-c2ccnc(Nc3ccc4c(c3)c(Cl)cn4C3CC3)n2)cc1CN1CC[C@@H](O)C1]

MS (ESI) m/z 464 [M+H]+.

(R)-1-((1-(2-(3-Bromo-1,2-dimethyl-1H-indol-5-ylamino)pyrimidin-4-yl)-3-methyl-1H-pyrazol-4-yl)methyl)pyrrolidin-3-ol; Compound 188

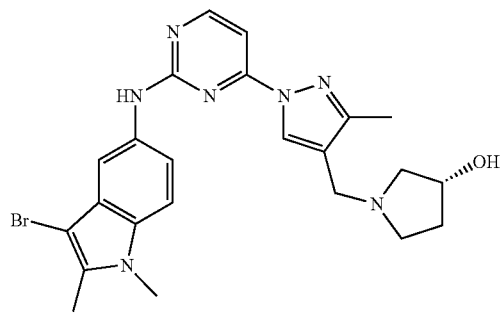 [SMILES: Cc1nn(-c2ccnc(Nc3ccc4c(c3)c(Cl)c(C)n4C)n2)cc1CN1CC[C@@H](O)C1]

MS (ESI) m/z 496 [M+H]+, 498 [M+2+H]+.

96

(R)-1-((1-(2-(3-Chloro-1,2-dimethyl-1H-indol-5-ylamino)pyrimidin-4-yl)-3-methyl-1H-pyrazol-4-yl)methyl)pyrrolidin-3-ol; Compound 189

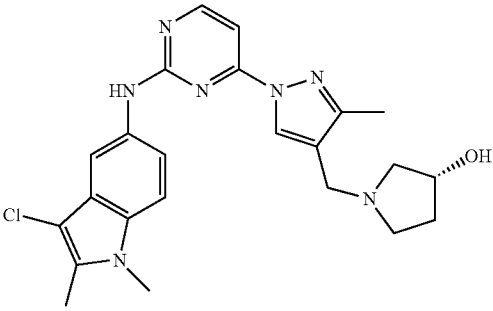

MS (ESI) m/z 452 [M+H]+.

(R)-Cyclopropyl(5-(4-(4-((3-hydroxypyrrolidin-1-yl)methyl)-3-methyl-1H-pyrazol-1-yl)pyrimidin-2-ylamino)-1-methyl-1H-indol-3-yl)methanone; Compound 190

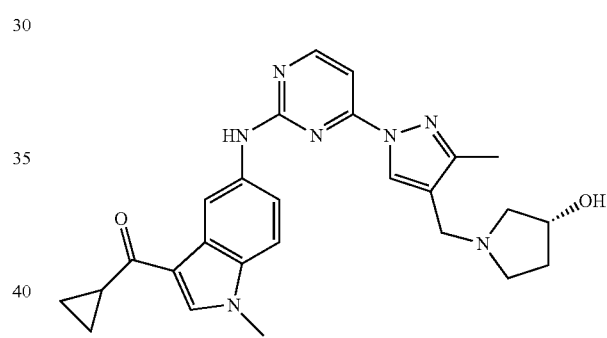

MS (ESI) m/z 472 [M+H]+.

(R)-Cyclopropyl(5-(4-(4-((3-hydroxypiperidin-1-yl)methyl)-3-methyl-1H-pyrazol-1-yl)pyrimidin-2-ylamino)-1-methyl-1H-indol-3-yl)methanone; Compound 191

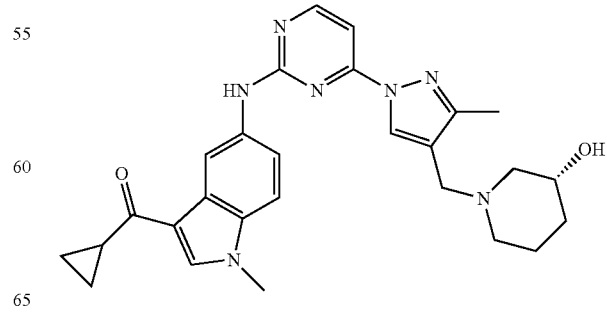

MS (ESI) m/z 486 [M+H]+.

97

(R)-1-((1-(2-(3-Chloro-1,2-dimethyl-1H-indol-5-ylamino)pyrimidin-4-yl)-3-methyl-1H-pyrazol-4-yl)methyl)piperidin-3-ol; Compound 192

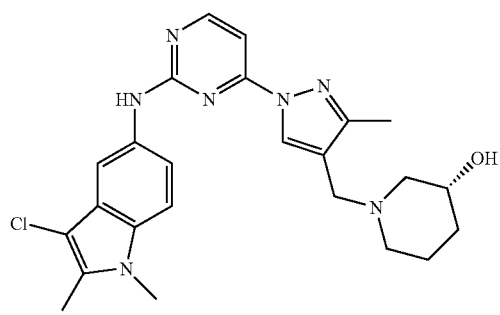 [SMILES: Cc1nn(-c2ccnc(Nc3ccc4c(c3)c(Cl)c(C)n4C)n2)cc1CN1CCC[C@@H](O)C1]

MS (ESI) m/z 465 [M+H]⁺.

(R)-1-((1-(2-(3-Chloro-1-methyl-1H-indol-5-ylamino)pyrimidin-4-yl)-3-methyl-1H-pyrazol-4-yl)methyl)piperidin-3-ol; Compound 193

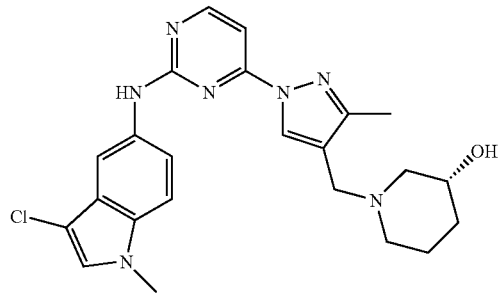 [SMILES: Cc1nn(-c2ccnc(Nc3ccc4c(c3)c(Cl)cn4C)n2)cc1CN1CCC[C@@H](O)C1]

MS (ESI) m/z 452 [M+H]⁺.

(S)-1-((1-(2-(3-Chloro-1,2-dimethyl-1H-indol-5-ylamino)pyrimidin-4-yl)-3-methyl-1H-pyrazol-4-yl)methyl)pyrrolidin-3-ol; Compound 194

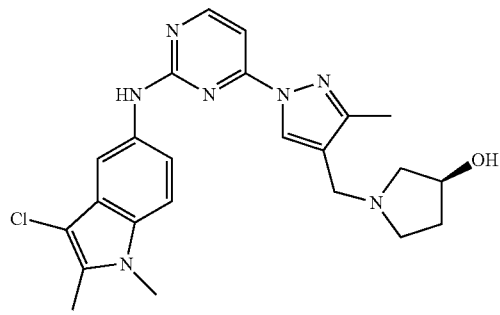 [SMILES: Cc1nn(-c2ccnc(Nc3ccc4c(c3)c(Cl)c(C)n4C)n2)cc1CN1CC[C@H](O)C1]

MS (ESI) m/z 452 [M+H]⁺.

98

(S)-1-((1-(2-(3-Chloro-1-cyclopropyl-1H-indol-5-ylamino)pyrimidin-4-yl)-3-methyl-1H-pyrazol-4-yl)methyl)pyrrolidin-3-ol; Compound 195

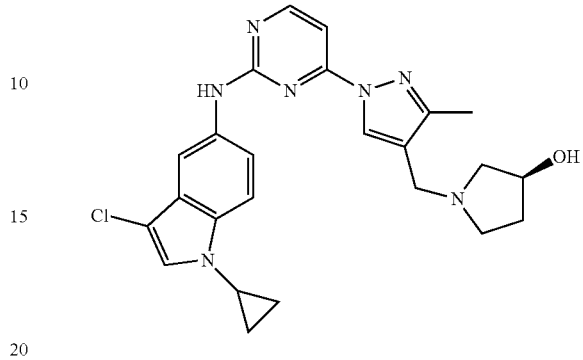

MS (ESI) m/z 464 [M+H]⁺.

(1-(2-(1-Cyclopropyl-3-methyl-1H-indol-5-ylamino)pyrimidin-4-yl)-3-methyl-1H-pyrazol-4-yl)(3-hydroxyazetidin-1-yl)methanone; Compound 196

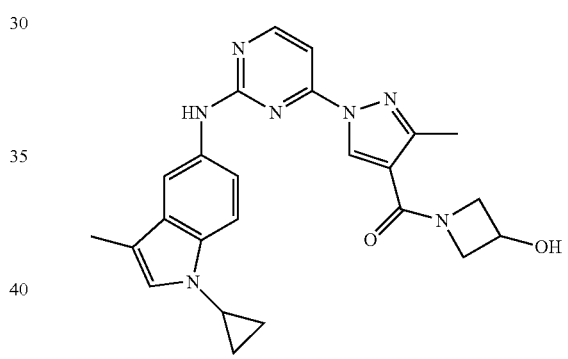

MS (ESI) m/z 444 [M+H]⁺.

3-Chloro-1,2-dimethyl-N-(6-(3-methyl-4-(piperazin-1-ylmethyl)-1H-pyrrol-1-yl)pyridin-2-yl)-1H-indol-5-amine; Compound 197

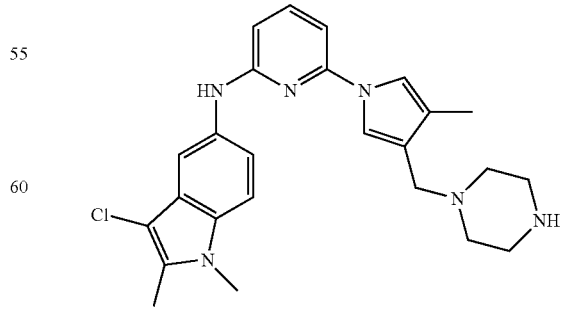

MS (ESI) m/z 489 [M+H]⁺.

(R)-2,2,2-trifluoro-1-(5-(6-(3-((3-hydroxypyrrolidin-1-yl)methyl)-4-methyl-1H-pyrrol-1-yl)pyridin-2-ylamino)-1-methyl-1H-indol-3-yl)ethanone; Compound 198

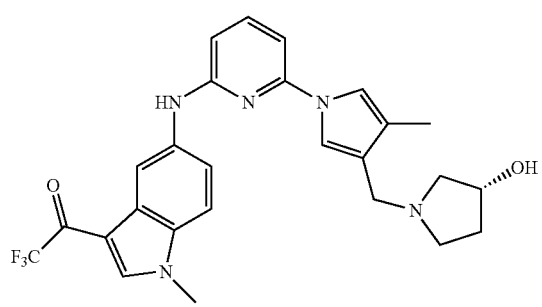 [SMILES: Cc1cn(-c2cccc(Nc3ccc4c(c3)c(C(=O)C(F)(F)F)cn4C)n2)cc1CN1CC[C@@H](O)C1]

MS (ESI) m/z 498 [M+H]⁺.

1-(5-(4-(4-(((3R,4S)-3,4-Dihydroxypyrrolidin-1-yl)methyl)-3-methyl-1H-pyrazol-1-yl)pyrimidin-2-ylamino)-1H-indol-3-yl)ethanone; Compound 199

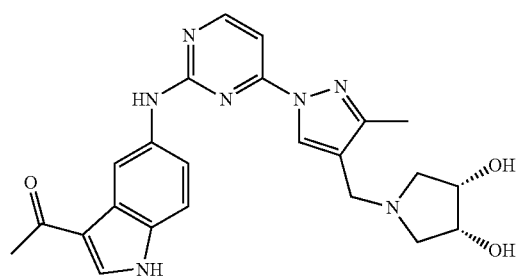 [SMILES: CC(=O)c1c[nH]c2ccc(Nc3nccc(-n4cc(CN5C[C@@H](O)[C@@H](O)C5)c(C)n4)n3)cc12]

MS (ESI) m/z 478 [M+H]⁺

(R)-1-(5-(4-(4-((3-Hydroxypyrrolidin-1-yl)methyl)-3-methyl-1H-pyrazol-1-yl)pyrimidin-2-ylamino)-1H-indol-3-yl)ethanone; Compound 200

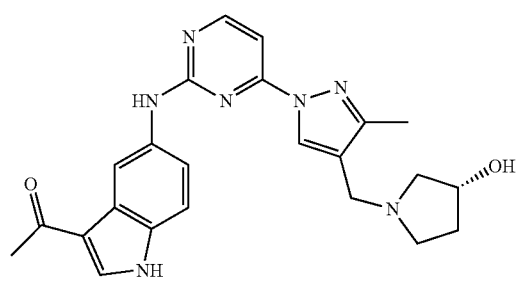 [SMILES: CC(=O)c1c[nH]c2ccc(Nc3nccc(-n4cc(CN5CC[C@@H](O)C5)c(C)n4)n3)cc12]

MS (ESI) m/z 432 [M+H]⁺

1-(5-(4-(4-((3-Hydroxyazetidin-1-yl)methyl)-3-methyl-1H-pyrazol-1-yl)pyrimidin-2-ylamino)-1H-indol-3-yl)ethanone; Compound 201

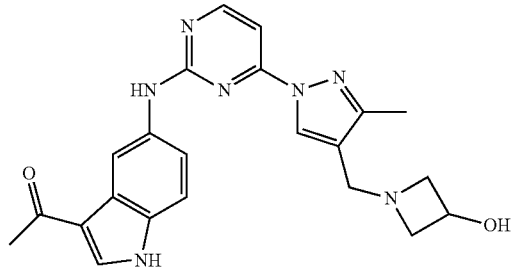 [SMILES: CC(=O)c1c[nH]c2ccc(Nc3nccc(-n4cc(CN5CC(O)C5)c(C)n4)n3)cc12]

MS (ESI) m/z 418 [M+H]⁺

1-(5-(4-(4-(((3R,4S)-3,4-Dihydroxypyrrolidin-1-yl)methyl)-3-methyl-1H-pyrazol-1-yl)pyrimidin-2-ylamino)-1H-indol-3-yl)-2,2,2-trifluoroethanone; Compound 202

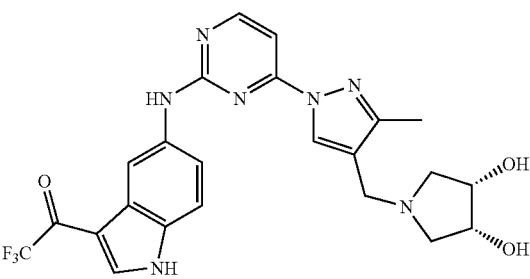 [SMILES: Cc1nn(-c2ccnc(Nc3ccc4[nH]cc(C(=O)C(F)(F)F)c4c3)n2)cc1CN1C[C@@H](O)[C@@H](O)C1]

MS (ESI) m/z 502 [M+H]⁺

(R)-2,2,2-Trifluoro-1-(5-(4-(4-((3-hydroxypyrrolidin-1-yl)methyl)-3-methyl-1H-pyrazol-1-yl)pyrimidin-2-ylamino)-1H-indol-3-yl)ethanone; Compound 203

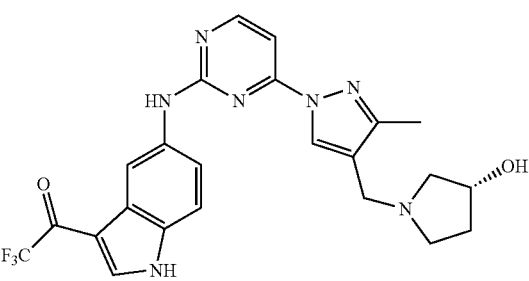 [SMILES: Cc1nn(-c2ccnc(Nc3ccc4[nH]cc(C(=O)C(F)(F)F)c4c3)n2)cc1CN1CC[C@@H](O)C1]

MS (ESI) m/z 486 [M+H]⁺

101

2,2,2-Trifluoro-1-(5-(4-(4-(((2S,4R)-4-hydroxy-2-(hydroxymethyl)pyrrolidin-1-yl)methyl)-3-methyl-1H-pyrazol-1-yl)pyrimidin-2-ylamino)-1H-indol-3-yl)ethanone; Compound 204

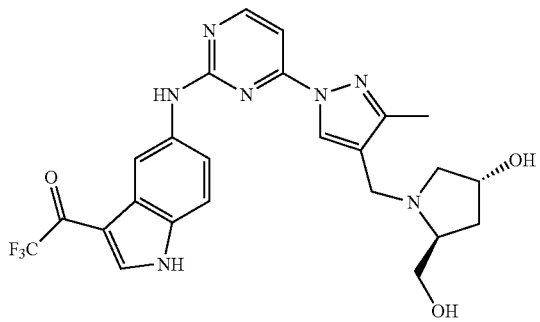 [SMILES: Cc1nn(-c2ccnc(Nc3ccc4[nH]cc(C(=O)C(F)(F)F)c4c3)n2)cc1CN1C[C@H](O)C[C@H]1CO]

MS (ESI) m/z 516 [M+H]+

1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2,2,2-trifluoroethanone; Compound 205

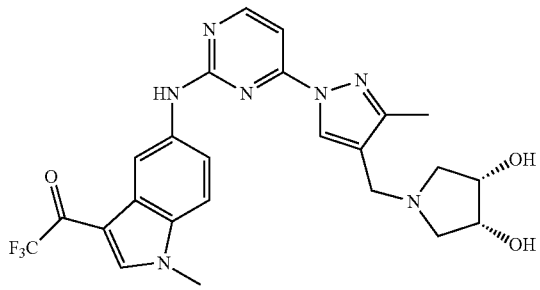 [SMILES: Cc1nn(-c2ccnc(Nc3ccc4c(c3)c(C(=O)C(F)(F)F)cn4C)n2)cc1CN1C[C@@H](O)[C@@H](O)C1]

MS (ESI) m/z 516 [M+H]+

2,2,2-Trifluoro-1-(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)ethanone; Compound 206

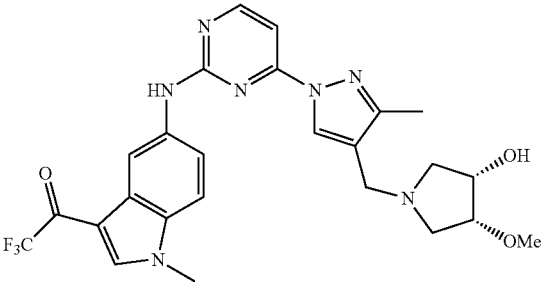 [SMILES: CO[C@@H]1CN(Cc2cn(-c3ccnc(Nc4ccc5c(c4)c(C(=O)C(F)(F)F)cn5C)n3)nc2C)C[C@@H]1O]

MS (ESI) m/z 530 [M+H]+

102

2,2,2-Trifluoro-1-(5-(4-(4-(2S,4R)-4-hydroxy-2-(hydroxymethyl)pyrrolidin-1-yl)methyl)-3-methyl-1H-pyrazol-1-yl)pyrimidin-2-ylamino)-1-methyl-1H-indol-3-yl)ethanone; Compound 207

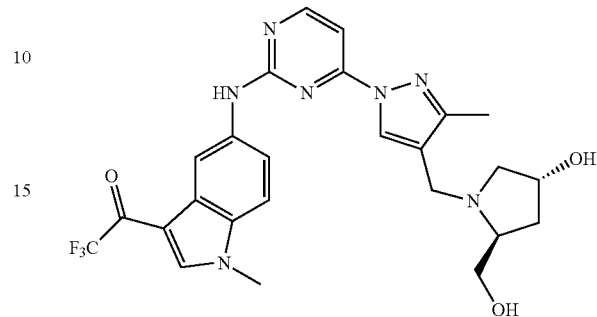

MS (ESI) m/z 530[M+H]+

Cyclopropyl(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)methanone; Compound 208

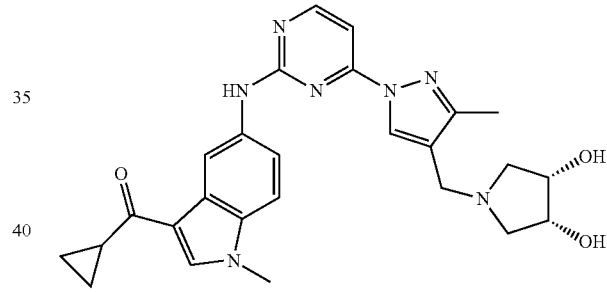

MS (ESI) m/z 488 [M+H]+

Cyclopropyl(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)methanone; Compound 209

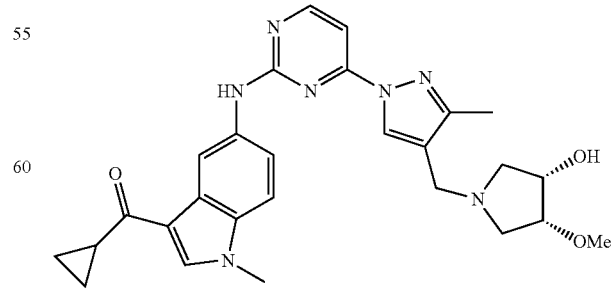

MS (ESI) m/z 502 [M+H]+

103

Cyclopropyl(5-(4-(4-(((3S,4S)-3,4-dihydroxypyrrolidin-1-yl)methyl)-3-methyl-1H-pyrazol-1-yl)pyrimidin-2-ylamino)-1-methyl-1H-indol-3-yl)methanone; Compound 210

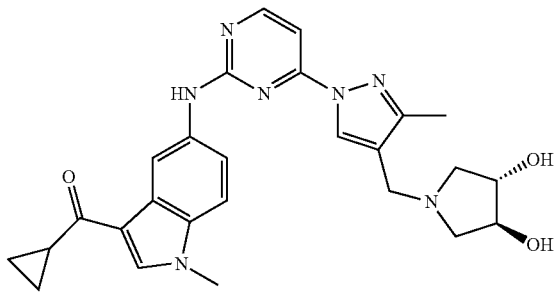 [SMILES: Cc1nn(-c2ccnc(Nc3ccc4c(c3)c(C(=O)C3CC3)cn4C)n2)cc1CN1C[C@H](O)[C@@H](O)C1]

MS (ESI) m/z 488 [M+H]$^+$ (3R,4S)-1-((1-(2-(3-(Cyclopropanecarbonyl)-1-methyl-1H-indol-5-ylamino)pyrimidin-4-yl)-3-methyl-1H-pyrazol-4-yl)methyl)pyrrolidine-3,4-diyl diacetate: Compound 211

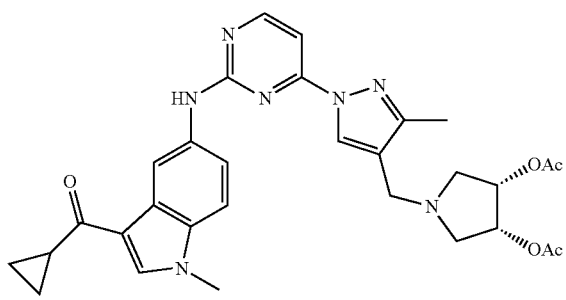 [SMILES: CC(=O)O[C@H]1CN(Cc2cn(-c3ccnc(Nc4ccc5c(c4)c(C(=O)C4CC4)cn5C)n3)nc2C)C[C@H]1OC(C)=O]

MS (ESI) m/z 572 [M+H]$^+$

Cyclopropyl(5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)methanone; Compound 212

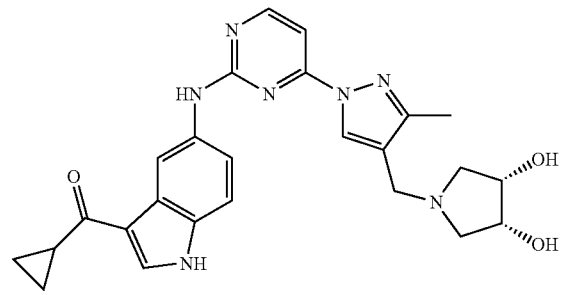 [SMILES: Cc1nn(-c2ccnc(Nc3ccc4[nH]cc(C(=O)C5CC5)c4c3)n2)cc1CN1C[C@@H](O)[C@@H](O)C1]

MS (ESI) m/z 474[M+H]$^+$

104

Cyclopropyl(5-(4-(4-(((3S,4R)-3-hydroxy-4-methoxypyrrolidin-1-yl)methyl)-3-methyl-1H-pyrazol-1-yl)pyrimidin-2-ylamino)-1H-indol-3-yl)methanone; Compound 213

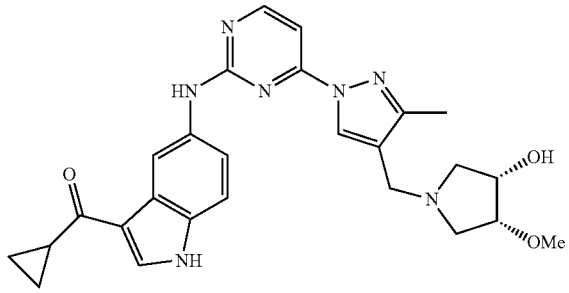 [SMILES: CO[C@@H]1CN(Cc2cn(-c3ccnc(Nc4ccc5[nH]cc(C(=O)C6CC6)c5c4)n3)nc2C)C[C@@H]1O]

MS (ESI) m/z 488 [M+H]$^+$

Cyclopropyl(5-(4-(4-(((3S,4S)-3,4-dihydroxypyrrolidin-1-yl)methyl)-3-methyl-1H-pyrazol-1-yl)pyrimidin-2-ylamino)-1H-indol-3-yl)methanone; Compound 214

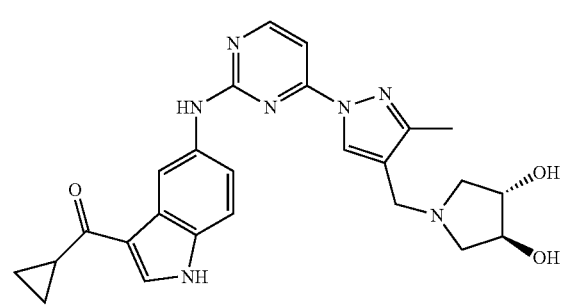 [SMILES: Cc1nn(-c2ccnc(Nc3ccc4[nH]cc(C(=O)C5CC5)c4c3)n2)cc1CN1C[C@H](O)[C@@H](O)C1]

MS (ESI) m/z 474[M+H]$^+$ (R)-Cyclopropyl(5-(4-(4-((3-hydroxypyrrolidin-1-yl)methyl)-3-methyl-1H-pyrazol-1-yl)pyrimidin-2-ylamino)-1H-indol-3-yl)methanone; Compound 215

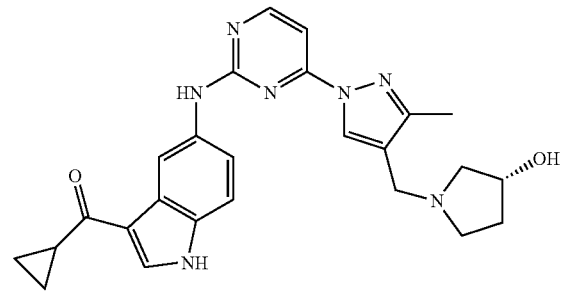 [SMILES: Cc1nn(-c2ccnc(Nc3ccc4[nH]cc(C(=O)C5CC5)c4c3)n2)cc1CN1CC[C@@H](O)C1]

MS (ESI) m/z 458 [M+H]$^+$

| 105 | 106 |
|---|---|
| 1-(5-(4-(4-(((3R,4S)-3,4-Dihydroxypyrrolidin-1-yl)methyl)-3-methyl-1H-pyrazol-1-yl)pyrimidin-2-ylamino)-1H-indol-3-yl)-2,2-difluoroethanone; Compound 216 | 2,2-Difluoro-1-(5-(4-(4-(((3S,4R)-3-hydroxy-4-methoxypyrrolidin-1-yl)methyl)-3-methyl-1H-pyrazol-1-yl)pyrimidin-2-ylamino)-1H-indol-3-yl)ethanone; Compound 219 |

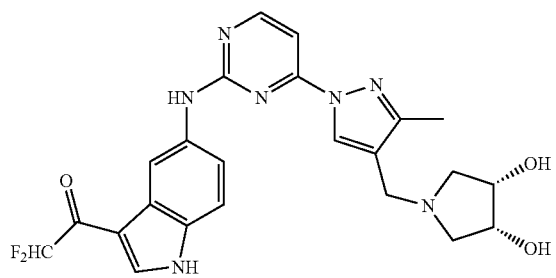 [SMILES: Cc1nn(-c2ccnc(Nc3ccc4[nH]cc(C(=O)C(F)F)c4c3)n2)cc1CN1C[C@@H](O)[C@@H](O)C1]

MS (ESI) m/z 484 [M+H]⁺     MS (ESI) m/z 498 [M+H]⁺

| | |
|---|---|
| (R)-2,2-Difluoro-1-(5-(4-(4-((3-hydroxypyrrolidin-1-yl)methyl)-3-methyl-1H-pyrazol-1-yl)pyrimidin-2-ylamino)-1H-indol-3-yl)ethanone; Compound 217 | 1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-difluoroethanone; Compound 220 |

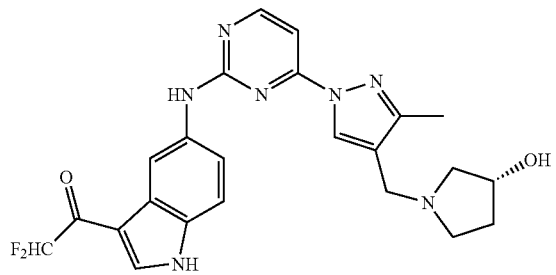 [SMILES: Cc1nn(-c2ccnc(Nc3ccc4[nH]cc(C(=O)C(F)F)c4c3)n2)cc1CN1CC[C@@H](O)C1]

MS (ESI) m/z 468 [M+H]⁺     MS (ESI) m/z 498 [M+H]⁺

| | |
|---|---|
| 1-(5-(4-(4-(((3S,4S)-3,4-Dihydroxypyrrolidin-1-yl)methyl)-3-methyl-1H-pyrazol-1-yl)pyrimidin-2-ylamino)-1H-indol-3-yl)-2,2-difluoroethanone; Compound 218 | 2,2-Difluoro-1-(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)ethanone; Compound 221 |

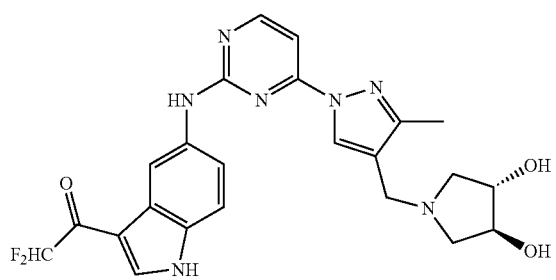 [SMILES: Cc1nn(-c2ccnc(Nc3ccc4[nH]cc(C(=O)C(F)F)c4c3)n2)cc1CN1C[C@H](O)[C@@H](O)C1]

MS (ESI) m/z 484 [M+H]⁺     MS (ESI) m/z 512 [M+H]⁺

107

1-(5-(4-(4-(((3S,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-difluoroethanone; Compound 222

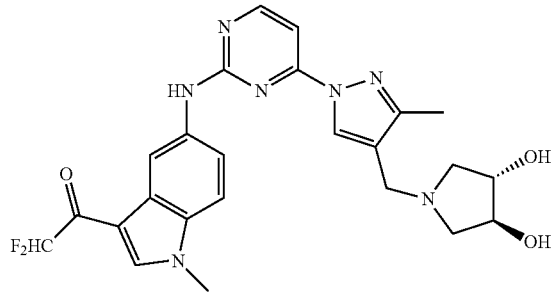 [SMILES: Cc1nn(-c2ccnc(Nc3ccc4c(c3)c(C(=O)C(F)F)cn4C)n2)cc1CN1C[C@H](O)[C@@H](O)C1]

MS (ESI) m/z 498 [M+H]+

(R)-2,2-Difluoro-1-(5-(4-(4-((3-hydroxypyrrolidin-1-yl)methyl)-3-methyl-1H-pyrazol-1-yl)pyrimidin-2-ylamino)-1-methyl-1H-indol-3-yl)ethanone; Compound 223

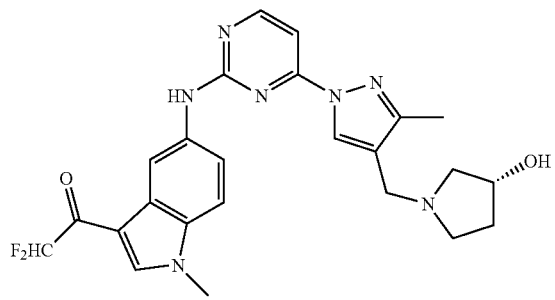 [SMILES: Cc1nn(-c2ccnc(Nc3ccc4c(c3)c(C(=O)C(F)F)cn4C)n2)cc1CN1CC[C@@H](O)C1]

MS (ESI) m/z 482 [M+H]+

1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one; Compound 224

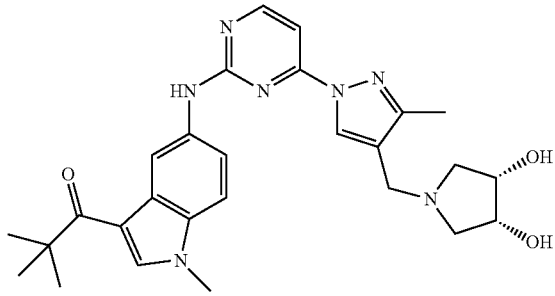 [SMILES: Cc1nn(-c2ccnc(Nc3ccc4c(c3)c(C(=O)C(C)(C)C)cn4C)n2)cc1CN1C[C@@H](O)[C@@H](O)C1]

MS (ESI) m/z 504 [M+H]+

108

1-(5-(4-(4-(((3S,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one; Compound 225

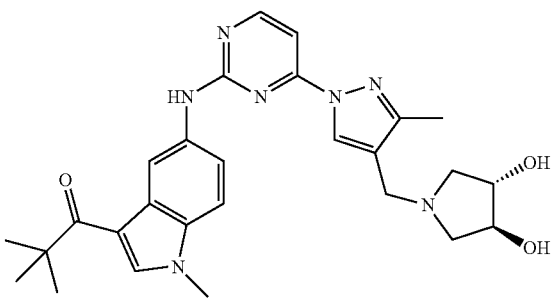 [SMILES: Cc1nn(-c2ccnc(Nc3ccc4c(c3)c(C(=O)C(C)(C)C)cn4C)n2)cc1CN1C[C@H](O)[C@@H](O)C1]

MS (ESI) m/z 504 [M+H]+

(R)-1-(5-(4-(4-(3-Hydroxypyrrolidin-1-yl)methyl)-3-methyl-1H-pyrazol-1-yl)pyrimidin-2-ylamino)-1-methyl-1H-indol-3-yl)-2,2-dimethylpropan-1-one; Compound 226

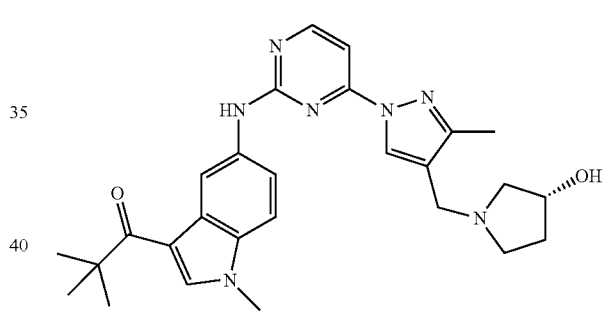

MS (ESI) m/z 488 [M+H]+

Cyclopropyl(1-cyclopropyl-5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)methanone; Compound 227

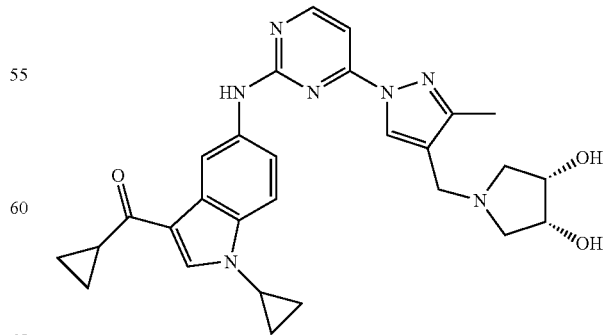

MS (ESI) m/z 513 [M+H]+

(R)-Cyclopropyl(1-cyclopropyl-5-(4-(4-((3-hydroxy-pyrrolidin-1-yl)methyl)-3-methyl-1H-pyrazol-1-yl)pyrimidin-2-ylamino)-1H-indol-3-yl)methanone;
Compound 228

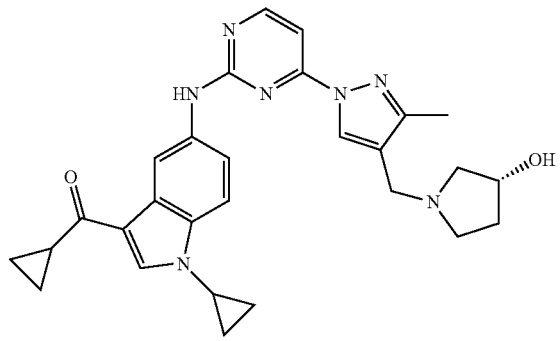 [SMILES: Cc1nn(-c2ccnc(Nc3ccc4c(c3)c(C(=O)C3CC3)cn4C3CC3)n2)cc1CN1CC[C@@H](O)C1]

MS (ESI) m/z 498 [M+H]+

(R)-Cyclopropyl(1-cyclopropyl-5-(4-(4-((3-methoxypyrrolidin-1-yl)methyl)-3-methyl-1H-pyrazol-1-yl)pyrimidin-2-ylamino)-1H-indol-3-yl)methanone;
Compound 229

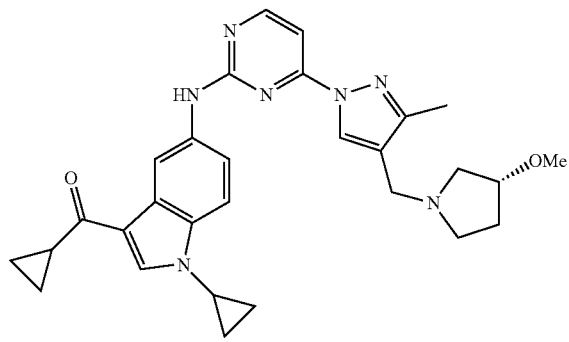 [SMILES: CO[C@@H]1CCN(Cc2cn(-c3ccnc(Nc4ccc5c(c4)c(C(=O)C4CC4)cn5C4CC4)n3)nc2C)C1]

MS (ESI) m/z 512 [M+H]+

(3S,4R)-1-((1-(2-(3-Chloro-1,2-dimethyl-1H-indol-5-ylamino)pyrimidin-4-yl)-3-methyl-1H-pyrazol-4-yl)methyl)-4-fluoropyrrolidin-3-ol; Compound 230

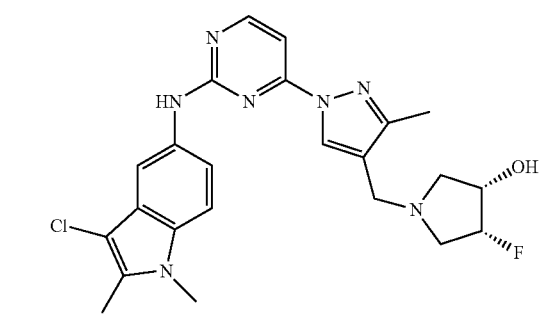 [SMILES: Cc1nn(-c2ccnc(Nc3ccc4c(c3)c(Cl)c(C)n4C)n2)cc1CN1C[C@@H](F)[C@@H](O)C1]

MS (ESI) m/z 470 [M+H]+

(2S,4R)-1-((1-(2-(3-Chloro-1,2-dimethyl-1H-indol-5-ylamino)pyrimidin-4-yl)-3-methyl-1H-pyrazol-4-yl)methyl)-4-hydroxypyrrolidine-2-carboxylic acid;
Compound 231

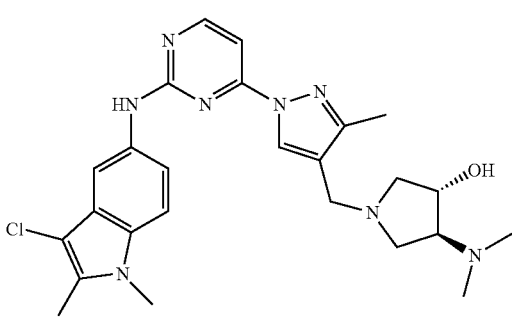 [SMILES: Cc1nn(-c2ccnc(Nc3ccc4c(c3)c(Cl)c(C)n4C)n2)cc1CN1C[C@H](O)[C@@H](N(C)C)C1]

MS (ESI) m/z 496 [M+H]+

(3S,4S)-1-((1-(2-(3-Chloro-1,2-dimethyl-1H-indol-5-ylamino)pyrimidin-4-yl)-3-methyl-1H-pyrazol-4-yl)methyl)-4-(dimethylamino)pyrrolidin-3-ol; Compound 232

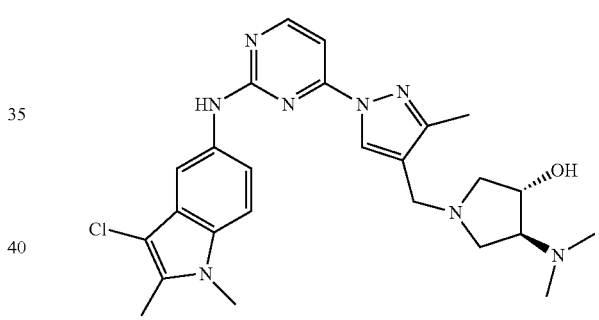

MS (ESI) m/z 496 [M+H]+

(R)-2-(((1-(2-(3-Chloro-1,2-dimethyl-1H-indol-5-ylamino)pyrimidin-4-yl)-3-methyl-1H-pyrazol-4-yl)methyl)(ethyl)amino)propan-1-ol; Compound 233

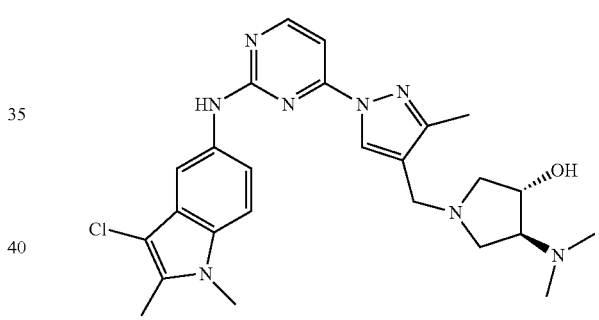

MS (ESI) m/z 468 [M+H]+

111

3-Chloro-N-(4-(4-((3-methoxyazetidin-1-yl)methyl)-3-methyl-1H-pyrazol-1-yl)pyrimidin-2-yl)-1,2-dimethyl-1H-indol-5-amine; Compound 234

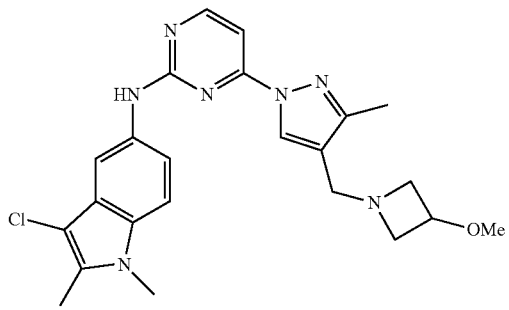 [SMILES: COC1CN(Cc2cn(-c3ccnc(Nc4ccc5c(c4)c(Cl)c(C)n5C)n3)nc2C)C1]

MS (ESI) m/z 452 [M+H]$^+$ (3R,5S)-1-((1-(2-(3-Chloro-1,2-dimethyl-1H-indol-5-ylamino)pyrimidin-4-yl)-3-methyl-1H-pyrazol-4-yl)methyl)-5-(methoxymethyl)pyrrolidin-3-ol; Compound 235

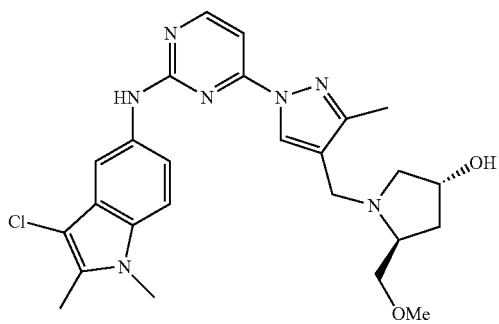 [SMILES: COC[C@@H]1C[C@@H](O)CN1Cc1cn(-c2ccnc(Nc3ccc4c(c3)c(Cl)c(C)n4C)n2)nc1C]

MS (ESI) m/z 496 [M+H]$^+$; $^1$H NMR (300 MHz, CDCl$_3$) δ 8.43 (s, 1H), 8.34 (d, J=5.4 Hz, 1H), 8.06 (br s, 1H), 7.21-7.32 (m, 4H), 4.35-4.39 (m, 1H), 3.98 (d, J=13.8 Hz, 1H), 3.72 (s, 3H), 3.50 (s, 2H), 3.40-3.47 (m, 2H), 3.38 (s, 3H), 3.29-3.34 (m, 1H), 3.05-3.12 (m, 1H), 2.44 (s, 3H), 2.36 (s, 3H), 2.40-2.43 (m, 1H), 2.31-2.39 (m, 1H), 1.89-1.94 (m, 2H).

1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2-methylpropan-1-one; Compound 236

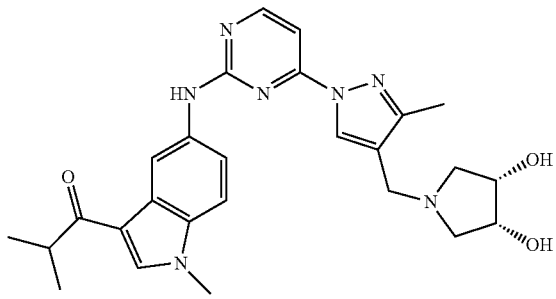 [SMILES: Cc1nn(-c2ccnc(Nc3ccc4c(c3)c(C(=O)C(C)C)cn4C)n2)cc1CN1C[C@@H](O)[C@@H](O)C1]

MS (ESI) m/z 490 [M+H]$^+$

112

1-(5-(4-(4-(((3S,4S)-3,4-dihydroxypyrrolidin-1-yl)methyl)-3-methyl-1H-pyrazol-1-yl)pyrimidin-2-ylamino)-1-methyl-1H-indol-3-yl)-2-methylpropan-1-one; Compound 237

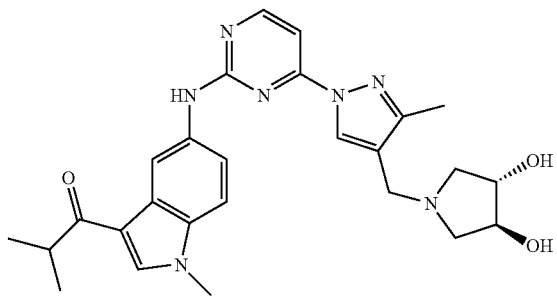 [SMILES: Cc1nn(-c2ccnc(Nc3ccc4c(c3)c(C(=O)C(C)C)cn4C)n2)cc1CN1C[C@H](O)[C@@H](O)C1]

MS (ESI) m/z 490 [M+H]$^+$ (R)-1-(5-(4-(4-(3-Hydroxypyrrolidin-1-yl)methyl)-3-methyl-1H-pyrazol-1-yl)pyrimidin-2-ylamino)-1-methyl-1H-indol-3-yl)-2-methylpropan-1-one; Compound 238

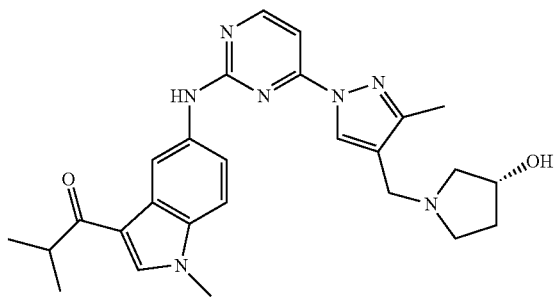 [SMILES: Cc1nn(-c2ccnc(Nc3ccc4c(c3)c(C(=O)C(C)C)cn4C)n2)cc1CN1CC[C@@H](O)C1]

MS (ESI) m/z 474 [M+H]$^+$ 1-(5-(4-(4-(((3S,4R)-3-Hydroxy-4-methoxypyrrolidin-1-yl)methyl)-3-methyl-1H-pyrazol-1-yl)pyrimidin-2-ylamino)-1-methyl-1H-indol-3-yl)-2-methylpropan-1-one; Compound 239

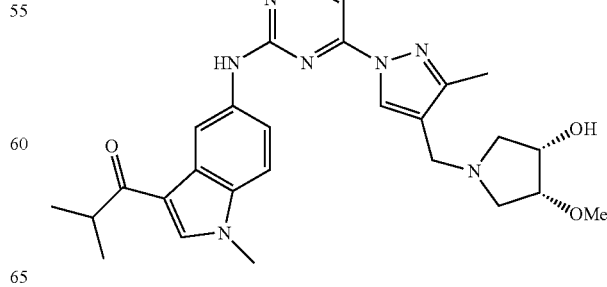

MS (ESI) m/z 504 [M+H]$^+$

113

(R)-1 (2 (1 (2 (3 Chloro-1,2-dimethyl-1H-indol-5-ylamino)pyrimidin-4-yl)-3-methyl-1H-pyrazol-4-yl)ethyl)pyrrolidin-3-ol; Compound 240

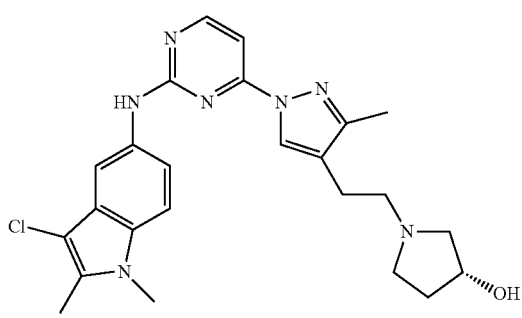 [SMILES: Cc1nn(-c2ccnc(Nc3ccc4c(c3)c(Cl)c(C)n4C)n2)cc1CCN1CC[C@@H](O)C1]

MS (ESI) m/z 466 [M+H]$^+$ 1 (2 (1 (2 (3 Chloro-1,2-dimethyl-1H-indol-5-ylamino)pyrimidin-4-yl)-3-methyl-1H-pyrazol-4-yl)ethyl)azetidin-3-ol; Compound 241

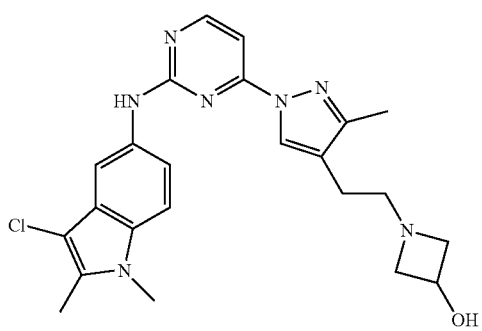 [SMILES: Cc1nn(-c2ccnc(Nc3ccc4c(c3)c(Cl)c(C)n4C)n2)cc1CCN1CC(O)C1]

MS (ESI) m/z 452 [M+H]$^+$ cis-1-((1-(2-(3-Chloro-1,2-dimethyl-1H-indol-5-ylamino)pyrimidin-4-yl)-3-methyl-1H-pyrazol-4-yl)methyl)pyrrolidine-3,4-diol; Compound 242

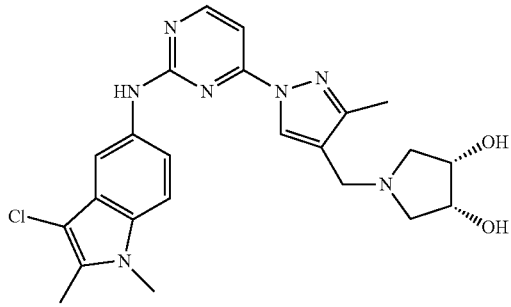 [SMILES: Cc1nn(-c2ccnc(Nc3ccc4c(c3)c(Cl)c(C)n4C)n2)cc1CN1C[C@@H](O)[C@@H](O)C1]

MS (ESI) m/z 468 [M+H]$^+$

114

(S)-1-((1-(2-(3-Chloro-1,2-dimethyl-1H-indol-5-ylamino)pyrimidin-4-yl)-3-methyl-1H-pyrazol-4-yl)methyl)pyrrolidine-2-carboxylic acid; Compound 243

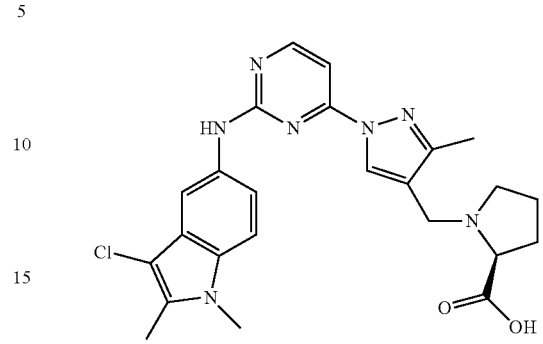

MS (ESI) m/z 480 [M+H]$^+$ (1S,2S)-2-((1-(2-(3-Chloro-1,2-dimethyl-1H-indol-5-ylamino)pyrimidin-4-yl)-3-methyl-1H-pyrazol-4-yl)methylamino)cyclohexanol; Compound 244

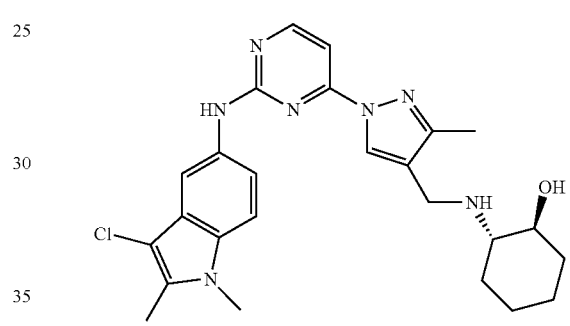

MS (ESI) m/z 480 [M+H]$^+$; $^1$H NMR (300 MHz, CDCl$_3$) δ 8.43 (s, 1H), 8.34 (d, J=5.4 Hz, 1H), 7.97 (s, 1H), 7.22 (s, 2H), 7.15 (d, J=5.4 Hz, 1H), 3.83 (d, J=13.5 Hz, 1H), 3.67 (s, 3H), 3.58 (d, J=13.5 Hz, 1H), 3.20-3.28 (m, 1H), 2.41 (s, 3H), 2.32 (s, 3H), 2.25-2.35 (m, 1H), 2.15-2.16 (m, 1H), 1.98-2.00 (m, 1H), 1.65-1.78 (m, 2H), 1.23-1.26 (m, 3H), 0.98-1.09 (m, 1H).

(1S,2S)—N1-((1-(2-(3-Chloro-1,2-dimethyl-1H-indol-5-ylamino)pyrimidin-4-yl)-3-methyl-1H-pyrazol-4-yl)methyl)cyclopentane-1,2-diamine; Compound 245

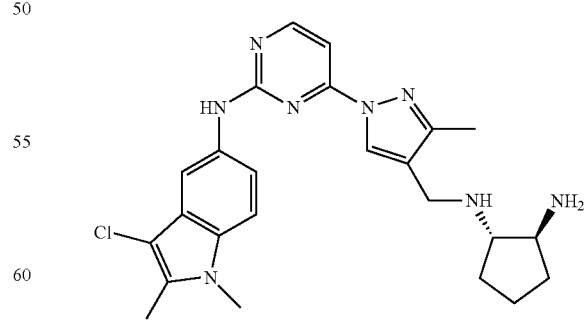

MS (ESI) m/z 465 [M+H]$^+$; $^1$H NMR (300 MHz, DMSO-d$_6$) δ 9.71 (s, 1H), 8.51-8.49 (d, J=5.4 Hz, 2H), 7.96 (s, 1H), 7.46 (s, 1H), 7.13 (d, J=5.4 Hz, 1H), 3.80 (s, 2H), 3.69 (s, 3H), 2.73 (m, 1H), 2.60 (m, 1H), 2.34 (s, 3H), 2.19 (m, 2H), 2.08 (m, 2H), 1.91 (s, 3H), 1.71 (m, 2H).

115 trans-4-((1-(2-(3-Chloro-1,2-dimethyl-1H-indol-5-ylamino)pyrimidin-4-yl)-3-methyl-1H-pyrazol-4-yl)methylamino)cyclohexanol; Compound 246

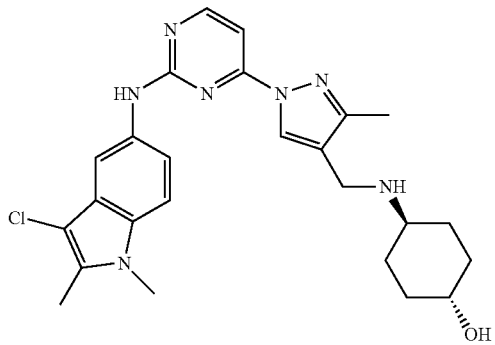 [SMILES: Cc1nn(-c2ccnc(Nc3ccc4c(c3)c(Cl)c(C)n4C)n2)cc1CN[C@H]1CC[C@H](O)CC1]

MS (ESI) m/z 480 [M+H]⁺; ¹H NMR (300 MHz, DMSO-d₆) δ 9.69 (s, 1H), 8.84 (s, 1H), 8.63 (s, 1H), 8.52 (d, J=5.4 Hz, 1H), 7.84 (s, 1H), 7.45 (q, 2H), 7.14 (d, J=5.4 Hz, 1H), 4.69 (d, 1H), 4.06 (s, 2H), 3.70 (s, 3H), 2.72 (t, 1H), 2.40 (s, 3H), 2.32 (s, 3H), 2.26 (m, 1H), 2.11 (dd, 2H), 1.91 (m, 2H), 1.40 (m, 2H), 1.22 (q, 2H).

(1S,2R)—N1-((1-(2-(3-Chloro-1,2-dimethyl-1H-indol-5-ylamino)pyrimidin-4-yl)-3-methyl-1H-pyrazol-4-yl)methyl)cyclohexane-1,2-diamine; Compound 247

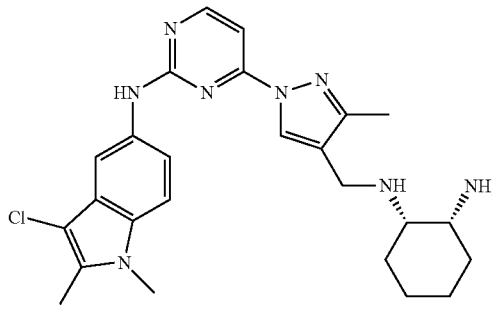

MS (ESI) m/z 479 [M+H]⁺

(1S,2S)-2-((1-(2-(3-Chloro-1,2-dimethyl-1H-indol-5-ylamino)pyrimidin-4-yl)-3-methyl-1H-pyrazol-4-yl)methylamino)cyclopentanol; Compound 248

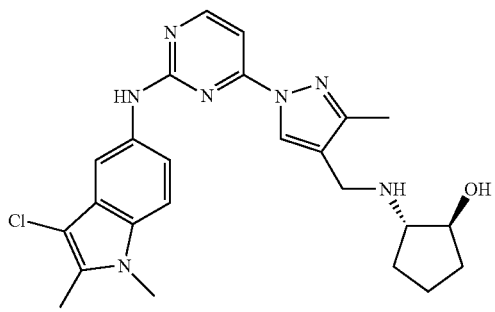 [SMILES: Cc1nn(-c2ccnc(Nc3ccc4c(c3)c(Cl)c(C)n4C)n2)cc1CN[C@H]1CCC[C@@H]1O]

MS (ESI) m/z 466 [M+H]⁺

116

(1S,3S)-3-((1-(2-(3-chloro-1,2-dimethyl-1H-indol-5-ylamino)pyrimidin-4-yl)-3-methyl-1H-pyrazol-4-yl)methylamino)cyclobutanol; Compound 249

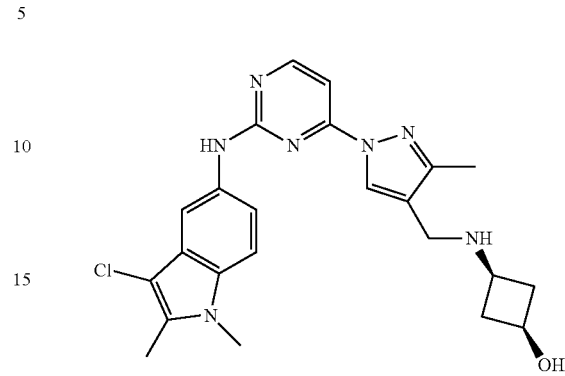

MS (ESI) m/z 452 [M+H]⁺

(3R,5S)-1-((1-(2-(3-Chloro-1,2-dimethyl-1H-indol-5-ylamino)pyrimidin-4-yl)-3-methyl-1H-pyrazol-4-yl)methyl)-5-(hydroxymethyl)pyrrolidin-3-ol; Compound 250

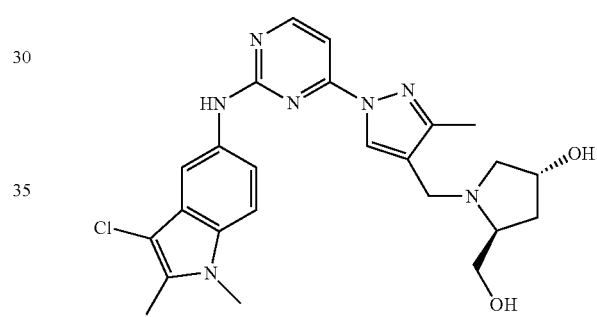

MS (ESI) m/z 482 [M+H]⁺; ¹H NMR (300 MHz, CDCl₃) δ 8.44 (s, 1H), 8.34 (d, J=5.4 Hz, 1H), 8.01 (br s, 1H), 7.15-7.24 (m, 3H), 4.29-4.32 (m, 1H), 8.34 (d, J=13.5 Hz, 1H), 3.51-3.71 (m, 4H), 3.45-3.49 (m, 2H), 3.25-3.30 (m, 1H), 3.04-3.07 (m, 1H), 2.41 (s, 3H), 2.31-2.42 (m, 1H), 2.32 (s, 3H), 1.98-2.16 (m, 1H), 1.84-1.89 (m, 1H).

(3S,4R)-1-((1-(2-(3-Chloro-1,2-dimethyl-1H-indol-5-ylamino)pyrimidin-4-yl)-3-methyl-1H-pyrazol-4-yl)methyl)-4-methoxypyrrolidin-3-ol; Compound 251

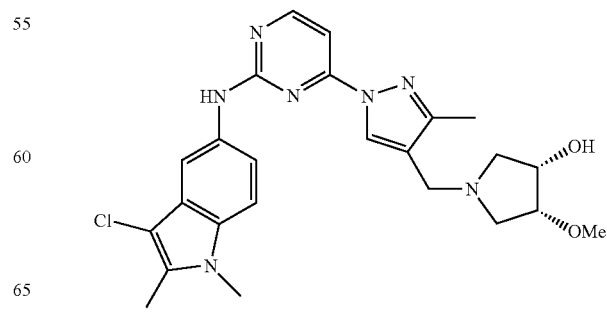

MS (ESI) m/z 482 [M+H]⁺

117

(3R,4R)-1-((1-(2-(3-Chloro-1,2-dimethyl-1H-indol-5-ylamino)pyrimidin-4-yl)-3-methyl-1H-pyrazol-4-yl)methyl)-4-isopropoxypyrrolidin-3-ol; Compound 252

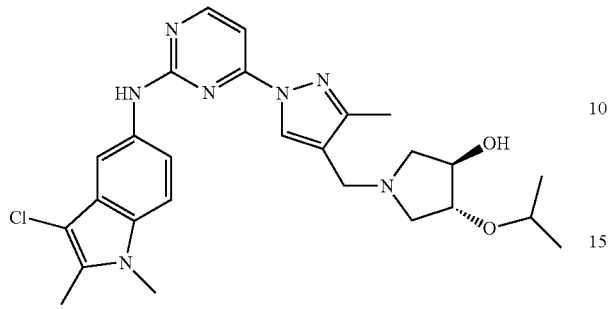

MS (ESI) m/z 510 [M+H]+; 1H NMR (300 MHz, CDCl3) δ 8.39-8.42 (m, 2H), 8.04 (br s, 1H), 7.20-7.24 (m, 3H), 4.07-4.09 (m, 1H), 3.90-3.94 (m, 1H), 3.68-3.74 (m, 4H), 3.55 (s, 2H), 3.20-3.26 (m, 1H), 2.65-2.78 (m, 2H), 2.45 (s, 3H), 2.35 (s, 3H), 2.19-2.24 (m, 1H), 1.15-1.20 (m, 6H).

cis-3-Chloro-N-(4-(4-((3,4-dimethoxypyrrolidin-1-yl)methyl)-3-methyl-1H-pyrazol-1-yl)pyrimidin-2-yl)-1,2-dimethyl-1H-indol-5-amine; Compound 253

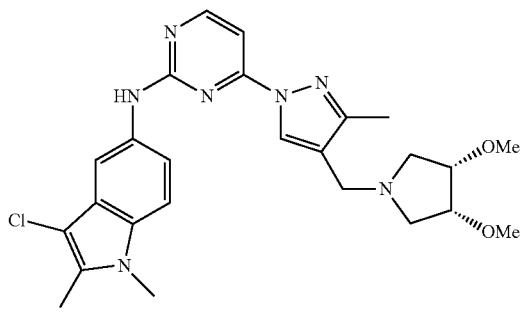 [SMILES: CO[C@H]1CN(Cc2cn(-c3ccnc(Nc4ccc5c(c4)c(Cl)c(C)n5C)n3)nc2C)C[C@H]1OC]

MS (ESI) m/z 496 [M+H]+; 1H NMR (300 MHz, DMSO-d6) δ 8.43 (d, 1H), 8.39 (s, 1H), 8.04 (s, 1H), 7.23 (t, 2H), 7.13 (s, 1H), 3.87 (t, 2H), 3.71 (s, 3H), 3.59 (s, 2H), 3.41 (s, 6H), 3.12 (q, 2H), 2.53 (dd, 2H), 2.45 (s, 3H), 1.56 (s, 3H).

(3R,5R)-1-((1-(2-(3-Chloro-1,2-dimethyl-1H-indol-5-ylamino)pyrimidin-4-yl)-3-methyl-1H-pyrazol-4-yl)methyl)-5-methylpyrrolidin-3-ol; Compound 254

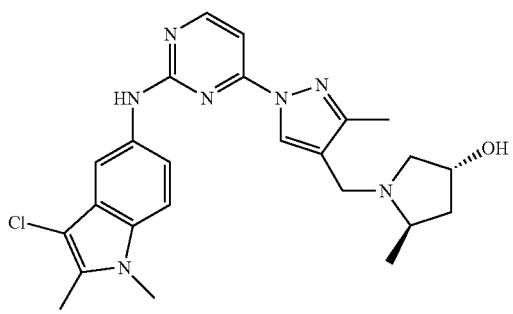 [SMILES: Cc1nn(-c2ccnc(Nc3ccc4c(c3)c(Cl)c(C)n4C)n2)cc1CN1C[C@H](O)C[C@H]1C]

MS (ESI) m/z 466 [M+H]+; 1H NMR (300 MHz, CDCl3) δ 8.44 (s, 1H), 8.40 (d, J=5.4, 1H), 8.07 (s, 1H), 7.21-7.33 (m, 3H), 4.36-4.38 (m, 1H), 3.87 (d, J=13.5 Hz, 1H), 3.41 (s, 3H), 3.27-3.41 (m, 2H), 2.81-2.88 (m, 1H), 2.44 (s, 3H), 2.36 (s, 3H), 2.21-2.24 (m, 1H), 1.74-1.94 (m, 2H), 1.20 (d, J=5.9 Hz, 3H).

118 cis-1-((3-Methyl-1-(2-(1-methyl-3-(methylsulfonyl)-1H-indazol-5-ylamino)pyrimidin-4-yl)-1H-pyrazol-4-yl)methyl)pyrrolidine-3,4-diol; Compound 255

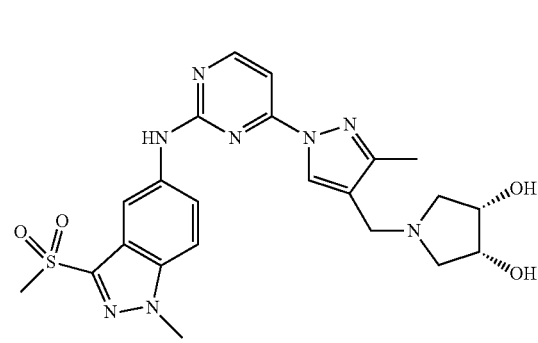 [SMILES: Cc1nn(-c2ccnc(Nc3ccc4c(c3)c(S(C)(=O)=O)nn4C)n2)cc1CN1C[C@@H](O)[C@@H](O)C1]

MS (ESI) m/z 499 [M+H]+

(3S,4R)-4-Methoxy-1-((3-methyl-1-(2-(1-methyl-3-(methylsulfonyl)-1H-indazol-5-ylamino)pyrimidin-4-yl)-1H-pyrazol-4-yl)methyl)pyrrolidin-3-ol; Compound 256

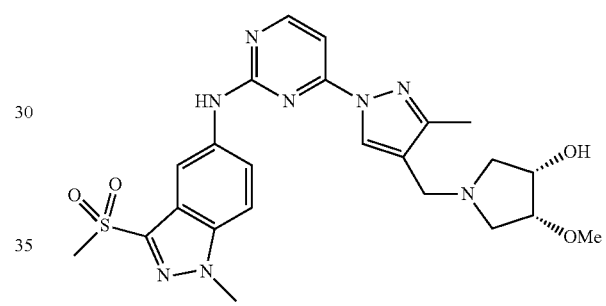

MS (ESI) m/z 513 [M+H]+; 1H NMR (300 MHz, DMSO-d6) δ 10.01 (s, 1H), 8.93 (s, 1H), 8.65 (s, 1H), 8.53 (d, J=5.4 Hz, 1H), 7.78 (d, J=9.0 Hz, 1H), 7.64 (d, J=9.0 Hz, 1H), 7.21 (d, J=5.4 Hz, 1H), 4.43 (s, 1H), 4.18 (s, 3H), 4.06 (q, 1H), 3.63 (q, 1H), 3.56 (s, 2H), 2.92 (q, 2H), 2.39 (s, 3H), 2.55 (q, 2H), 2.27 (s, 3H).

cis-1-((1-(2-(3-Bromo-1,2-dimethyl-1H-indol-5-ylamino)pyrimidin-4-yl)-3-methyl-1H-pyrazol-4-yl)methyl)pyrrolidine-3,4-diol; Compound 257

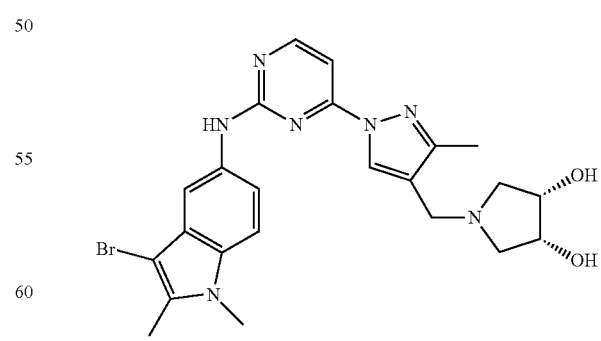

MS (ESI) m/z 512 [M+H]+; 1H NMR (300 MHz, DMSO-d6) δ 9.73 (s, 1H), 8.48 (d, J=5.4 Hz, 1H), 8.43 (s, 1H), 8.14 (s, 1H), 7.41 (s, 1H), 7.32 (dd, 1H), 7.10 (d, J=5.4 Hz, 1H), 3.93 (s, 2H), 3.71 (s, 3H), 2.89 (m, 2H), 2.50 (m, 2H), 2.32 (m, 2H), 2.25 (s, 3H), 1.84 (s, 3H).

119

1-((1-(2-(3-Chloro-2-methyl-1-propyl-1H-indol-5-ylamino)pyrimidin-4-yl)-3-methyl-1H-pyrazol-4-yl)methyl)azetidin-3-ol; Compound 258

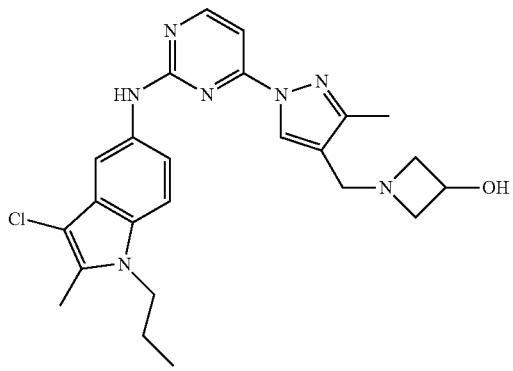 [SMILES: CCCn1c(C)c(Cl)c2cc(Nc3nccc(-n4cc(CN5CC(O)C5)c(C)n4)n3)ccc21]

MS (ESI) m/z 466 [M+H]$^+$; $^1$H NMR (300 MHz, DMSO-d$_6$) δ 8.36 (s, 1H), 8.34 (s, 1H), 7.96 (s, 1H), 7.67 (s, 1H), 7.22-7.15 (m, 3H), 4.45-4.37 (m, 1H), 3.39 (t, 2H), 3.61 (t, 3H), 3.47 (s, 2H), 2.96 (t, 2H), 2.39 (s, 3H), 2.28 (s, 3H), 1.81-1.68 (m, 2H), 0.92 (t, 3H).

cis-1-((1-(2-(3-Chloro-2-methyl-1-propyl-1H-indol-5-ylamino)pyrimidin-4-yl)-3-methyl-1H-pyrazol-4-yl)methyl)pyrrolidine-3,4-diol; Compound 259

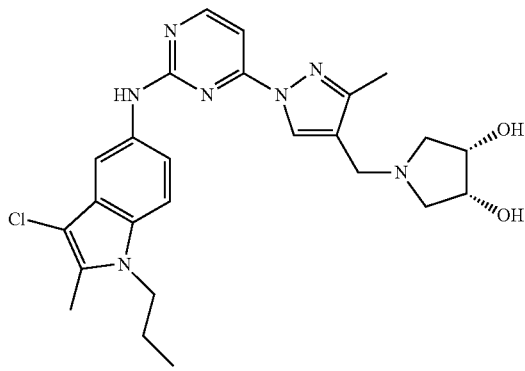 [SMILES: CCCn1c(C)c(Cl)c2cc(Nc3nccc(-n4cc(CN5C[C@@H](O)[C@@H](O)C5)c(C)n4)n3)ccc21]

MS (ESI) m/z 496 [M+H]$^+$ (3R,5S)-1-((1-(2-(3-Chloro-2-methyl-1-propyl-1H-indol-5-ylamino)pyrimidin-4-yl)-3-methyl-1H-pyrazol-4-yl)methyl)-5-(hydroxymethyl)pyrrolidin-3-ol; Compound 260

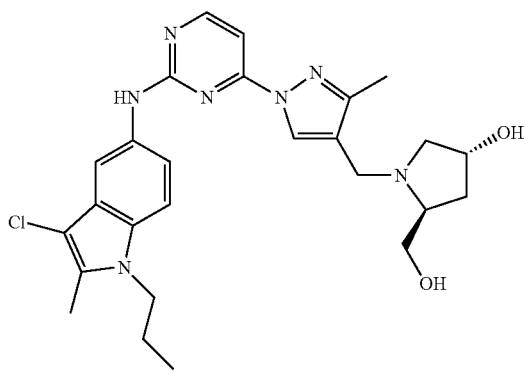 [SMILES: CCCn1c(C)c(Cl)c2cc(Nc3nccc(-n4cc(CN5C[C@H](O)C[C@H]5CO)c(C)n4)n3)ccc21]

MS (ESI) m/z 510 [M+H]$^+$

120

Cyclopropyl(5-(4-(4-((cis-3,4-dihydroxypyrrolidin-1-yl)methyl)-3-methyl-1H-pyrazol-1-yl)pyrimidin-2-ylamino)-1,2-dimethyl-1H-indol-3-yl)methanone; Compound 261

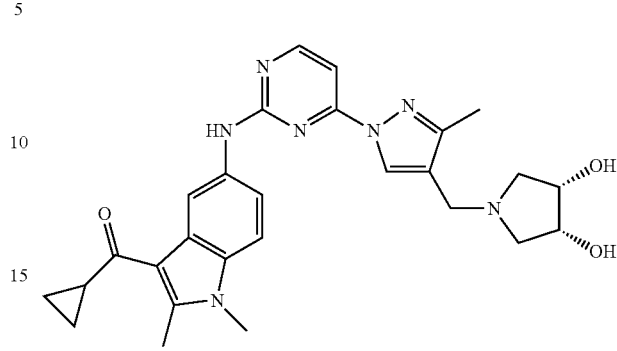

MS (ESI) m/z 502 [M+H]$^+$

Cyclopropyl(5-(4-(4-((3-hydroxyazetidin-1-yl)methyl)-3-methyl-1H-pyrazol-1-yl)pyrimidin-2-ylamino)-1,2-dimethyl-1H-indol-3-yl)methanone; Compound 262

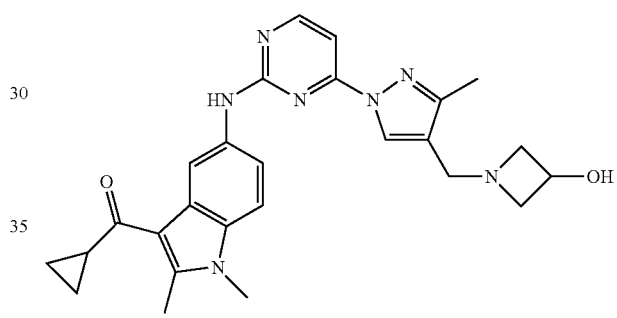

MS (ESI) m/z 472 [M+H]$^+$ 1-((1-(2-(3-Bromo-1-(2-methoxyethyl)-2-methyl-1H-indol-5-ylamino)pyrimidin-4-yl)-3-methyl-1H-pyrazol-4-yl)methyl)azetidin-3-ol; Compound 263

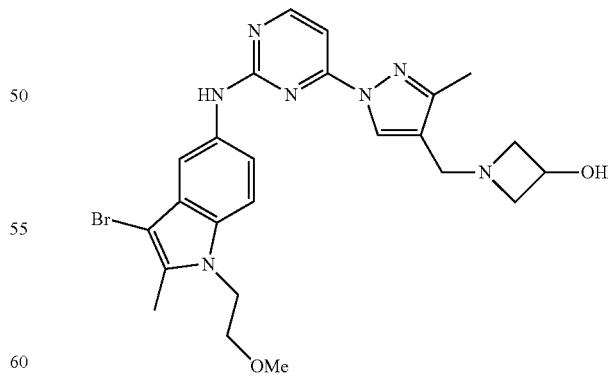

MS (ESI) m/z 526.1 [M+H]$^+$; $^1$H NMR (300 MHz, DMSO-d$_6$) δ 9.71 (s, 1H), 8.49 (s, J=5.1 Hz, 1H), 8.46 (d, 1H), 8.07 (s, 1H), 7.43 (d, J=8.7 Hz, 1H), 7.32 (d, J=8.7 Hz, 1H), 7.11 (d, J=5.1 Hz, 1H), 5.49 (s, 1H), 4.34 (t, 2H), 4.24 (m, 1H), 3.64 (s, 2H), 3.60 (t, 2H), 3.45 (d, 2H), 3.20 (s, 3H), 2.96 (d, 2H), 2.43 (s, 3H), 2.27 (s, 3H).

121

(R)-1-((1-(2-(3-Bromo-1-(2-methoxyethyl)-2-methyl-1H-indol-5-ylamino)pyrimidin-4-yl)-3-methyl-1H-pyrazol-4-yl)methyl)pyrrolidin-3-ol; Compound 264

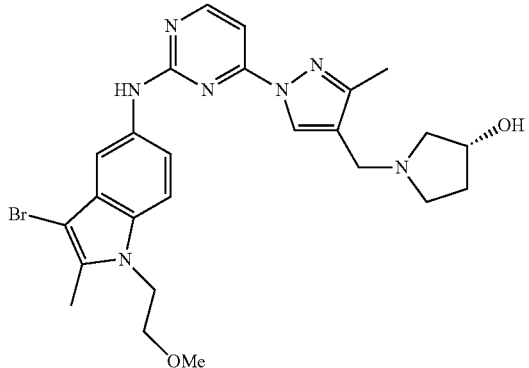 [SMILES: COCCn1c(C)c(Br)c2cc(Nc3nccc(-n4cc(CN5CC[C@@H](O)C5)c(C)n4)n3)ccc21]

MS (ESI) m/z 540 [M+H]+ cis-1-((1-(2-(3-Bromo-1-(2-methoxyethyl)-2-methyl-1H-indol-5-ylamino)pyrimidin-4-yl)-3-methyl-1H-pyrazol-4-yl)methyl)pyrrolidine-3,4-diol; Compound 265

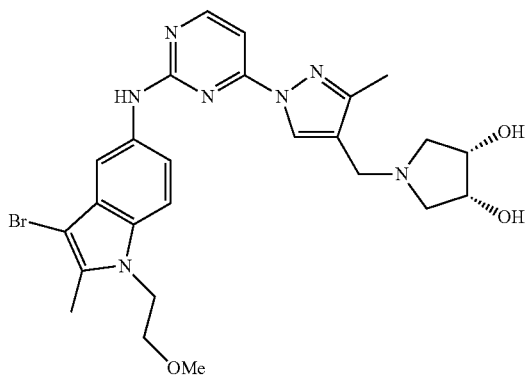

MS (ESI) m/z 556 [M+H]+ cis-1-((3-Methyl-1-(2-(1-methyl-3-(methyl sulfonyl)-1H-indol-5-ylamino)pyrimidin-4-yl)-1H-pyrazol-4-yl)methyl)pyrrolidine-3,4-diol; Compound 266

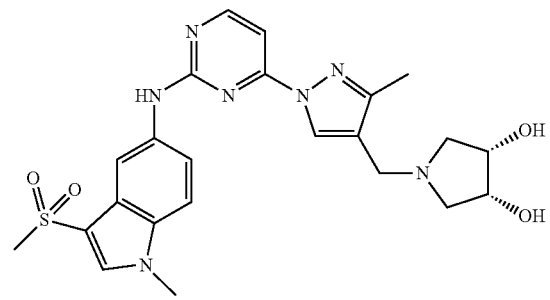 [SMILES: Cc1nn(-c2ccnc(Nc3ccc4c(c3)c(S(C)(=O)=O)cn4C)n2)cc1CN1C[C@@H](O)[C@@H](O)C1]

MS (ESI) m/z 498 [M+H]+

122 cis-1-((1-(2-(3-Chloro-1-(2-hydroxyethyl)-2-methyl-1H-indol-5-ylamino)pyrimidin-4-yl)-3-methyl-1H-pyrazol-4-yl)methyl)pyrrolidine-3,4-diol; Compound 267

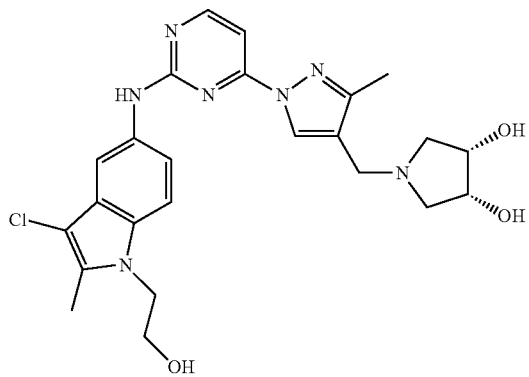 [SMILES: Cc1nn(-c2ccnc(Nc3ccc4c(c3)c(Cl)c(C)n4CCO)n2)cc1CN1C[C@@H](O)[C@@H](O)C1]

MS (ESI) m/z 498 [M+H]+

(3R,5S)-5-(Hydroxymethyl)-1-((3-methyl-1-(2-(1-methyl-3-(methylsulfonyl)-1H-indol-5-ylamino)pyrimidin-4-yl)-1H-pyrazol-4-yl)methyl)pyrrolidin-3-ol; Compound 268

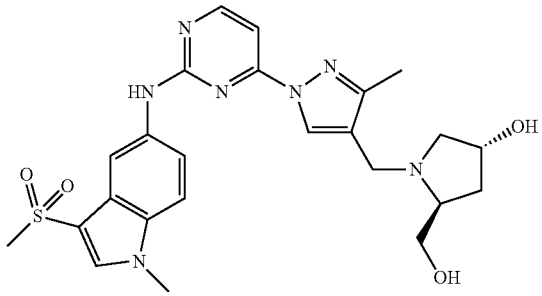 [SMILES: Cc1nn(-c2ccnc(Nc3ccc4c(c3)c(S(C)(=O)=O)cn4C)n2)cc1CN1C[C@H](O)C[C@H]1CO]

MS (ESI) m/z 512 [M+H]+ cis-1-((1-(2-(3-Cyclopentyl-1-methyl-1H-indol-5-ylamino)pyrimidin-4-yl)-3-methyl-1H-pyrazol-4-yl)methyl)pyrrolidine-3,4-diol; Compound 269

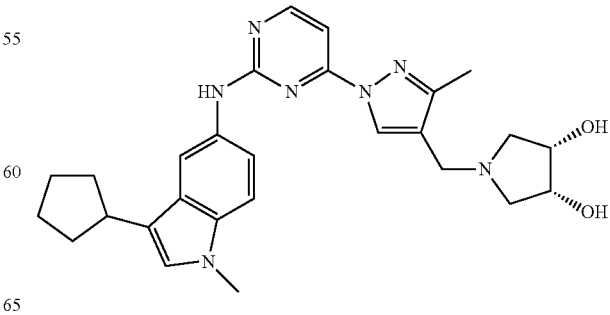

MS (ESI) m/z 488 [M+H]+

Biological Assays

1. Kinase Inhibition Assay

Compounds of the present invention were assayed to measure their capacity to inhibit a kinase panel which includes, but are not limited to, spleen tyrosine kinase (SYK) and kinase insert domain receptor (KDR, also known as vascular endothelial growth factor receptor 2, VEGFR2).

Spleen tyrosine kinase (SYK) is a member of the SYK family of tyrosine kinases which are non-receptor cytoplasmic tyrosine kinases sharing a characteristic dual SH2 domain separated by a linker domain. SYK plays a role in transmitting signals from a variety of cell surface receptors including CD74, Fc Receptor, and integrins. Abnormal function of SYK has been implicated in instances of hematopoeitic malignancies. Several transforming viruses, such as Epstein Barr virus, bovine leukemia virus, and mouse mammary tumor virus, are known to contain "Immunoreceptor Tyrosine Activation Motifs" (ITAMs) that lead to activation of SYK.

KDR (Kinase insert domain receptor, as known as vascular endothelial growth factor receptor 2, VEGFR2, CD309, or Flk1) is a type III receptor tyrosine kinase for vascular endothelial growth factor. It plays an essential role in the regulation of angiogenesis, vascular development, vascular permeability, and embryonic haematopoiesis. And it also promotes proliferation, survival, migration and differentiation of endothelial cells and promotes reorganization of the actin cytoskeleton.

Its misregulation or dysregulation plays a major role in tumor angiogenesis.

Methods

Inhibition of Enzymatic SYK, and KDR Kinase Activity

Compounds of the invention were initially diluted to 10 mM in 100% DMSO (CALBIOCHEM™) for storage and made into kinase buffer solution to create a compound concentration ranging from 1 uM and 10 uM. Serial dilutions of compounds of the invention were dispensed into a 96-well plate (GREINER BIOSCIENCES™) at 6 μL each. Purified full-length human SYK, and KDR (CARNA BIOSCIENCES™) were diluted in kinase buffer and added to the compound solutions and pre-incubated for 30 minutes at room temperature. Next, ATP (TEKNOVA™) of Km (15 uM) and substrate solution (suggested manufacture substrates of PerkinElmer™, for example, Ulight™-TK peptide for SYK and Ulight™-JAK1 for KDR (PERKINELMER™)) was added (12 uL each) to the wells containing the compound solution and enzyme. The reaction mixture was incubated for 1 hour. Following the incubation, the stop solution made with EDTA, water, and Lance detection buffer (PERKINELMER™) was added (12 μL each) to stop phosphorylation. Following the addition of the stop solution and 5 minutes of shaking, the detection solution containing the Europium-labeled antibody (suggested manufacture substrates of PerkinElmer™, for example, PT66 for SYK and KDR), water, and Lance detection buffer was added (12 μL each) to the reaction mixture and incubated again for 50 minutes. Substrate phosphorylation was a function of the 665 nm emission measured following the addition of the detection solution and 50 minutes of incubation.

Results

Compounds of Formula (I) exhibited useful pharmacological properties. As used herein, an way to describe potency of inhibitory activity (nM) is a value of inhibitory activity at 50% ($IC_{50}$). Reference compound, R406 (active form of R788, Rigel Pharmaceutical Inc.) was used for SYK to judge inhibitory activity of compounds of Formula (I). Reference compound, staurosporine, pan-kinase inhibitor was used for KDR to judge selectivity and inhibitory activity of compounds of Formula (I).

For example, Compound No. 52 of Formula (I), namely, 1-((4-methyl-1-(2-(1-methyl-1H-indol-5-ylamino)pyrimidin-4-yl)-1H-pyrrol-3-yl)methyl)azetidin-3-ol, was described in the previous file no PCT/US2010/056583. Its $IC_{50}$ against SYK and KDR are 190 nM and 1,688 nM respectively while $IC_{50}$s of R406 against two kinases are 88 nM and 22 nM, respectively. The previous invention (Compound No. 52) showed compatible potency and better selectivity than the reference compound R406. Some of compounds in this present invention are superior to the reference compound and others in the previous invention. For example, Compound No. 152, 1-(5-(4-(4-((3-hydroxyazetidin-1-yl)methyl)-3-methyl-1H-pyrazol-1-yl)pyrimidin-2-ylamino)-1-methyl-1H-indol-3-yl)ethanone showed 1.3 nM $IC_{50}$ against SYK kinases. It showed better selectivity and potency than R406 and Compound No 52.

Table 2 illustrates the inhibition of SYK and KDR by the representative compounds of Formula (I).

TABLE 2

Inhibition Activity of SYK and KDR

| Compound No. | SYK (IC50 nM) | KDR (IC50 nM) | Ratio of KDR to SYK |
|---|---|---|---|
| Staurosporine | 2.6 | 5.9 | 2.3 |
| R406 | 87.8 | 22 | 0.3 |
| 52 | 190.4 | 1688 | 8.9 |
| 141 | 1.0 | 192 | 192.0 |
| 144 | 1.8 | 357 | 198.0 |
| 152 | 1.3 | 345.6 | 265.8 |
| 160 | 15.2 | 1872 | 123.2 |
| 161 | 11.1 | 1117 | 100.6 |
| 163 | 12.6 | 1913 | 151.8 |
| 173 | 24.3 | 3895 | 160.3 |
| 176 | 1.0 | 1000 | 1000 |
| 180 | 2.1 | 290 | 138 |
| 182 | 1.5 | 150 | 100 |
| 189 | 1 | 1000 | 1000 |
| 190 | 0.1 | 483 | 4830 |
| 198 | 0.1 | 502 | 5020 |
| 201 | 1.3 | 581 | 447 |
| 231 | 13 | 9458 | 728 |
| 235 | 6.6 | 8372 | 1268 |
| 240 | 17.5 | 2109 | 121 |
| 251 | 0.6 | 731 | 1218 |
| 254 | 10 | 4272 | 427 |
| 255 | 0.7 | 647 | 924 |
| 258 | 1.2 | 486 | 405 |

As shown in Table 2, reference compounds, staurosporine and R406, are multi-potent, suggesting there is no selectivity across kinase whereas compounds of the present invention show better potency and better selectivity than reference compounds and Compound No. 52.

2. Tumor Necrosis Factor (TNF)-α Release Assay

Methods

For SYK-dependent TNF-α release assay (i.e., via IgG stimulation), THP-1 cells derived from human monocytic cells were obtained from the American Type Culture Collection (ATCC, Manassas, Va.). This cell line was maintained with a Roswell Park Memorial Institute (RPMI) medium (GIBCO) containing 10% fetal bovine serum (FBS; GIBCO) and 0.05 mM solution of 2-mercaptoethanol. The THP-1 cells were seeded at $1 \times 10^5$ cells/100 μL/well into human IgG (10 ng/well, INVITROGEN)-coated 96 well culture plate, and serially diluted compound was then added. After an 18 hours of incubation period at 37° C., supernatants were collected for the determination of the TNF-α level by enzyme-linked immunosorbent assay (ELISA), and the remaining cells were subjected to an MTT (yellow tetrazolium salt) assay to determine the cytotoxic effects of the compound. The $IC_{50}$ value of the test compound was calculated at Gradpad Prism 5 unless otherwise specified.

For SYK-independent TNF-α release assay, THP-1 cells were seeded at $1\times10^5$ cells/100 µL/well into 96 well culture plate, and serially diluted compound solution was added following lipopolysaccharide stimulation. After an 18-hour incubation period at 37° C., supernatants were collected for the determination of the TNF-α level by enzyme-linked immunosorbent assay (ELISA), and the remaining cells were subjected to an MTT (yellow tetrazolium salt) assay to determine the cytotoxic effects of compound. The $IC_{50}$ value of test compound was calculated at Gradpad Prism 5 unless otherwise specified.

Results

Compounds of Formula (I) exhibited useful pharmacological properties. As used herein, control used without the presence of an inhibitor indicates inhibition of TNF-α release in the $IC_{50}$.

Most of compounds of Formula (I) exhibited stronger inhibition than R406 control in a SYK dependent manner (e.g., IgG stimulation). Specifically, Compound No. 144 exhibited stronger inhibition than R406, a widely known kinase inhibitor, in SYK dependent TNF-α release assay (i.e., IgG stimulated release). In addition, Compound No. 144 showed no inhibition in LPS stimulated TNF-α production, SYK-independent pathway, suggesting that it inhibited SYK kinase activity resulting in TNF-α production in SYK dependent manner. The inhibition data ($IC_{50}$ value) of the representative compounds of Formula (I) of the present invention is shown in Table 3.

TABLE 3

TNF-α release inhibition/SYK dependent pathway by the representative compounds of Formula (I).

| Compound no. | IgG stimulation ($IC_{50}$ nM) | LPS stimulation ($IC_{50}$ nM) |
| --- | --- | --- |
| Dexamethasone | n.d. | 431 |
| R406 | 171 | n.d. |
| 52 | 94 | n.d. |
| 141 | 25 | >1000 |
| 144 | 13 | 1143 |
| 151 | 20 | >1000 |
| 160 | 91 | 934 |
| 161 | 50 | 1640 |
| 176 | 1090 | n.d. |
| 180 | 21 | n.d. |
| 189 | 42 | 2801 |
| 190 | 23 | n.d. |
| 251 | 79 | n.d. |
| 254 | 127 | n.d. |
| 255 | 52 | n.d. |
| 258 | 114 | n.d. | n.d. not determined.
IgG stimulation represents SYK-dependent pathway and LPS stimulation SYK-independent pathway.

3. Collagen-Induced Arthritis (CIA): Pre-Clinical Efficacy Models

CIA mouse model was induced in DBA/1J mice (Japan Charles River Breeding Laboratories, Kanagawa, Japan) with 5 to 6 weeks of age. Animals were maintained at a temperature of 20±5° C. and a relative humidity of 40~60%.

Bovine type II collagen (CII, 2 mg/ml dissolved in 0.05 M acetic acid, Chondrex, Redmond, Wash.) was emulsified in equal volumes of Freund's complete adjuvant (4 mg/ml of *Mycobacterium tuberculosis* strain H37Ra; Chondrex, Redmond, Wash.). On day 0, mice were immunized intradermally at the base of the tail with 100 µg bovine type II collagen emulsified in Freund's complete adjuvant. On day 21, all mice were boosted with an intraperitoneal injection of 100 µg type II collagen.

Method: Oral Administration of Compound

Compounds 141, 144, 160, 161 and R788 (reference, R406 prodrug) were used for this experiment. These compounds were dissolved in 20% hydroxypropyl beta-cyclodextrin and filtered by 0.25 µM membrane filter. All the test substances were administered once daily at 30 mg/kg/day by oral gavage for 3 weeks.

Method: Macroscopic Scoring of CIA Mice

The gradual onset of arthritis usually starts approximately 3 weeks after initial immunization. The progression of CIA was evaluated by the macroscopic scoring of paws at intervals of 3 days. The edema and swelling of each paw was scored visually as was described previously, using a scale of 0-4, where 0=no visible abnormalities, 1=mild redness or swelling of the wrist or up to three inflamed digits, 2=more than three inflamed digits or moderate redness and swelling of the ankle or wrist, 3=severe ankle and wrist inflammation, 4=extensive ankle and wrist inflammation including all digits. Therefore, the score of each mouse was calculated for the four limbs (maximum total score of 16 for each mouse) (Courtenay J S, Dallman M J, Dayan A D, et al., Immunisation against heterologous type II collagen induces arthritis in mice, Nature, 1980, 283, 666-668)

Arthritis was considered to be present if the score was >2. The blind scoring was performed by four independent observers. In this study, data was calculated by following equation.

Anti-arthritic activity(%)={Arthritic score of test compound group/Arthritic score of vehicle treated group}×100

Results

Compounds of Formula (I) exhibited useful pharmacological properties. As used herein, control used without the presence of an inhibitor indicates CIA index.

In certain embodiments, compounds of Formula (I) exhibited stronger inhibition than R788 control. Specifically, Compound No. 141 and Compound No. 144 of the present invention exhibited stronger inhibition in arthritis phenotype indicated by CIA than those exhibited by R788.

TABLE 4

CIA index by the representative compounds of Formula (I)

| Days | Vehicle | Compound No. 141 | Compound No. 144 | Compound No. 160 | Compound No. 161 | R788 |
| --- | --- | --- | --- | --- | --- | --- |
| 6 | 100 ± 5.6 | 40.6 ± 11.1 | 29.4 ± 6.8 | 42.0 ± 10.4 | 52.3 ± 12.2 | 41.9 ± 7.5 |
| 9 | 100 ± 2.5 | 34.4 ± 8.5 | 44.8 ± 9.1 | 58.4 ± 6.3 | 48.9 ± 11.1 | 49.6 ± 9.4 |
| 12 | 100 ± 3.4 | 33.6 ± 6.9 | 44.2 ± 4.5 | 63.8 ± 7.8 | 58.9 ± 6.9 | 68.3 ± 8.6 |

TABLE 4-continued

CIA index by the representative compounds of Formula (I)

| Days | Vehicle | Compound No. 141 | Compound No. 144 | Compound No. 160 | Compound No. 161 | R788 |
|---|---|---|---|---|---|---|
| 15 | 100 ± 10.1 | 38.0 ± 8.1 | 47.3 ± 7.6 | 58.2 ± 9.8 | 67.6 ± 8.4 | 74.1 ± 7.1 |
| 18 | 100 ± 6.1 | 42.5 ± 5.7 | 52.9 ± 8.1 | 70.7 ± 6.9 | 76.3 ± 9.7 | 79.4 ± 10.7 |
| 21 | 100 ± 7.4 | 45.4 ± 3.9 | 57.6 ± 6.5 | 74.7 ± 7.4 | 80.6 ± 9.1 | 80.1 ± 6.7 |

The disclosures of each and every patent, patent application and publication cited herein are hereby incorporated herein by reference in their entirety.

While this invention has been particularly shown and described in example embodiments thereof, it will be understood by those skilled in the art that various changes in form and details may be made therein without departing from the scope of the invention encompassed by the appended claims.

The invention claimed is:

1. A compound of Formula (I):

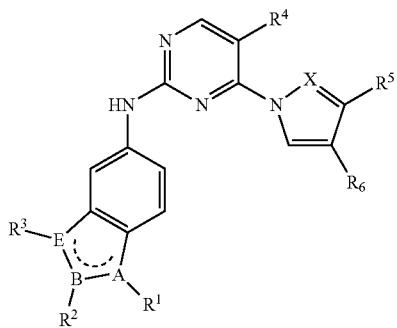

Formula I

Wherein:

X is CH or N

═══ is a single or a double bond;

A is C;

B is C;

E is C;

$R^1$ is selected from H, $C_1$-$C_6$alkyl, $C_3$-$C_7$cycloalkyl, $C_5$-$C_8$heterocycloalkyl, aryl, arylalkyl, heteroaryl, C(O)$NR^7R^7C(O)R^7$, S(O)$_n$$R^7$, S(O)$_n$$NR^7R^7$, C(O)$NR^8R^9$, or S(O)$_n$$NR^8R^9$, wherein each n is 1 or 2 and the $C_1$-$C_6$ alkyl, $C_3$-$C_7$cycloalkyl, $C_5$-$C_8$heterocycloalkyl, aryl, arylalkyl, or heteroaryl is optionally substituted with one or more halo, amino, hydroxy, $OR^7$, $NHR^7$, $NR^7R^7$, $NR^8R^9$, or $C_3$-$C_7$cycloalkyl;

$R^8$ and $R^9$, taken together with the nitrogen atom to which they are bonded form:

i) a 3-8 membered saturated or partially saturated monocyclic group having no heteroatom other than the nitrogen atom to which $R^8$ and $R^9$ are bonded, wherein said 3-8 membered saturated or partially saturated monocyclic group is optionally and independently substituted at one or more carbon atoms with halo, amino, hydroxy, $R^7$, $OR^7$, $SR^7$, $NHR^7$, $NR^7R^7$, or $NR^8R^9$; or ii) a 5-8 membered saturated or partially saturated monocyclic group having 1 or 2 heteroatoms selected from nitrogen, oxygen, sulfur, sulfone or sulfoxide, wherein said 5-8 membered saturated or partially saturated monocyclic group having 1 or 2 heteroatoms is optionally substituted with $R^7$;

$R^2$ is selected from H, halo, $CF_3$, $C_1$-$C_4$alkyl or aryl, wherein the $C_1$-$C_4$alkyl or aryl is optionally substituted with one or more halo, amino, hydroxy, alkoxy, or haloalkyl;

$R^3$ is selected from C(O)$NR^7R^7$, C(O)$R^7$, S(O)$_n$$R^7$, S(O)$_n$ $NR^7R^7$, C(O)$NR^8R^9$, or S(O)$_n$$NR^8R^9$, wherein each n is 1 or 2;

$R^4$ is selected from H, halo, $C_1$-$C_6$alkyl, $C_3$-$C_7$cycloalkyl, wherein the $C_1$-$C_6$alkyl, or $C_3$-$C_7$cycloalkyl is optionally substituted with one or more halo, amino, hydroxy, alkoxy, or haloalkyl;

$R^5$ is selected from H, halo, $C_1$-$C_6$alkyl, $CF_3$, CN, $C_3$-$C_7$cycloalkyl, aryl or $C_5$-$C_8$heteroaryl, wherein $C_3$-$C_7$cycloalkyl, aryl or $C_5$-$C_8$heteroaryl is optionally and independently substituted with one or more halo, amino, hydroxy, alkoxy, or haloalkyl;

$R^6$ is selected from $CH_2OH$, $(CH_2)_nNH_2$, $(CH_2)_nOR^7$, $(CH_2)_nNHR^7$, $(CH_2)_nNR^7R^7$, $(CH_2)_nNR^7R^{10}$, C(O) $NHR^7$, C(O)$NR^7R^7$, C(O)$NR^7R^{10}$, $(CH_2)_nC(O)OR^7$, C(O)$R^7$, $(CH_2)_nNHS(O)_nR^7$, $(CH_2)_nNR^7S(O)_nR^7$, $(CH_2)_nNR^{11}R^{12}$, C(O)$NR^{11}R^{12}$, or $(CH_2)_nCN$, wherein each n is independently 1 or 2;

$R^7$ is independently selected from $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl, wherein the $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocyclyl is optionally and independently substituted with one or more aryl, cycloalkyl, heteroaryl, heterocyclyl, alkyl, halo, amino, hydroxy, or $R^{13}$;

Each $R^{10}$ is independently selected from C(O)$R^7$, C(O) $OR^7$, C(O)$NR^7R^7$ or S(O)$_n$$R^7$, wherein n is 1 or 2;

Each $R^{13}$ is independently selected from $SR^7$, $OR^7$, $NR^7R^7$, C(O)$NR^7R^7$, S(O)$_n$$NR^7R^7$, S(O)$_n$$R^7$, $NR^8R^9$, or C(O)$R^8R^9$, wherein each n is independently 1 or 2;

$R^{11}$ and $R^{12}$, taken together with the nitrogen atom to which they are bonded form:

i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbon atoms with $R^{14}$, wherein $R^{14}$ is COOH, COOR$^7$, CN, $(CH_2)_nOH$, $(CH_2)_nOR^7$, halo, amino, hydroxy, $R^7$, $OR^7$, $SR^7$, $NHR^7$, $NR^7R^7$, $NR^8R^9$, NHC(O)$NHR^7$, NHC(O)$NR^7R^7$, OC(O)$R^7$, NHC(O) $NR^8R^9$, NHS(O)$_n$$R^7$, NHS(O)$_n$$NHR^7$, wherein n is 1 or 2; or ii) a 5-8 membered saturated or partially saturated monocyclic group having 1 or 2 heteroatoms selected from nitrogen, oxygen, sulfur, sulfone, or sulfoxide, wherein said 5-8 membered saturated or partially saturated monocyclic group having 1 or 2 heteroatoms is optionally substituted with $R^7$;

or a pharmaceutically acceptable salt thereof.

2. The compound of claim 1, wherein $R^1$ is an alkyl selected from methyl, ethyl, propyl, isopropyl, butyl, cyclopropyl, cyclobutyl, cyclopentyl, 2-hydroxyethyl, 2-methoxyethyl, 2-morpholinylethyl, 2-pyrrolidinylethyl, tetrahydropyranyl, arylalkyl, phenyl, pyridyl, or cyclopropylmethyl.

3. The compound of claim 1, wherein $R^1$ is selected from acetyl, propionyl, cyclopropylcarbonyl, trifluoromethylcarbonyl, methanesulfonyl, ethanesulfonyl, N,N-dimethylcarbonyl, or pyrrolidinylcarbonyl.

4. The compound of claim 1, wherein $R^2$ is H, halo, $CF_3$, $C_1$-$C_4$alkyl or aryl, wherein the $C_1$-$C_4$alkyl or aryl is optionally substituted with one or more halo, amino, hydroxy, alkoxy, or haloalkyl.

5. The compound of claim 1, wherein $R^3$ is selected from acetyl, propionyl, cyclopropyl carbonyl, trifluoromethyl carbonyl, methanesulfonyl, ethanesulfonyl, cyclopropanesulfonyl, benzenesulfonyl, p-toluenesulfonyl, N,N-dimethylaminocarbonyl, morpholinylcarbonyl, or pyrrolidinylcarbonyl.

6. The compound of claim 1, wherein $R^4$ is selected from H, F, Cl, Br, $CH_3$, $CF_3$, ethyl, cyclopropyl, or cyclobutyl.

7. The compound of claim 1, wherein $R^5$ is selected from H, Cl, Br, $CH_3$, $CF_3$, CN, ethyl, isopropyl, cyclopropyl, cyclobutyl, or phenyl.

8. The compound of claim 1, wherein $R^6$ is $(CH_2)_n NR^{11}R^{12}$ or $C(O)NR^{11}R^{12}$, wherein each n is independently 1 or 2; $R^{11}$ and $R^{12}$, taken together with the nitrogen atom to which they are bonded form a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbon atoms with $R^{14}$, wherein $R^{14}$ is COOH, $COOR^7$, $(CH_2)_nOH$, $(CH_2)_nOR^7$, halo, amino, hydroxy, $R^7$, $OR^7$, $SR^7$, $NHR^7$, $NR^7R^7$, $NR^8R^9$, NHC(O)$NHR^7$, $NHC(O)NR^7R^7$, $OC(O)R^7$, $NHC(O)NR^8R^9$, $NHS(O)_nR^7$, $NHS(O)_nNHR^7$, wherein n is 1 or 2.

9. The compound of claim 8, wherein the 3-8 membered saturated or partially saturated monocyclic ring having no heteroatom other than the bound nitrogen is 4-6 membered saturated rings optionally and independently substituted with one or more hydroxy, amino, halo, COOH, $COOR^7$, $R^7$, $OR^7$, $SR^7$, $NHR^7$, $NR^7R^7$, $NR^8R^9$, $NHC(O)NHR^7$, $NHC(O)NR^7R^7$, $OC(O)R^7$, $NHC(O)NR^8R^9$, $NHS(O)_nR^7$, or NHS$(O)_n$NHR at one or more substitutable carbon atoms.

10. The compound of claim 9, wherein the 4-6 membered ring is selected from azetidinyl, pyrrolidinyl, or piperidinyl optionally and independently substituted with one or more hydroxy, amino, halo, COOH, $COOR^7$, $(CH_2)_nOH$, $(CH_2)_n OR^7$, $R^7$, $OR^7$, $SR^7$, $NHR^7$, $NR^7R^7$, $NR^8R^9$, $NHC(O)NHR^7$, $NHC(O)NR^7R^7$, $OC(O)R^7$, $NHC(O)NR^8R^9$, $NHS(O)_nR^7$, or NHS$(O)_n$NHR at one or more substitutable carbon atoms.

11. A compound selected from the group consisting of:
Cyclopropyl(5-(4-(4-((3-hydroxyazetidin-1-yl)methyl)-3-methyl-1H-pyrazol-1-yl)pyrimidin-2-ylamino)-1H-indol-1-yl)methanone;
2,2,2-Trifluoro-1-(5-(4-(4-((3-hydroxyazetidin-1-yl)methyl)-3-methyl-1H-pyrazol-1-yl)pyrimidin-2-ylamino)-1-methyl-1H-indol-3-yl)ethanone;
1-(5-(4-(4-((3-Hydroxyazetidin-1-yl)methyl)-3-methyl-1H-pyrazol-1-yl)pyrimidin-2-ylamino)-1-methyl-1H-indol-3-yl)ethanone;
5-(4-(4-((3-Hydroxyazetidin-1-yl)methyl)-3-methyl-1H-pyrazol-1-yl)pyrimidin-2-ylamino)-N,N,1-trimethyl-1H-indole-3-carboxamide;
(5-(4-(4-((3-Hydroxyazetidin-1-yl)methyl)-3-methyl-1H-pyrazol-1-yl)pyrimidin-2-ylamino)-1H-indol-3-yl)(morpholino)methanone;
(5-(4-(4-((3-Hydroxyazetidin-1-yl)methyl)-3-methyl-1H-pyrazol-1-yl)pyrimidin-2-ylamino)-1,2-dimethyl-1H-indol-3-yl)(pyrrolidin-1-yl)methanone;
Cyclopropyl(5-(4-(4-((3-hydroxyazetidin-1-yl)methyl)-3-methyl-1H-pyrazol-1-yl)pyrimidin-2-ylamino)-1-methyl-1H-indol-3-yl)methanone
1-((3-Methyl-1-(2-(1-methyl-3-(pyrrolidin-1-ylsulfonyl)-1H-indol-5-ylamino)pyrimidin-4-yl)-1H-pyrazol-4-yl)methyl)azetidin-3-ol;
2,2,2-Trifluoro-1-(5-(4-(4-((3-hydroxyazetidin-1-yl)methyl)-3-methyl-1H-pyrazol-1-yl)pyrimidin-2-ylamino)indolin-1-yl)ethanone;
1-((3-Methyl-1-(2-(1-methyl-3-tosyl-1H-indol-5-ylamino)pyrimidin-4-yl)-1H-pyrazol-4-yl)methyl)azetidin-3-ol;
(R)-Cyclopropyl(5-(4-(4-((3-hydroxypyrrolidin-1-yl)methyl)-3-methyl-1H-pyrazol-1-yl)pyrimidin-2-ylamino)-1-methyl-1H-indol-3-yl)methanone;
(R)-Cyclopropyl(5-(4-(4-((3-hydroxypiperidin-1-yl)methyl)-3-methyl-1H-pyrazol-1-yl)pyrimidin-2-ylamino)-1-methyl-1H-indol-3-yl)methanone;
(1-(2-(1-Cyclopropyl-3-methyl-1H-indol-5-ylamino)pyrimidin-4-yl)-3-methyl-1H-pyrazol-4-yl)(3-hydroxyazetidin-1-yl)methanone;
(R)-2,2,2-Trifluoro-1-(5-(6-(3-((3-hydroxypyrrolidin-1-yl)methyl)-4-methyl-1H-pyrrol-1-yl)pyridin-2-ylamino)-1-methyl-1H-indol-3-yl)ethanone;
1-(5-(4-(4-(((3R,4S)-3,4-Dihydroxypyrrolidin-1-yl)methyl)-3-methyl-1H-pyrazol-1-yl)pyrimidin-2-ylamino)-1H-indol-3-yl)ethanone;
(R)-1-(5-(4-(4-((3-hydroxypyrrolidin-1-yl)methyl)-3-methyl-1H-pyrazol-1-yl)pyrimidin-2-ylamino)-1H-indol-3-yl)ethanone;
1-(5-(4-(4-((3-Hydroxyazetidin-1-yl)methyl)-3-methyl-1H-pyrazol-1-yl)pyrimidin-2-ylamino)-1H-indol-3-yl)ethanone;
1-(5-(4-(4-(((3R,4S)-3,4-Dihydroxypyrrolidin-1-yl)methyl)-3-methyl-1H-pyrazol-1-yl)pyrimidin-2-ylamino)-1H-indol-3-yl)-2,2,2-trifluoroethanone;
(R)-2,2,2-trifluoro-1-(5-(4-(4-((3-Hydroxypyrrolidin-1-yl)methyl)-3-methyl-1H-pyrazol-1-yl)pyrimidin-2-ylamino)-1H-indol-3-yl)ethanone;
2,2,2-Trifluoro-1-(5-(4-(4-(((2S,4R)-4-hydroxy-2-(hydroxymethyl)pyrrolidin-1-yl)methyl)-3-methyl-1H-pyrazol-1-yl)pyrimidin-2-ylamino)-1H-indol-3-yl)ethanone;
1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2,2,2-trifluoroethanone;
2,2,2-Trifluoro-1-(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)ethanone;
2,2,2-Trifluoro-1-(5-(4-(4-(((2S,4R)-4-hydroxy-2-(hydroxymethyl)pyrrolidin-1-yl)methyl)-3-methyl-1H-pyrazol-1-yl)pyrimidin-2-ylamino)-1-methyl-1H-indol-3-yl)ethanone;
Cyclopropyl(5-(4-(4-(((3R,4S)-3,4-dihydroxypyrrolidin-1-yl)methyl)-3-methyl-1H-pyrazol-1-yl)pyrimidin-2-ylamino)-1-methyl-1H-indol-3-yl)methanone;
Cyclopropyl(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)methanone;

Cyclopropyl(5-(4-(4-(((3S,4S)-3,4-dihydroxypyrrolidin-1-yl)methyl)-3-methyl-1H-pyrazol-1-yl)pyrimidin-2-ylamino)-1-methyl-1H-indol-3-yl)methanone;

(3R,4S)-1-((1-(2-(3-(Cyclopropanecarbonyl)-1-methyl-1H-indol-5-ylamino)pyrimidin-4-yl)-3-methyl-1H-pyrazol-4-yl)methyl)pyrrolidine-3,4-dihydroxyl diacetate;

Cyclopropyl(5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)methanone;

Cyclopropyl(5-(4-(4-(((3S,4R)-3-hydroxy-4-methoxypyrrolidin-1-yl)methyl)-3-methyl-1H-pyrazol-1-yl)pyrimidin-2-ylamino)-1H-indol-3-yl)methanone;

(R)-Cyclopropyl(5-(4-(4-((3-hydroxypyrrolidin-1-yl)methyl)-3-methyl-1H-pyrazol-1-yl)pyrimidin-2-ylamino)-1H-indol-3-yl)methanone;

1-(5-(4-(4-(((3R,4S)-3,4-Dihydroxypyrrolidin-1-yl)methyl)-3-methyl-1H-pyrazol-1-yl)pyrimidin-2-ylamino)-1H-indol-3-yl)-2,2-difluoroethanone;

(R)-2,2-Difluoro-1-(5-(4-(4-((3-hydroxypyrrolidin-1-yl)methyl)-3-methyl-1H-pyrazol-1-yl)pyrimidin-2-ylamino)-1H-indol-3-yl)ethanone;

1-(5-(4-(4-(((3S,4S)-3,4-Dihydroxypyrrolidin-1-yl)methyl)-3-methyl-1H-pyrazol-1-yl)pyrimidin-2-ylamino)-1H-indol-3-yl)-2,2-difluoroethanone;

2,2-Difluoro-1-(5-(4-(4-(((3S,4R)-3-hydroxy-4-methoxypyrrolidin-1-yl)methyl)-3-methyl-1H-pyrazol-1-yl)pyrimidin-2-ylamino)-1-methyl-1H-indol-3-yl)ethanone;

1-(5-(4-(4-(((3S,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-difluoroethanone;

(R)-2,2-Difluoro-1-(5-(4-(4-((3-hydroxypyrrolidin-1-yl)methyl)-3-methyl-1H-pyrazol-1-yl)pyrimidin-2-ylamino)-1-methyl-1H-indol-3-yl)ethanone;

1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one;

1-(5-(4-(4-(((3S,4S)-3,4-Dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one;

(R)-1-(5-(4-(4-((3-Dihydroxypyrrolidin-1-yl)methyl)-3-methyl-1H-pyrazol-1-yl)pyrimidin-2-ylamino)-1-methyl-1H-indol-3-yl)-2,2-dimethylpropan-1-one;

Cyclopropyl(1-cyclopropyl-5-(4-(4-(((3R,4S)-3,4-dihydroxypyrrolidin-1-yl)methyl)-3-methyl-1H-pyrazol-1-yl)pyrimidin-2-ylamino)-1H-indol-3-yl)methanone;

(R)-Cyclopropyl(1-cyclopropyl-5-(4-(4-((3-hydroxypyrrolidin-1-yl)methyl)-3-methyl-1H-pyrazol-1-yl)pyrimidin-2-ylamino)-1H-indol-3-yl)methanone;

(R)-Cyclopropyl(1-cyclopropyl-5-(4-(4-((3-methoxypyrrolidin-1-yl)methyl)-3-methyl-1H-pyrazol-1-yl)pyrimidin-2-ylamino)-1H-indol-3-yl)methanone;

1-(5-(4-(4-(((3R,4S)-3,4-Dihydroxypyrrolidin-1-yl)methyl)-3-methyl-1H-pyrazol-1-yl)pyrimidin-2-ylamino)-1-methyl-1H-indol-3-yl)-2-methylpropan-1-one;

1-(5-(4-(4-(((3S,4S)-3,4-Dihydroxypyrrolidin-1-yl)methyl)-3-methyl-1H-pyrazol-1-yl)pyrimidin-2-ylamino)-1-methyl-1H-indol-3-yl)-2-methylpropan-1-one;

(R)-1-(5-(4-(4-((3-Hydroxypyrrolidin-1-yl)methyl)-3-methyl-1H-pyrazol-1-yl)pyrimidin-2-ylamino)-1-methyl-1H-indol-3-yl)-2-methylpropan-1-one;

1-(5-(4-(4-(((3S,4R)-3-Hydroxy-4-methoxypyrrolidin-1-yl)methyl)-3-methyl-1H-pyrazol-1-yl)pyrimidin-2-ylamino)-1-methyl-1H-indol-3-yl)-2-methylpropan-1-one;

Cyclopropyl(5-(4-(4-(((3R,4S)-3,4-dihydroxypyrrolidin-1-yl)methyl)-3-methyl-1H-pyrazol-1-yl)pyrimidin-2-ylamino)-1,2-dimethyl-1H-indol-3-yl)methanone;

Cyclopropyl(5-(4-(4-((3-hydroxyazetidin-1-yl)methyl)-3-methyl-1H-pyrazol-1-yl)pyrimidin-2-ylamino)-1,2-dimethyl-1H-indol-3-yl)methanone;

Cyclopropyl(5-(4-(4-((cis-3,4-dihydroxypyrrolidin-1-yl)methyl)-3-methyl-1H-pyrazol-1-yl)pyrimidin-2-ylamino)-1,2-dimethyl-1H-indol-3-yl)methanone;

Cyclopropyl(5-(4-(4-((3-hydroxyazetidin-1-yl)methyl)-3-methyl-1H-pyrazol-1-yl)pyrimidin-2-ylamino)-1,2-dimethyl-1H-indol-3-yl)methanone;

cis-1-((3-Methyl-1-(2-(1-methyl-3-(methanesulfonyl)-1H-indol-5-ylamino)pyrimidin-4-yl)-1H-pyrazol-4-yl)methyl)pyrrolidine-3,4-diol; and (3R,5S)-5-(Hydroxymethyl)-1-((3-methyl-1-(2-(1-methyl-3-(methanesulfonyl)-1H-indol-5-ylamino)pyrimidin-4-yl)-1H-pyrazol-4-yl)methyl)pyrrolidin-3-ol;

or a pharmaceutically acceptable salt thereof.

12. A pharmaceutical formulation comprising a compound of claim 1, or a pharmaceutically acceptable salt thereof, in combination with a pharmaceutically acceptable carrier, diluent, or excipient.

13. A process for preparing a compound of Formula (I) according to claim 1, the process comprising:

i. reacting a compound of formula (a) with a compound of formula (b) in a first organic solvent in the presence of a first base to give a compound of formula (c);

ii. reacting the compound of formula (c) with an aniline derivative of formula (d) in the presence of a second base, a ligand and a palladium catalyst in a second solvent to give a compound of formula (e);

iii. reacting the compound of formula (e) with an amine derivative ($R^6$) in a third organic solvent in the presence of reducing agent such as $NaBH(OAc)_3$ to give a compound of Formula I;

iv. reacting the compound of formula (c) with an amine derivative ($R^6$) in a third organic solvent in the presence of reducing agent such as $NaBH(OAc)_3$ to give a compound of formula (f);

v. reacting the compound of formula (f) with an aniline derivative formula (d) in the presence of a second base and a palladium catalyst to give a compound of Formula I;

or the compound of formula (e) is prepared by the following steps:

vi. reacting a compound of formula (a) with $CH_3SNa$ in a fourth organic solvent to give a compound of formula (g);

vii. reacting the compound of formula (g) o with an aniline derivative in a fourth solvent in the presence of HCl to give a compound of formula (h);

viii. oxidizing the compound of formula (h) in a fifth organic solvent to give a compound of formula (I); and ix. reacting the compound of formula (I) with a compound of formula (b) in a fourth organic solvent in the presence of a third base to give a compound of formula (e);

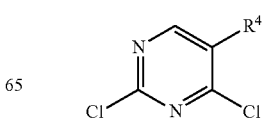

-continued

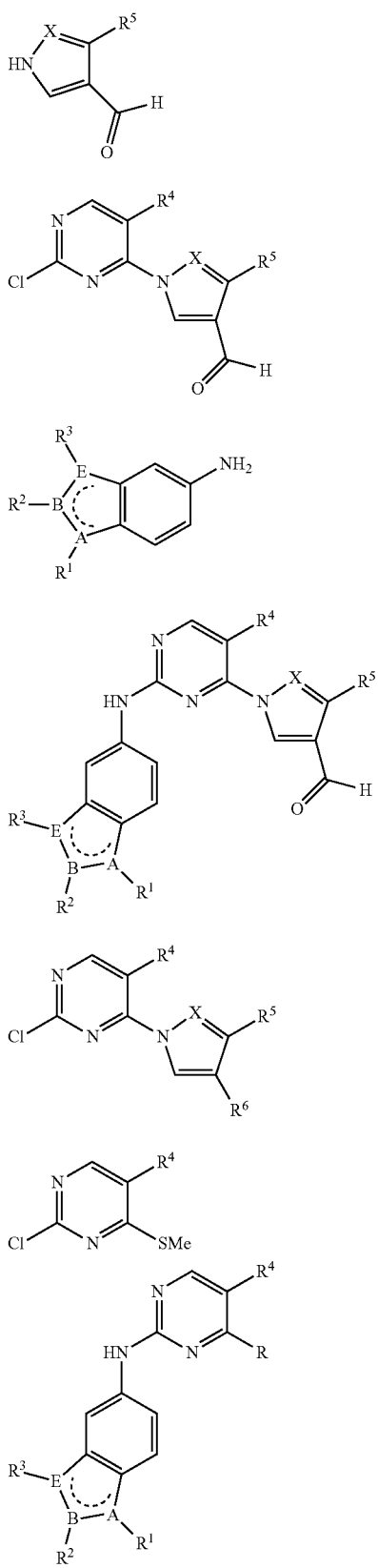

h: R = SMe
i: R = SO₂Me

-continued

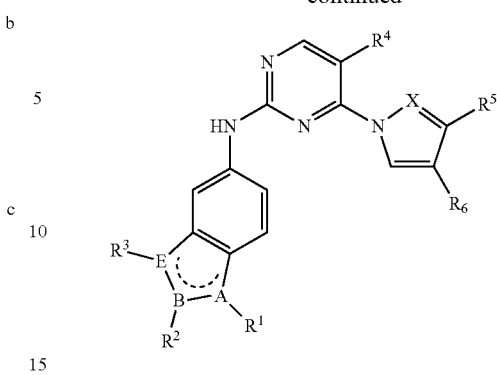

Formula (I)

wherein: A, B, E R¹, R², R³, R⁴, R⁵, R⁶ and X are described in claim 1.

14. A process according to claim 13, wherein the first organic solvent is selected from acetone, tetrahydrofuran, N,N-dimethylformamide, dichloromethane, dichloroethane, or acetonitrile; the second organic solvent is selected from toluene, dioxane, tetrahydrofuran, N,N-dimethylformamide, N,N-dimethylacetamide or N-methylmorpholine; the third organic solvent is tetrahydrofuran, methanol, ethanol, dichloromethane, dichloroethane, N,N-dimethylacetamide or N,N-dimethylformamide; the fourth solvent is selected from methanol, ethanol, tert-butanol, n-butanol or water, and fifth solvent is selected from dichloromethane, ethyl acetate, acetone or water; the first base selected from K₂CO₃, Cs₂CO₃, NaOH, KOH, NaH, tert-BuOK, tert-BuONa, triethylamine or diisopropylethylamine; the second base selected from tert-BuOK, tert-BuONa, Cs₂CO₃ or K₂CO₃; the third base selected from NaH, n-BuLi, or Cs₂CO₃; the palladium catalyst is selected from Pd(OAc)₂, Pd₂(dba)₃, or Pd(dppf)Cl₂; the ligand is selected from BiNap, Xantphose, or S-Phose; the oxidizing agent is mCPBA or Oxone; the reducing agent is selected from NaBH(OAc)₃, NaBH₄, or NaBH(CN)₃.

15. A method for preparing a compound of claim 1, the method comprising reacting a compound of formula (f)

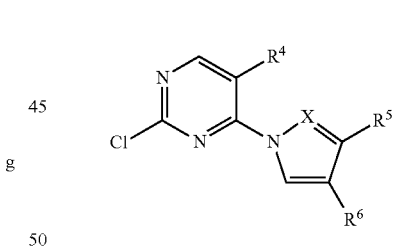

f in which R⁴, R⁵, R⁶ and X are as defined in claim 1, with an aniline derivative of formula (d)

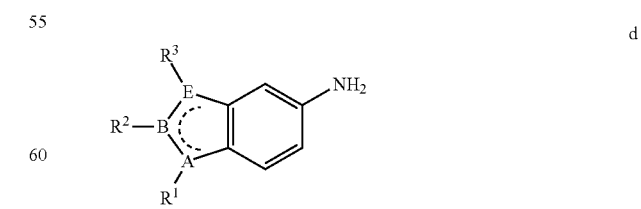

d in which A, B, E, R¹, R², and R³ are as defined in claim 1, in the presence of a base and a palladium catalyst under conditions such that a compound of Formula I is prepared.

16. A method for treating a condition selected from the group consisting of systemic lupus erythematosus (SLE), discoid (cutaneous) lupus, asthma, and rheumatoid arthritis, the method comprising administering to a patient in need of such treatment an effective amount of a compound of claim 1.

17. The method of claim 16, wherein said compound is administered singly or in combination with one or more additional therapeutic agents.

18. The method of claim 16 wherein said compound is administered via intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration.

19. A method for treating Non-Hodgkin's Lymphomas, the method comprising administering to a patient in need thereof an effective amount of a compound of claim 1.

20. The method of claim 19, wherein the Non-Hodgkin's Lymphoma is selected from the group consisting of follicular lymphoma, mantle cell lymphoma, capsule cell lymphoma, diffuse large B cell lymphoma, T-cell lymphoma, and chronic lymphocytic lymphoma.

* * * * *

UNITED STATES PATENT AND TRADEMARK OFFICE
CERTIFICATE OF CORRECTION

PATENT NO.         : 8,871,778 B2                                    Page 1 of 1
APPLICATION NO.    : 13/745734
DATED              : October 28, 2014
INVENTOR(S)        : Jang-Sik Choi It is certified that error appears in the above-identified patent and that said Letters Patent is hereby corrected as shown below:

Claims

In Claim 1:

At column 127, line number 42, Please correct "A is C" to "A is N".

Signed and Sealed this
Thirteenth Day of December, 2016

Michelle K. Lee
*Director of the United States Patent and Trademark Office*